(12) United States Patent
Aggeler et al.

(10) Patent No.: US 11,897,958 B2
(45) Date of Patent: *Feb. 13, 2024

(54) HYBRIDOMA CLONES, MONOCLONAL ANTIBODIES TO VSIG-4, AND METHODS OF MAKING AND USING

(71) Applicant: BIO-TECHNE CORPORATION, Minneapolis, MN (US)

(72) Inventors: Birte Aggeler, Minneapolis, MN (US); Christine Goetz, Blaine, MN (US); Jody Bonnevier, Chanhassen, MN (US); Christopher Carlin Valley, Minnetonka, MN (US); Christopher Hammerbeck, Shoreview, MN (US); Ernesto Ruben Resnik, Minneapolis, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 607 days.

This patent is subject to a terminal disclaimer.

(21) Appl. No.: 16/997,797

(22) Filed: Aug. 19, 2020

(65) Prior Publication Data

US 2021/0087276 A1    Mar. 25, 2021

Related U.S. Application Data

(63) Continuation of application No. 16/019,011, filed on Jun. 26, 2018, now Pat. No. 10,752,689.

(60) Provisional application No. 62/524,821, filed on Jun. 26, 2017.

(51) Int. Cl.
| | |
|---|---|
| *C07K 16/28* | (2006.01) |
| *A61K 31/573* | (2006.01) |
| *A61P 37/06* | (2006.01) |
| *A61P 35/00* | (2006.01) |
| *C12N 5/16* | (2006.01) |

(52) U.S. Cl.
CPC ........ *C07K 16/2854* (2013.01); *A61K 31/573* (2013.01); *A61P 35/00* (2018.01); *A61P 37/06* (2018.01); *C07K 16/2803* (2013.01); *C12N 5/163* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez et al. |
| 5,223,409 A | 6/1993 | Ladner et al. |
| 2009/0162356 A1 | 6/2009 | Lookeren Campagne |
| 2018/0371095 A1 | 12/2018 | Aggeler et al. |

FOREIGN PATENT DOCUMENTS

| | | |
|---|---|---|
| CN | 105924515 | 9/2016 |
| CN | 106188298 A | 12/2016 |
| KR | 20150030840 A * | 3/2015 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 2019/005817 A1 | 1/2019 |

OTHER PUBLICATIONS

Vogt, 2006, J. Clin. Invest. vol. 116: 2817-2826.*
Li, 2012, Acta Histochemica, vol. 114: 733-743.*
Machine Translation for KR20150030840A, Mar. 2023, pp. 1-6.*
Xu et al., "VSIG4 is highly expressed and correlated with poor prognosis of high-grade glioma patients" Am J Transl Res, Jan. 1, 2015; 7(6):1172-1180.
Kim et al., "Characterization of monoclonal antibody specific to the Z39Ig protein, a member of immunoglobulin superfamily" Immunology Letters, Jul. 15, 2005; 99(2):153-161.
Kwang et al., "Extracellular stimulation of VSIG4/complement receptor Ig suppressed intracellular bacterial infection by inducing autophagy" Autophagy, Jul. 20, 2016; 12(9):1647-1659.
Wolff et al., "American Society of Clinical Oncology/College of American Pathologists Guideline Recommendations for Human Epidermal Growth Factor Receptor 2 Testing in Breast Cancer" Arch Pathol Lab Med, Jan. 1, 2007; 131(1):18-43.
American Type Culture Collection, Certificate of Deposit dated Jun. 22, 2017, deposited on behalf of Bio-Techne / R&D Systems Inc., ATTC Nos. Ms x hVSIG4 528906.11 (ATCC Accession No. PTA-124178); Ms x hVSIG4 528908.11 (ATCC Accession No. PTA-124179); Ms x hVSIG4 528910.111 (ATCC Accession No. PTA-124180); Ms x hVSIG4 528912.11 (ATCC Accession No. PTA-124181); Ms x hVSIG4 528922.111 (ATCC Accession No. PTA-124182); Ms x hVSIG4 528927.111 (ATCC Accession No. PTA-124183); 2 pages.
American Type Culture Collection, Certificate of Deposit dated Jun. 22, 2017, deposited on behalf of Bio-Techne / R&D Systems Inc., ATTC Nos. Rt x hVSIG4 489509.11 (ATCC Accession No. PTA-124184); Rt x hVSIG4 489517.111 (ATCC Accession No. PTA-124185); Rt x hVSIG4 489518.11 (ATCC Accession No. PTA-124186); Ms x hVSIG4 528902.11 (ATCC Accession No. PTA-124187); Ms x hVSIG4 528903.111 (ATCC Accession No. PTA-124188); Ms x hVSIG4 528905.11 (ATCC Accession No. PTA-124189); 2 pages.
Chothia et al., "Canonical structures for the hypervariable regions of immunoglobulins" J Mol Biol, 1987; 196(4):901-17.
Gorgani et al., "Regulation of CRIg expression and phagocytosis in human macrophages by arachidonate, dexamethasone, and cytokines" Am J Pathol, 2011; 179(3):1310-8.

(Continued)

*Primary Examiner* — Amy E Juedes
(74) *Attorney, Agent, or Firm* — Mueting Raasch Group

(57) ABSTRACT

Described herein are monoclonal antibodies that bind to VSIG-4 including antibodies that block the binding of VSIG-4 to SIGLEC-7, compositions including the monoclonal antibodies, and methods of making and using those antibodies and compositions.

19 Claims, 44 Drawing Sheets

(56) References Cited

OTHER PUBLICATIONS

Holliger et al., "Diabodies": small bivalent and bispecific antibody fragments Proc Natl Acad Sci USA, 1993; 90(14):6444-8.
Irvine et al., "CRIg-expressing peritoneal macrophages are associated with disease severity in patients with cirrhosis and ascites" JCI Insight, 2016; 1(8):e86914.
Jandus et al., "Interactions between Siglec-7/9 receptors and ligands influence NK cell-dependent tumor immunosurveillance" J Clin Invest, 2014; 124(4):1810-20. Epub Feb. 24, 2014.
Jones et al., "Replacing the complementarity-determining regions in a human antibody with those from a mouse" Nature, 1986; 321(6069):522-5.
Jung et al., "Endogenous VSIG4 negatively regulates the helper T cell-mediated antibody response" Immunol Letters, 2015; 165(2):78-83.
Karjalainen et al., "An unusual type of V-J joining diversifies the primary repertoire of mouse λ1 light chains" Nature, 1985; 314:544-6.
Kim et al. "Extracellular stimulation of VSIG4/complement receptor Ig suppresses intracellular bacterial infection by inducing autophagy" Autophagy, 2016; 12(9):1647-59.
Klimka et al., "Human anti-CD30 recombinant antibodies by guided phage antibody selection using cell panning" Br J Cancer, Jul. 2000; 83(2):252-60.
Kohler and Milstein, "Derivation of specific antibody-producing tissue culture and tumor lines by cell fusion" Eur J Immunol, 1976; 6(7):511-9.
Kostelny et al., "Formation of a bispecific antibody by the use of leucine zippers" J Immunol, 1992; 148(5):1547-53.
Li et al., "VSIG4 inhibits proinflammatory macrophage activation by reprogramming mitochondrial pyruvate metabolism" Nat Commun, Nov. 6, 2017; 8(1):1322.
Liao et al., "VSIG4 expression on macrophages facilitates lung cancer development" Lab Invest, 2014; 94(7):706-15. Epub May 26, 2014.
Mizrahi et al., "Siglec-7 is an inhibitory receptor on human mast cells and basophils" J Allergy Clin Immunol, 2014; 134(1):230-3.
National Center for Biotechnology Information, National Library of Medicine, National Institutes of Health, "VSIG4 V-set and immunoglobulin domain containing 4 [ *Homo sapiens* (human) ]" Gene ID 11326, updated on Aug. 5, 2018 [online]. Bethesda, MD [retrieved on Oct. 23, 2018]. Retrieved from the Internet: <URL: ncbi.nlm.nih.gov/gene/11326>; 10 pgs.
Navegantes et al., "Immune modulation of some autoimmune diseases: the critical role of macrophages and neutrophils in the innate and adaptive immunity" J Transl Med, 2017; 15(1):36.
Nicoll et al., "A New Topological Model of the Cardiac Sarcolemmal Na+-Ca2+ Exchanger*" J Biol Chem, 1999; 274(2):3910-7.

Orlandi et al., "Cloning immunoglobulin variable domains for expression by the polymerase chain reaction" Proc Natl Acad Sci USA, May 1989; 86(10):3833-7.
Sambrook et al., *Molecular cloning: a laboratory manual, 2$^{nd}$ ed.* Cold Spring Harbor Laboratory Press: Cold Spring Harbor, New York; 1989. Cover page, title page, and table of contents. 30 pgs.
Schnaar et al., "Sialic acids in the brain: gangliosides and polysialic acid in nervous system development, stability, disease, and regeneration" Physiological Rev, 2014; 94(2):461-518.
Scott et al., "Antibody therapy of cancer" Nat Rev Cancer, Mar. 22, 2012; 12(4):278-87.
Shao et al., "Siglec-7 Defines a Highly Functional Natural Killer Cell Subset and Inhibits Cell-Mediated Activities" Scand J Immunol, 2016; 84(3):182-90.
Singer et al., "Optimal humanization of 1B4, an anti-CD18 murine monoclonal antibody, is achieved by correct choice of human V-region framework sequences" J Immunol, 1993; 150(7):2844-57.
Songsivilai and Lachmann, "Bispecific antibody: a tool for diagnosis and treatment of disease" Clin Exp Immunol. 1990;79(3):315-21.
Takeda et al., "Construction of chimaeric processed immunoglobulin genes containing mouse variable and human constant region sequences" Nature, Apr. 4-10, 1985; 314(6010):452-4.
Tanaka et al., "Phenotypic and functional profiles of CRIg (Z39Ig)-expressing macrophages in the large intestine" Innate Immun, Apr. 2012; 18(2):258-67. Epub Jul. 18, 2011.
Traunecker et al., "Bispecific single chain molecules (Janusins) target cytotoxic lymphocytes on HIV infected cells" EMBO J, Dec. 1991; 10(12):3655-9.
Traunecker et al., "Janusin: new molecular design for bispecific reagents" Int J Cancer Suppl, 1992; 7:51-2.
Universal Protein Resource (UniProt), UniProt Consortium, Accession No. F6TUL9 [retrieved on Oct. 23, 2018]. Retrieved from the internet: <uniprot.org/uniprot/F6TUL9>. 8 pages.
Universal Protein Resource (UniProt), UniProt Consortium, Accession No. Q9Y279 [retrieved on Oct. 23, 2018]. Retrieved from the internet: <uniprot.org/uniprot/Q9Y279>. 12 pages.
Varchetta et al., "Engagement of Siglec-7 Receptor Induces a Pro-Inflammatory Response Selectively in Monocytes" PLoS One, Sep. 28, 2012; 7(9):e45821.
Varchetta et al., "Sialic acid-binding Ig-like lectin-7 interacts with HIV-1 gp120 and facilitates infection of CD4pos T cells and macrophages" Retrovirology, Dec. 13, 2013; 10:154.
Vogt et al., "VSIG4, a B7 family-related protein, is a negative regulator of T cell activation" J Clin Invest, Oct. 2006; 116(10):2817-26.
Xu et al., "VSIG4 is highly expressed and correlated with poor prognosis of high-grade glioma patients" Am J Transl Res, 2015; 7(6):1172-80.
International Patent Application No. PCT/US2018/039532, filed Jun. 26, 2018; International Search Report and Written Opinion dated Dec. 21, 2018; 10 pages.

* cited by examiner

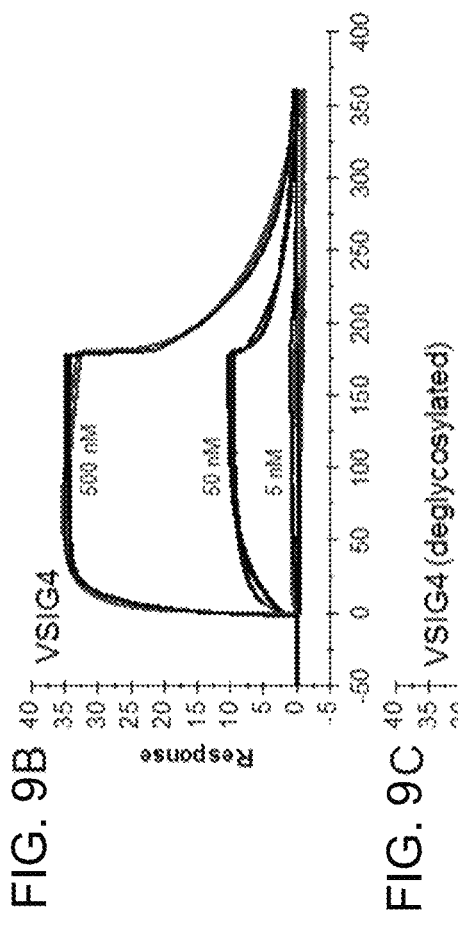
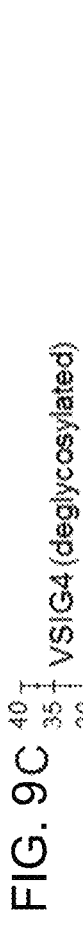
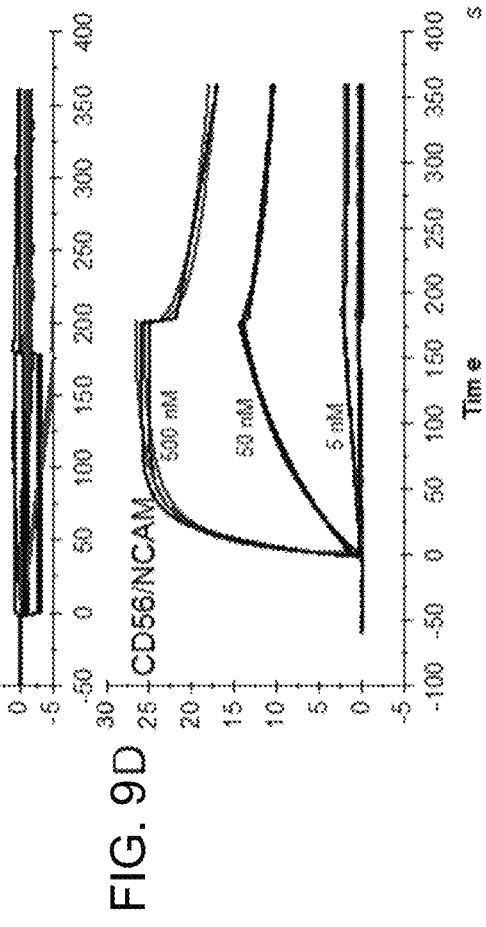
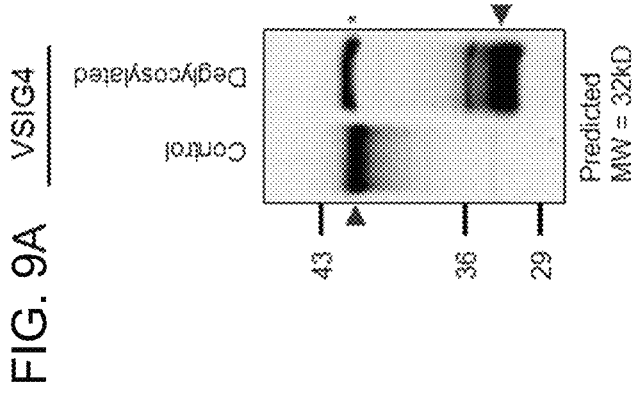
FIG. 9A
FIG. 9B
FIG. 9C
FIG. 9D

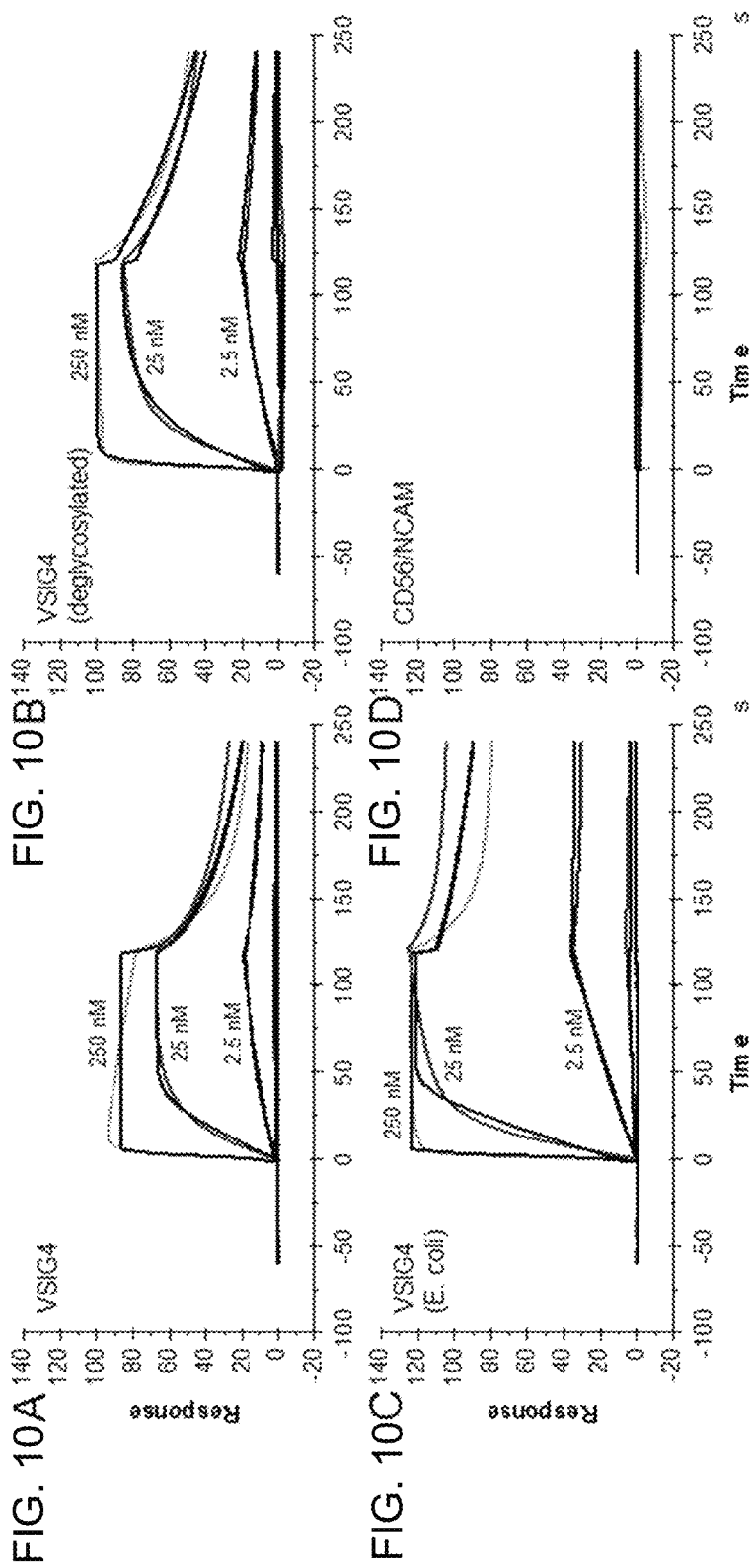

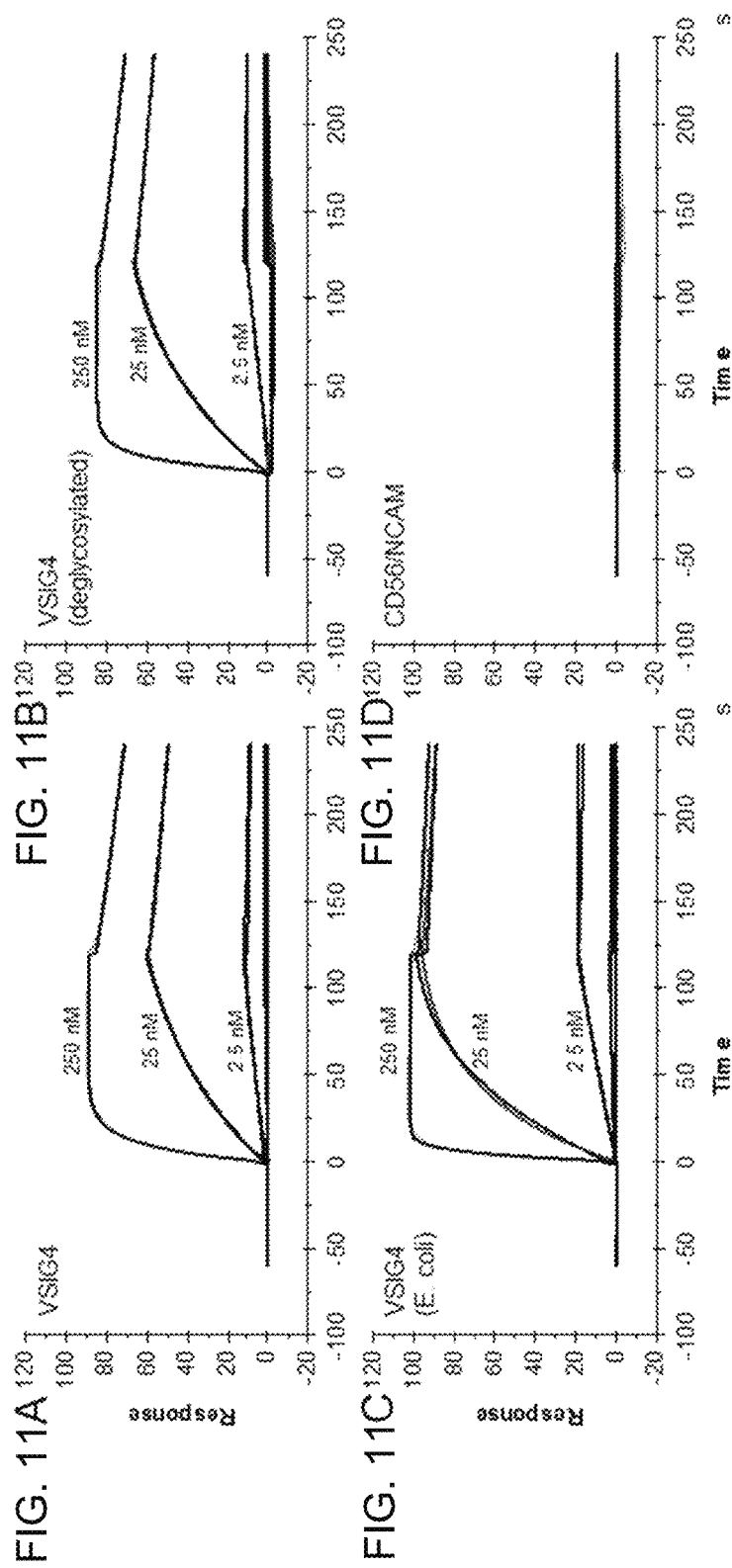

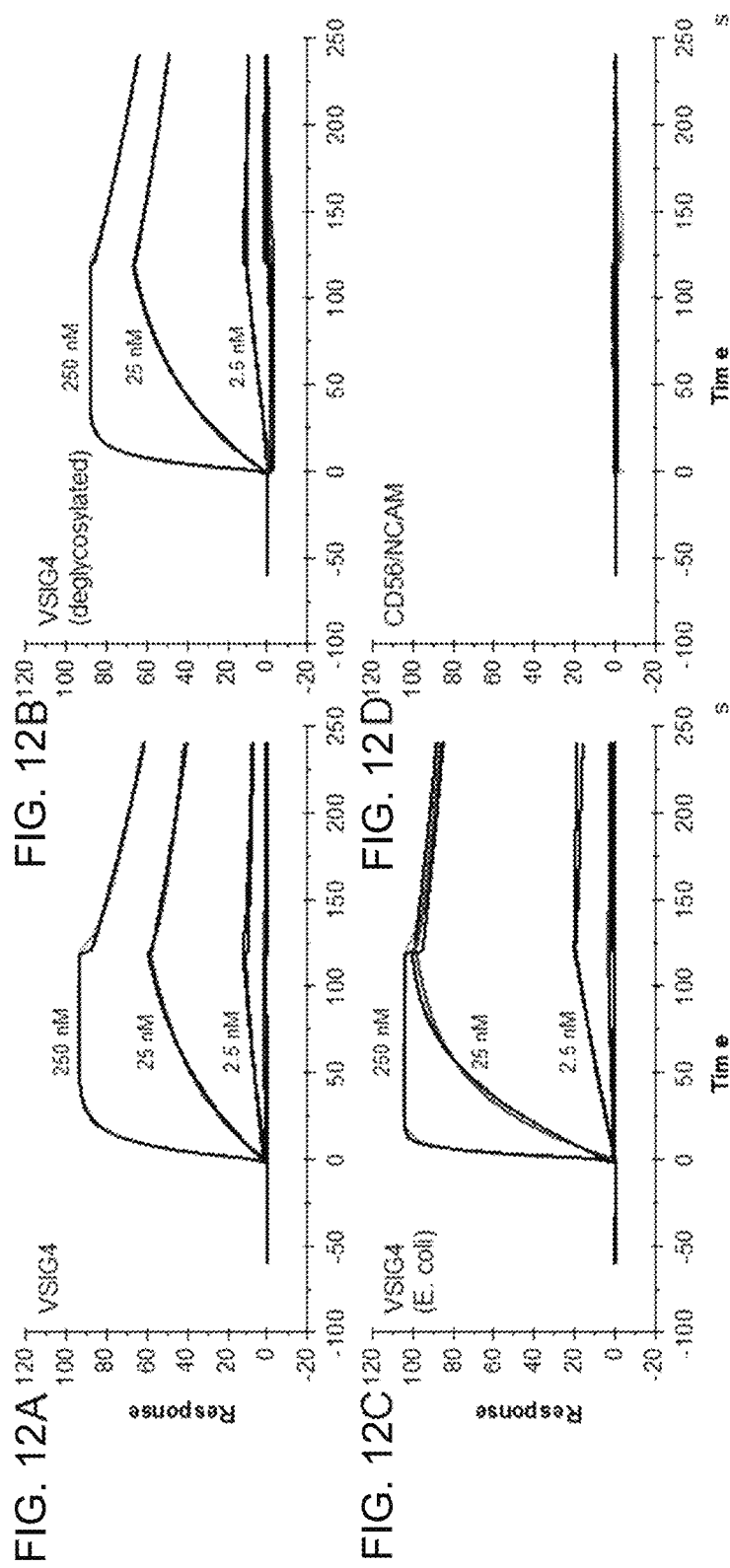

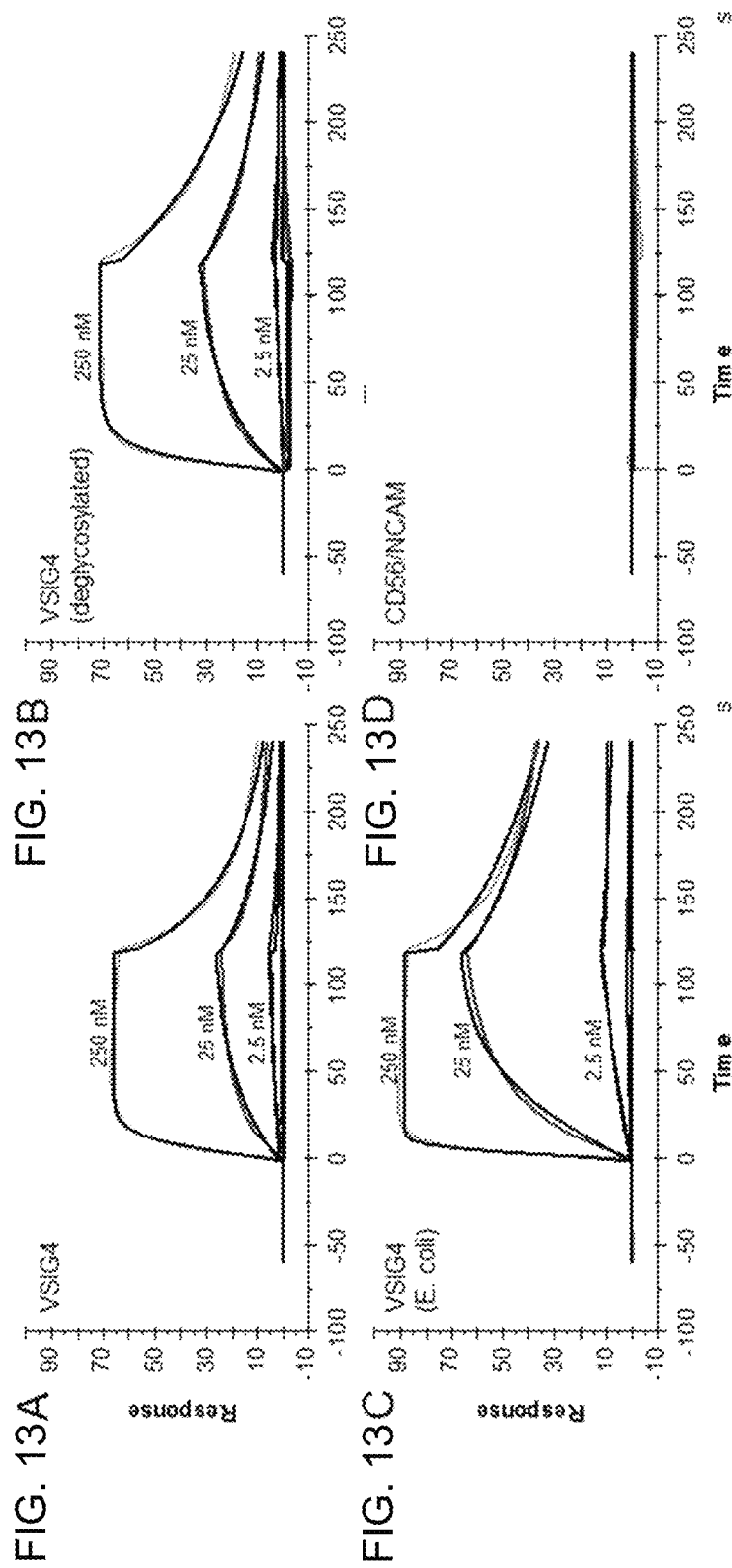

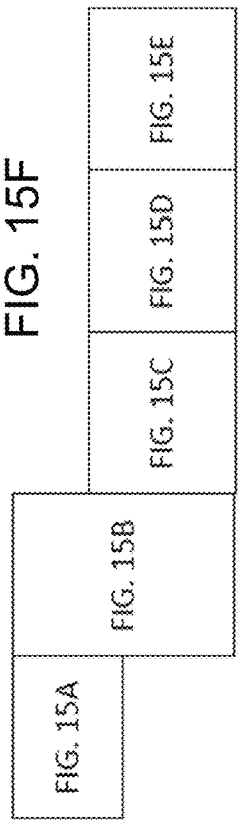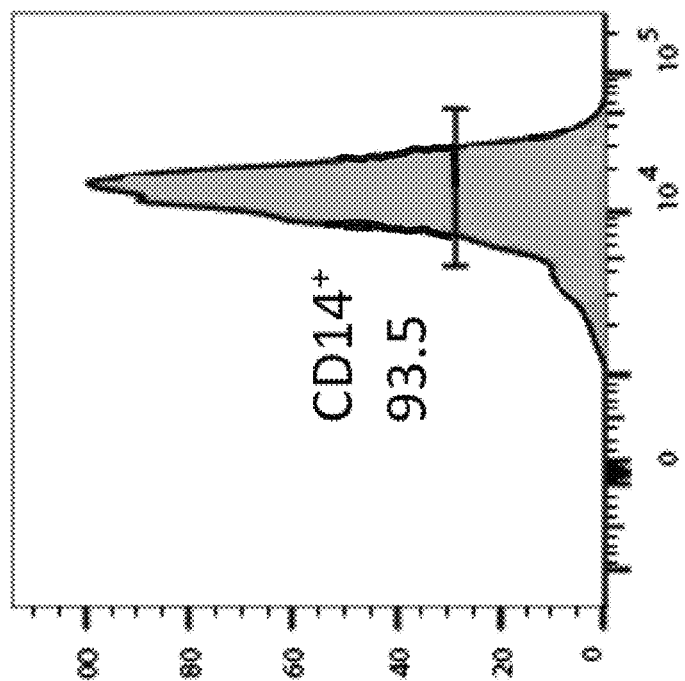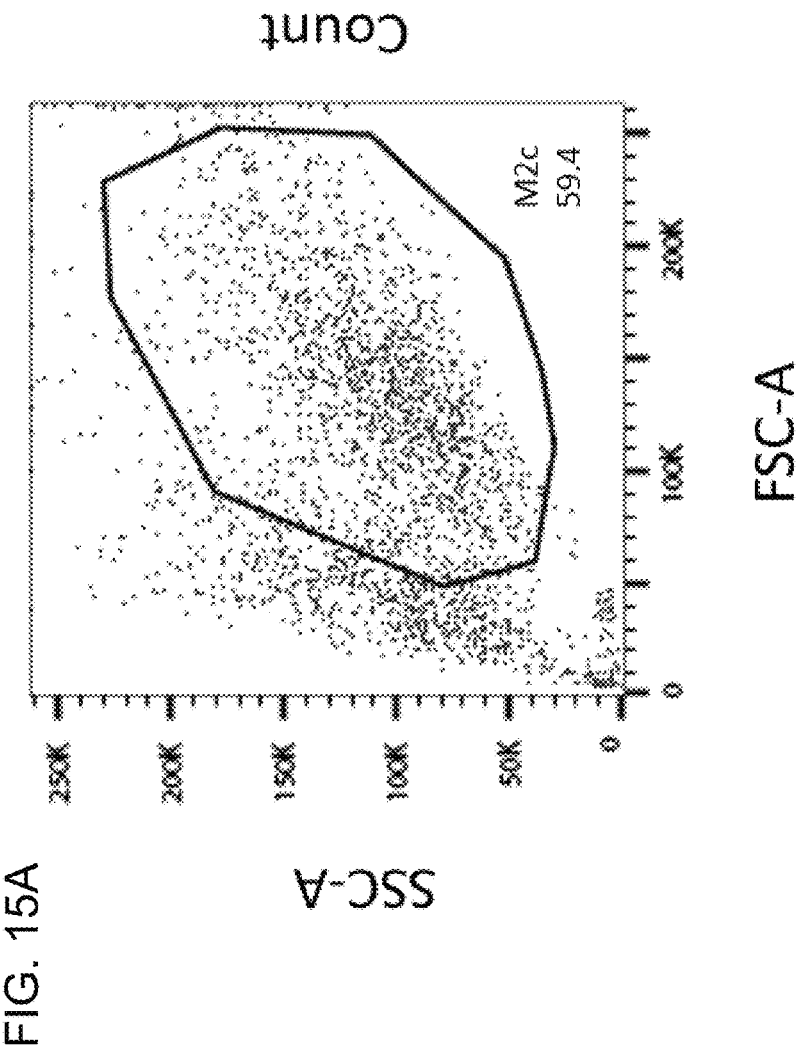
FIG. 15A

Sig7 protein: 25 ug/mL

FIG. 16B
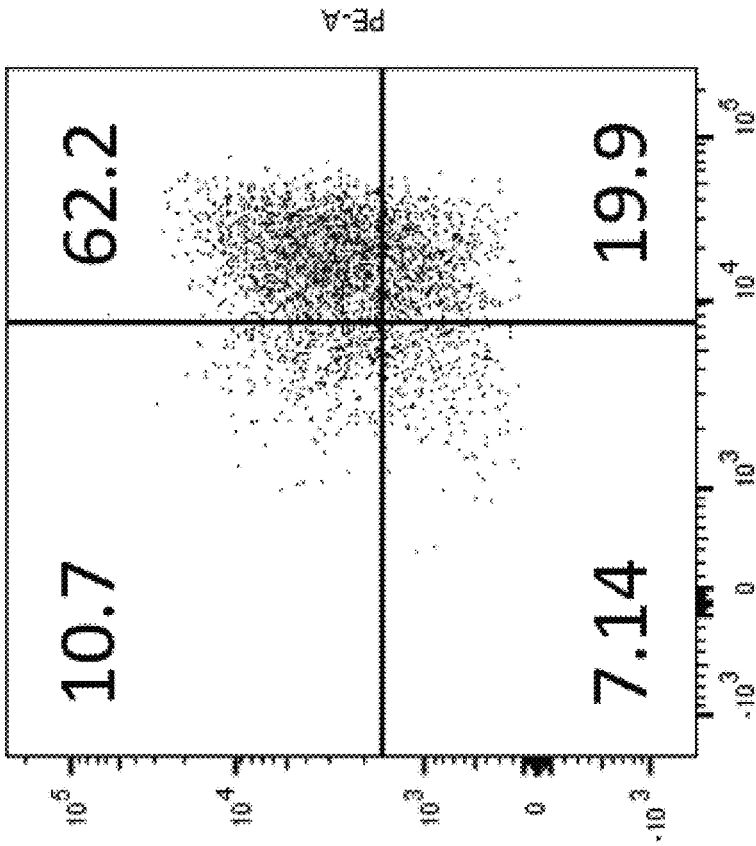
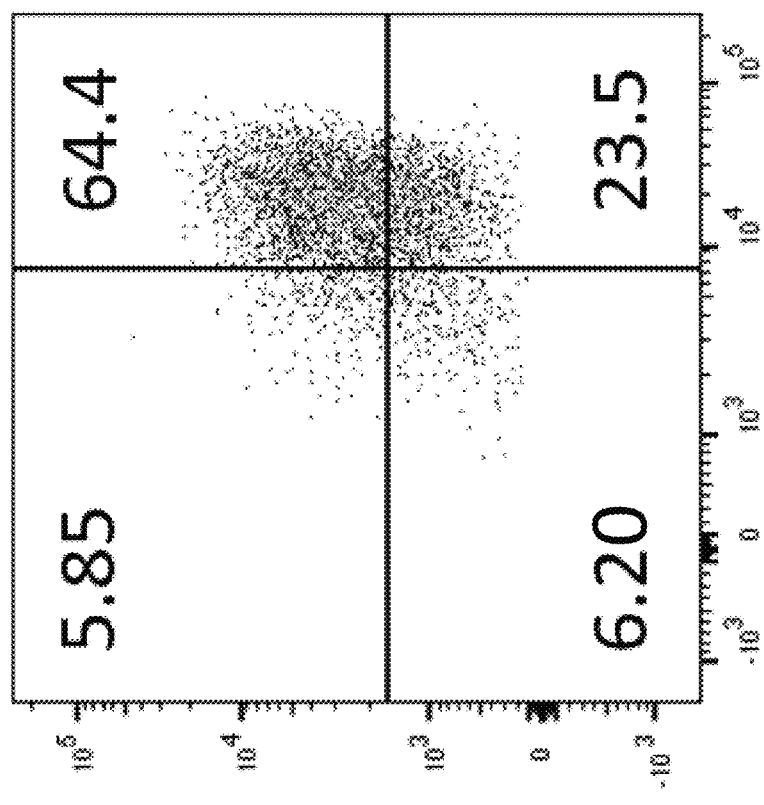
ncentration of VSIG4 blocking antibody

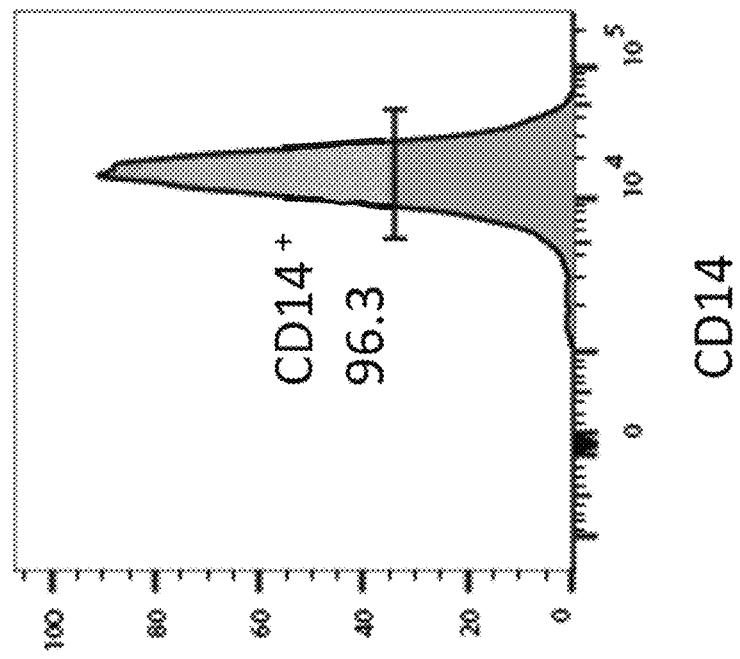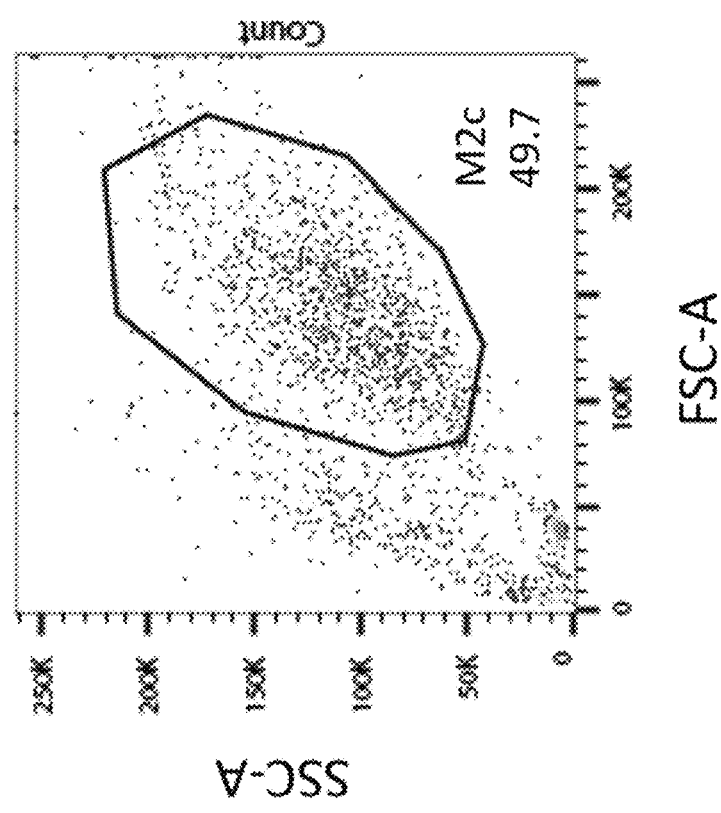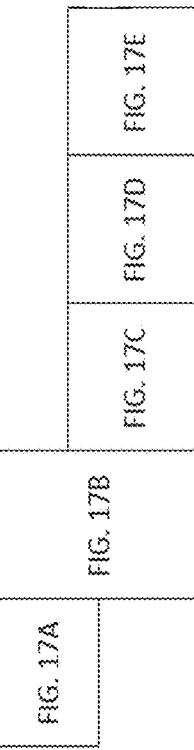

FIG. 17B
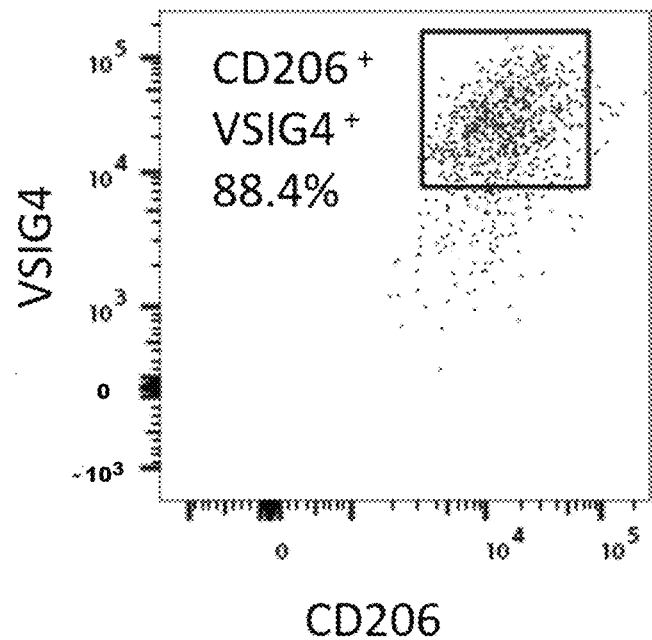
- VSIG4 expression on M2c macrophages using anti-VSIG4 clone 528906 for detection
- Co-expression with CD206
Macrophages blocked with anti-VSIG4 clone 528908
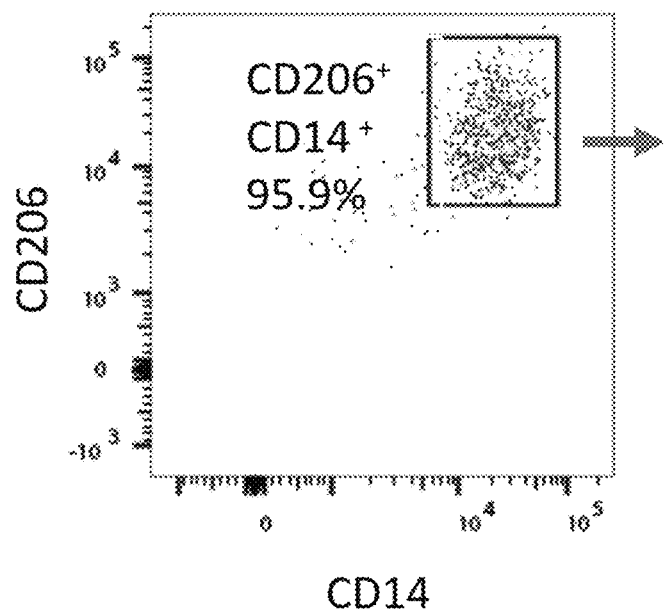

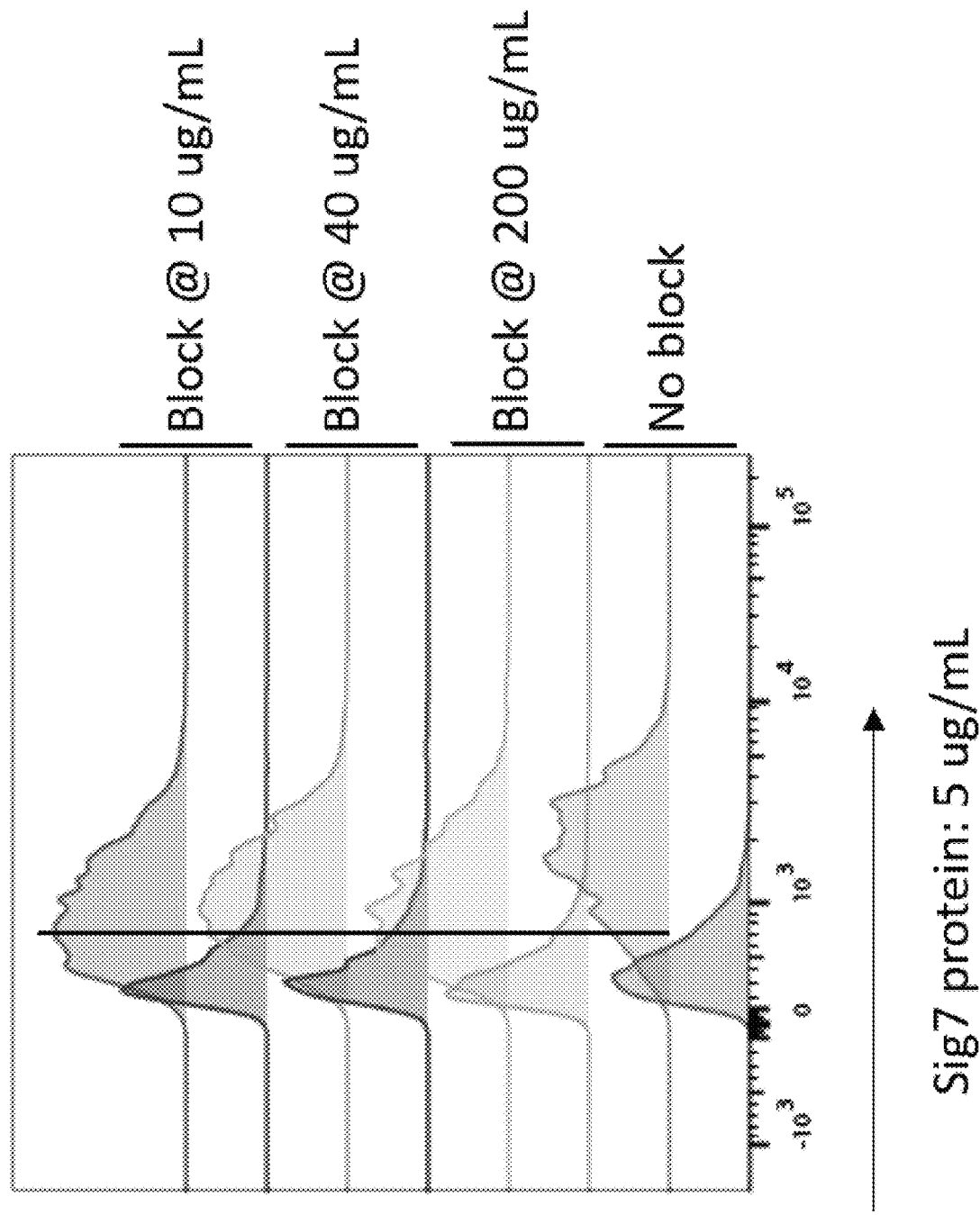

| FIG. 18A | FIG. 18B | FIG. 18C |
| FIG. 18D | FIG. 18E | FIG. 18F |
| FIG. 18G | FIG. 18H | FIG. 18I |

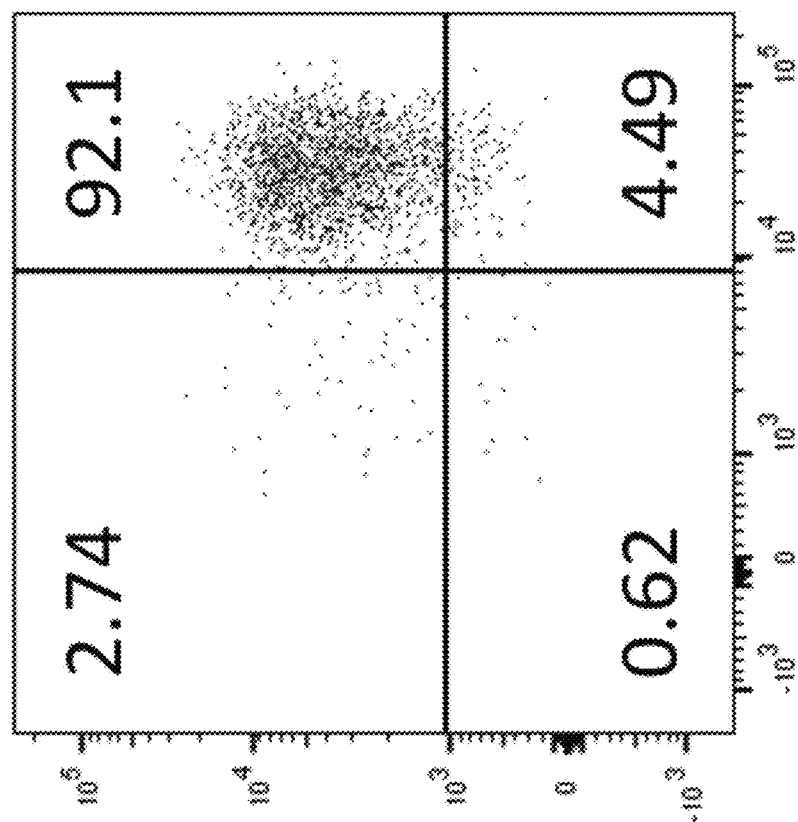
FIG. 18D

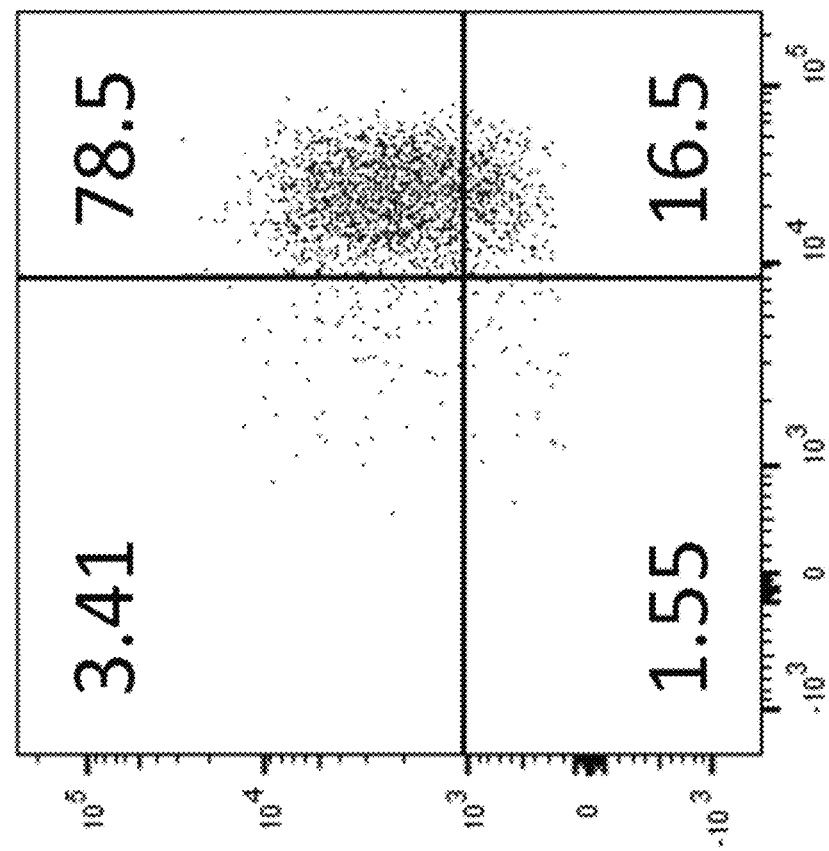
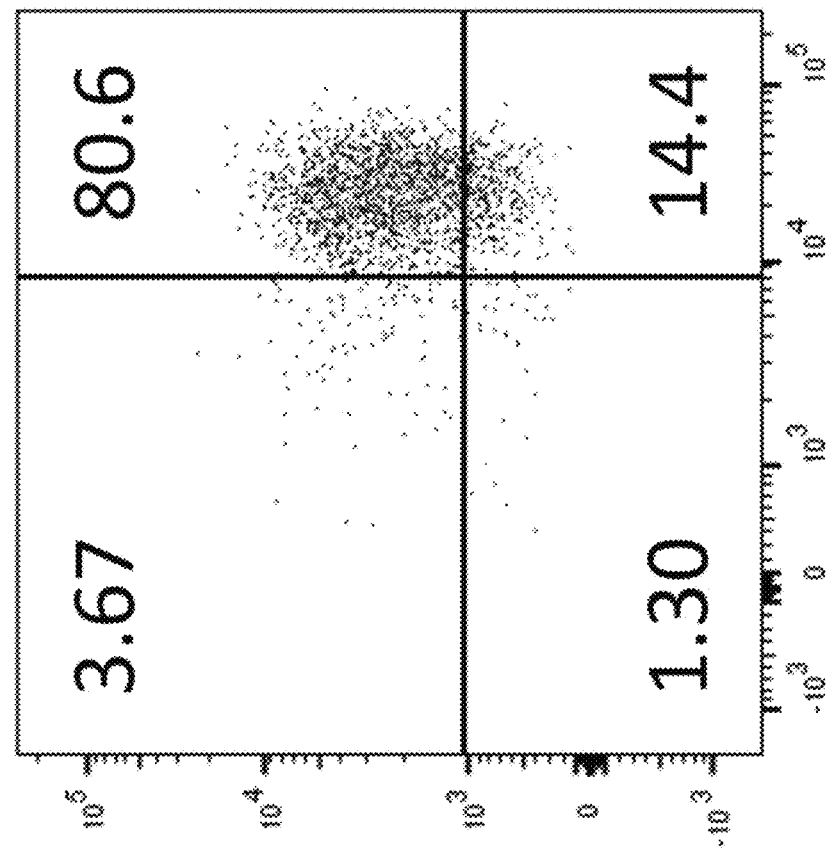
FIG. 18E

HYBRIDOMA CLONES, MONOCLONAL ANTIBODIES TO VSIG-4, AND METHODS OF MAKING AND USING

CONTINUING APPLICATION DATA

This application is a continuation application of U.S. patent application Ser. No. 16/019,011, filed Jun. 26, 2018, which claims the benefit of U.S. Provisional Application Ser. No. 62/524,821, filed Jun. 26, 2017, the disclosures of each of which are incorporated by reference herein in their entireties.

BACKGROUND

V-set and Ig domain-containing 4 (VSIG-4 or VSIG4) is a C3 complement receptor, a B7 family-related protein, and a negative regulator of T cell activation. VSIG-4 expression has been observed to be restricted to tissue macrophages, and it has been shown to be down-regulated in response to lipopolysaccharide (LPS) (Vogt et al. (2006) *J. of Clin. Invest.* 116:2817). In healthy tissue, VSIG-4 is expressed on tissue-resident macrophages and functions as a complement receptor to opsonize bacterial pathogens. Massive infiltrates of VSIG-4$^+$ macrophages into the tumor microenvironment have been observed in patients diagnosed with non-small cell lung cancer (Liao et al. (2014) Lab. Invest. 94:706), and high VSIG-4 expression has also been correlated with high-grade glioma and poor patient prognosis (Xu et al. (2015) *Am. J. Transl. Res.* 7:1172).

SUMMARY OF THE INVENTION

In some aspects, this disclosure describes an antibody that binds to VSIG-4. In some embodiments, the antibody abrogates binding of VSIG-4 to a VSIG-4 ligand. In some embodiments, the antibody abrogates the binding of VSIG-4 to Sialic acid-binding Ig-like lectin 7 (SIGLEC-7, SIGLEC7, Siglec-7, or Siglec7).

In some embodiments, the antibody may be produced by at least one of the following clones deposited with the American Type Culture Collection (ATCC), 10801 University Boulevard, Manassas, VA 20110, USA, on May 11, 2017: Ms x hVSIG4 528902.11 (ATCC Accession No. PTA-124187); Ms x hVSIG4 528903.111 (ATCC Accession No. PTA-124188); Ms x hVSIG4 528905.11 (ATCC Accession No. PTA-124189); Ms x hVSIG4 528906.11 (ATCC Accession No. PTA-124178); Ms x hVSIG4 528908.11 (ATCC Accession No. PTA-124179); Ms x hVSIG4 528910.111 (ATCC Accession No. PTA-124180); Ms x hVSIG4 528912.11 (ATCC Accession No. PTA-124181); Ms x hVSIG4 528922.111 (ATCC Accession No. PTA-124182); Ms x hVSIG4 528927.111 (ATCC Accession No. PTA-124183); Rt x hVSIG4 489509.11 (ATCC Accession No. PTA-124184); Rt x hVSIG4 489517.111 (ATCC Accession No. PTA-124185); and Rt x hVSIG4 489518.11 (ATCC Accession No. PTA-124186). These deposits were made in accordance with the Budapest Treaty on the International Recognition of the Deposit of Microorganisms for the Purposes of Patent Procedure.

In some embodiments, the antibody includes at least one of a heavy chain variable region and a light chain variable region of a monoclonal antibody produced by at least one of the following clones: Ms x hVSIG4 528902.11 (ATCC Accession No. PTA-124187); Ms x hVSIG4 528903.111 (ATCC Accession No. PTA-124188); Ms x hVSIG4 528905.11 (ATCC Accession No. PTA-124189); Ms x hVSIG4 528906.11 (ATCC Accession No. PTA-124178); Ms x hVSIG4 528908.11 (ATCC Accession No. PTA-124179); Ms x hVSIG4 528910.111 (ATCC Accession No. PTA-124180); Ms x hVSIG4 528912.11 (ATCC Accession No. PTA-124181); Ms x hVSIG4 528922.111 (ATCC Accession No. PTA-124182); Ms x hVSIG4 528927.111 (ATCC Accession No. PTA-124183); Rt x hVSIG4 489509.11 (ATCC Accession No. PTA-124184); Rt x hVSIG4 489517.111 (ATCC Accession No. PTA-124185); and Rt x hVSIG4 489518.11 (ATCC Accession No. PTA-124186).

In some embodiments, the antibody includes at least one of a heavy chain variable region comprising the complementarity determining regions (CDRs) of the heavy chain variable region of a monoclonal antibody produced by at least one of the following clones and a light chain variable region comprising the complementarity determining regions (CDRs) of the light chain variable region of a monoclonal antibody produced by at least one of the following clones: Ms x hVSIG4 528902.11 (ATCC Accession No. PTA-124187); Ms x hVSIG4 528903.111 (ATCC Accession No. PTA-124188); Ms x hVSIG4 528905.11 (ATCC Accession No. PTA-124189); Ms x hVSIG4 528906.11 (ATCC Accession No. PTA-124178); Ms x hVSIG4 528908.11 (ATCC Accession No. PTA-124179); Ms x hVSIG4 528910.111 (ATCC Accession No. PTA-124180); Ms x hVSIG4 528912.11 (ATCC Accession No. PTA-124181); Ms x hVSIG4 528922.111 (ATCC Accession No. PTA-124182); Ms x hVSIG4 528927.111 (ATCC Accession No. PTA-124183); Rt x hVSIG4 489509.11 (ATCC Accession No. PTA-124184); Rt x hVSIG4 489517.111 (ATCC Accession No. PTA-124185); and Rt x hVSIG4 489518.11 (ATCC Accession No. PTA-124186).

In some embodiments, the antibody may be coupled directly or indirectly to a detectable marker. In some embodiments, the antibody includes an IgG antibody.

In some embodiments, the antibody includes an antigen-binding fragment including, for example, a Fab fragment, a Fab' fragment, a F(ab)$_2$ fragment, and a Fv fragment.

In some embodiments, the antibody may abrogate binding of VSIG-4 to a VSIG-4 ligand. In some embodiments, a VSIG-4 ligand can include SIGLEC-7. In some embodiments, at least one of VSIG-4 and the VSIG-4 ligand may be on a cell surface. In some embodiments, VSIG-4 may be expressed on the surface of a macrophage including, for example, an M2c macrophage. In some embodiments, the antibody may abrogate a cell-cell interaction.

In some embodiments, the antibody may bind to an extracellular domain of VSIG-4. In some embodiments, the antibody may bind to a VSIG-4 polypeptide. In some embodiments, the antibody may bind to both glycosylated and unglycosylated VSIG-4.

This disclosure further describes compositions and kits including an antibody described herein.

In another aspect, this disclosure describes a method of treating a mammalian cancer that includes exposing a mammal including a mammalian cancer cell to an antibody described herein.

In some embodiments, VSIG-4 expression is amplified in a patient sample comprising the mammalian cancer cell. In some embodiments, VSIG-4 expression is amplified in a macrophage of the patient sample comprising the mammalian cancer cell. In some embodiments, the mammalian cancer cell comprises a lung cancer cell or a glioma.

In some embodiments, the mammalian cancer cell is also exposed to chemotherapy or radiation therapy.

In a further aspect, this disclosure describes a method of detecting cancer in a mammal including exposing a mammalian cancer cell to an antibody described herein.

In yet another aspect, this disclosure describes a method of treating an autoimmune disease in a mammal that includes exposing a cell of the mammal to an antibody described herein.

In an additional aspect, this disclosure is directed to the following hybridoma cell lines and monoclonal antibodies produced by the following hybridoma cell lines:

Ms x hVSIG4 528902.11, deposited as ATCC accession number PTA-124187;
Ms x hVSIG4 528903.111, deposited as ATCC accession number PTA-124188;
Ms x hVSIG4 528905.11, deposited as ATCC accession number PTA-124189;
Ms x hVSIG4 528906.11, deposited as ATCC accession number PTA-124178;
Ms x hVSIG4 528908.11, deposited as ATCC accession number PTA-124179;
Ms x hVSIG4 528910.111, deposited as ATCC accession number PTA-124180;
Ms x hVSIG4 528912.11, deposited as ATCC accession number PTA-124181;
Ms x hVSIG4 528922.111, deposited as ATCC accession number PTA-124182;
Ms x hVSIG4 528927.111, deposited as ATCC accession number PTA-124183;
Rt x hVSIG4 489509.11, deposited as ATCC accession number PTA-124184;
Rt x hVSIG4 489517.111, deposited as ATCC accession number PTA-124185; and
Rt x hVSIG4 489518.11, deposited as ATCC accession number PTA-124186.

The term "antibody" as used herein refers to a molecule that contains at least one antigen binding site that immunospecifically binds to a particular antigen target of interest. The term "antibody" thus includes but is not limited to a full length antibody and/or its variants, a fragment thereof, peptibodies and variants thereof, monoclonal antibodies (including full-length monoclonal antibodies), polyclonal antibodies, multispecific antibodies (for example, bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. An antibody of the present disclosure thus encompasses antibody fragments capable of binding to a biological molecule (such as an antigen or receptor) or portions thereof, including but not limited to Fab, Fab' and F(ab')2, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody may be of any type (for example, IgG, IgE, IgM, IgD, IgA and IgY), class (for example, IgG1, IgG2, IgG3, IgG4, IgA1 and IgA2), or subclass.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies may be synthesized by hybridoma cells uncontaminated by other immunoglobulin producing cells. Alternatively, the monoclonal antibody may be produced recombinantly including, for example, by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. In some embodiments, the term "monoclonal" is used herein to refers to an antibody that is derived from a clonal population of cells, including any eukaryotic, prokaryotic, or phage clone, and not the method by which the antibody was engineered.

As used herein, the term "VSIG-4 ligand" refers to a protein binding partner of VSIG-4 and can include both a ligand and/or a counter-receptor. An interaction between VSIG-4 and a VSIG-4 may signal in one or both directions.

As used herein, "isolated" refers to material removed from its original environment (for example, the natural environment if it is naturally occurring), and thus is altered "by the hand of man" from its natural state.

As used herein, "room temperature" is 16° C. to 26° C. or, more preferably, 18° C. to 24° C. In some embodiments, "room temperature" is 20° C. to 22° C.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide may be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Advances in Applied Mathematics* 2:482-489, to find the best segment of homology between two sequences. When using BESTFIT or any other sequence alignment program to determine whether a particular sequence is, for example, 95% identical to a reference sequence according to the present invention, the parameters are set such that the percentage of identity is calculated over the full length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (for example, an antibody) and its binding partner (for example, an antigen or antigenic epitope). The affinity of a molecule X for its partner Y is represented by the dissociation constant ($K_D$), which can generally be determined by using methods known in the art, for example, using the BIACORE biosensor, commercially available from BIACORE (GE Healthcare Worldwide, Chicago, IL). In some embodiments, antibodies of the present disclosure may be described in terms of their binding affinity for VSIG-4. In some embodiments, antibodies of the present disclosure include antibodies that interact with an antigen wherein the dissociation constant ($K_D$) is less than or equal to $5\times10^{-6}$ M, less than or equal to $1\times10^{-6}$ M, less than or equal to $5\times10^{-7}$ M, less than or equal to $1\times10^{-7}$ M, less than or equal to $5\times10^{-8}$ M, less than or equal to $1\times10^{-8}$ M, less than or equal to $5\times10^{-9}$ M, less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, less than or equal to $1\times10^{-12}$ M, less than or equal to $5\times10^{-13}$ M, less than or equal to $1\times10^{-13}$ M, less than or equal to $5\times10^{-14}$ M, less than or equal to $1\times10^{-14}$ M, less than or equal to $5\times10^{-15}$ M, or less than or equal to $1\times10^{-15}$ M.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject. As used herein, "isolated" refers to material that has been either removed from its natural environment (for example, the natural environment if it is naturally occurring), produced using recombinant techniques, or chemically or enzymatically synthesized, and thus is altered "by the hand of man" from its natural state.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A. Assay schematic; FIG. 2B. CM5 chips (GE Healthcare Worldwide, Chicago, IL) were covalently coated with Protein A/G/L (Novus Biologicals, Littleton, CO). Fc-tagged Siglec7 protein was captured on the Protein A/G/L chip. The chip was then exposed to varying amounts of soluble his-tagged VSIG-4 recombinant protein to determine the $K_D$ for the binding interaction between the two proteins. The binding affinity was determined to be 29.7 nM.

μg/mL of rhSiglec-7/Fc protein was used. The percentage shown in the upper right quadrant indicates the level of interaction.

Figure 6A:
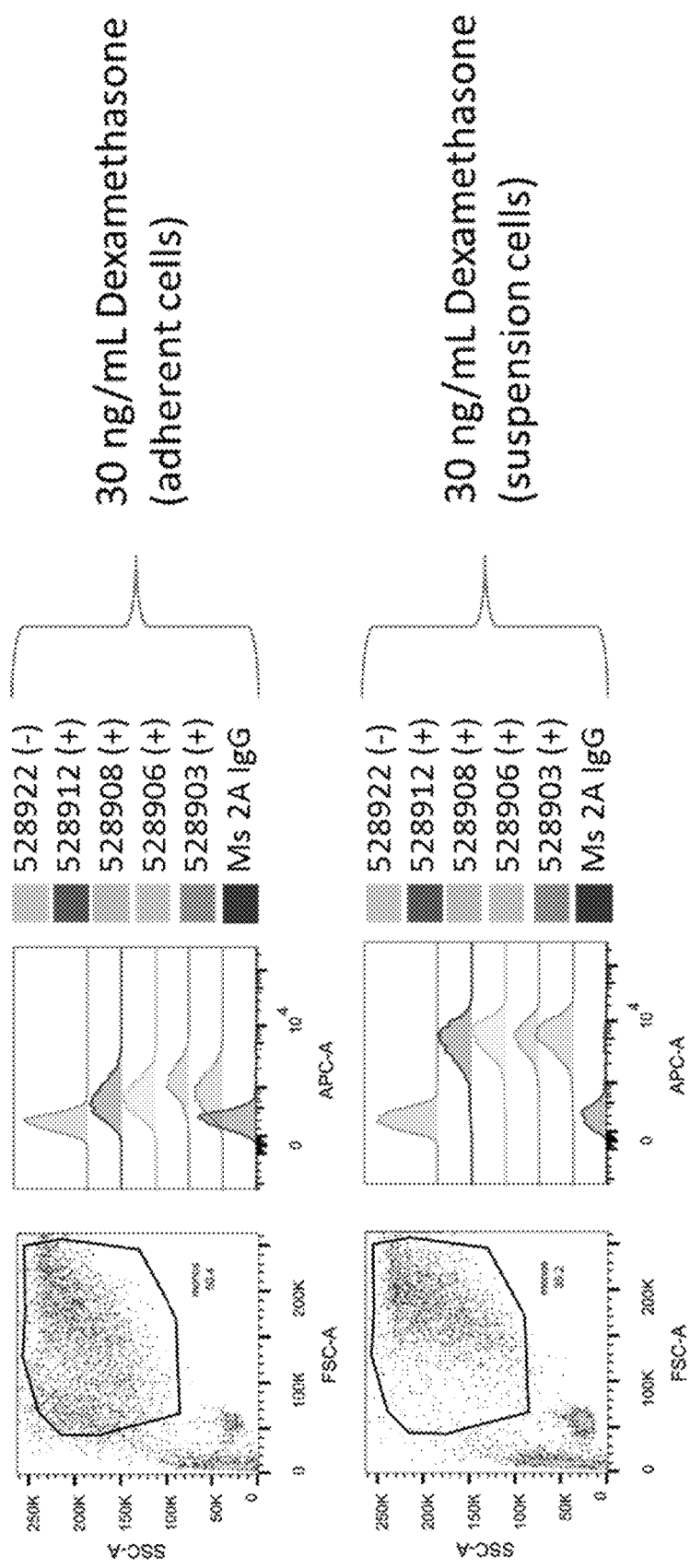
Figure 6B:
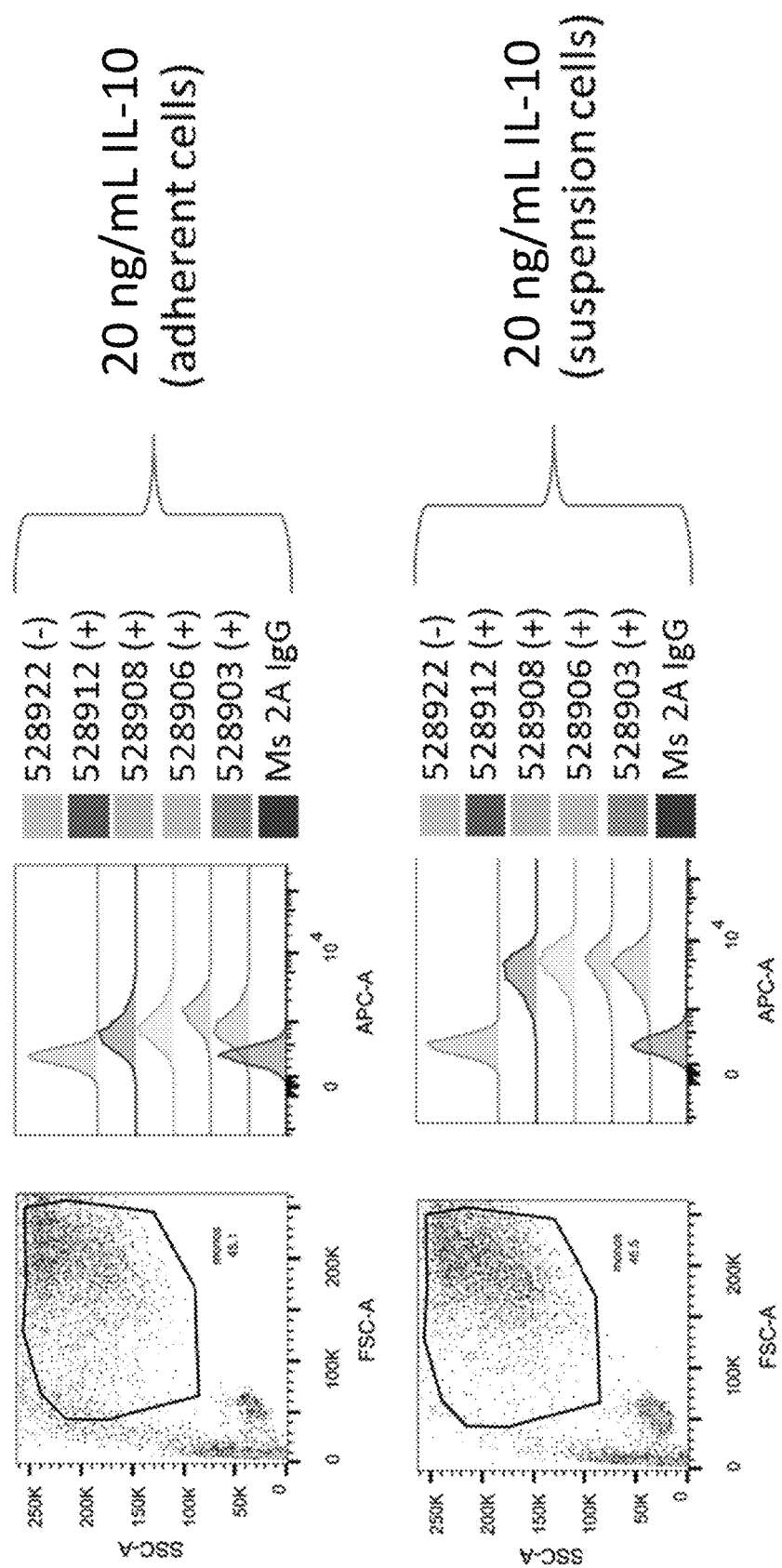

FIG. 6A-FIG. 6B shows VSIG-4 is expressed on M2c monocytes polarized with either 30 ng/mL Dexamethasone for 3 days (FIG. 6A) or 20 ng/mL IL-10 for 3 days (FIG. 6B). M2c cells were polarized as described in Example 3. Ms x hVSIG4 528903.111 ("528903"), Ms x hVSIG4 528906.11 ("528906"), Ms x hVSIG4 528908.11 ("528908"), Ms x hVSIG4 528912.11 ("528912"), and Ms x hVSIG4 528922.111 ("528922") are mouse anti-human VSIG-4 antibody-expressing clones. Histograms shown were gated on CD14$^+$ Zombie Violet® cells.

Figure 7:
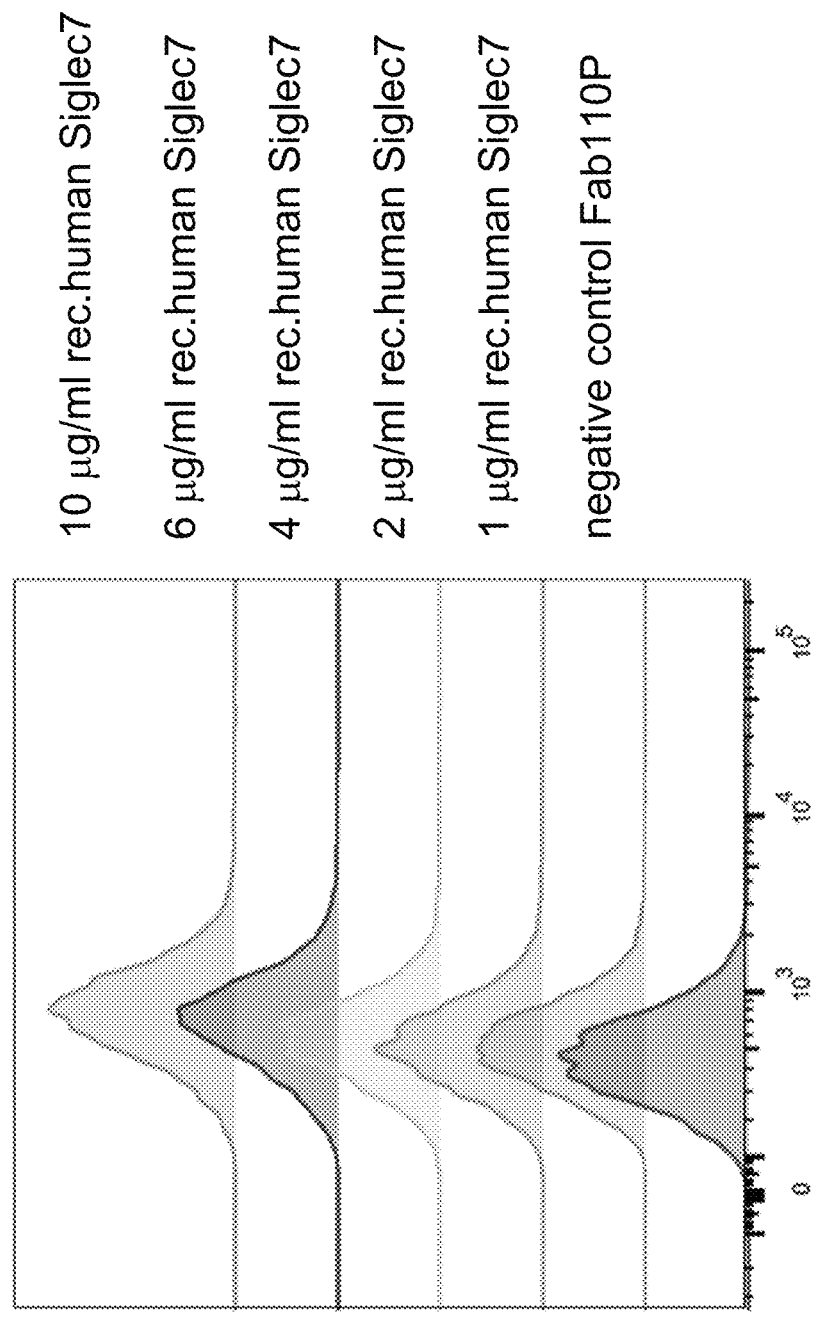

FIG. 7 shows detection of Siglec-7/VSIG-4 interaction in primary M2c polarized cells. Polarized M2c cells were incubated with the indicated amounts of human Siglec-7 Fc protein (1 μg/mL to 10 μg/mL) or a negative control (FAB110P) for 30 minutes at room temperature. An anti-Fc PE detection antibody was added for another 20 minutes. The cells were then washed, stained with anti-VSIG4 Alexa Fluor 647 and anti-CD14 FITC for 30 minutes. The cells were then washed with RDFII staining buffer and analyzed on a LSRII Fortessa flow cytometer (BD Biosciences, San Jose, CA).

Figures 8B, 8C:
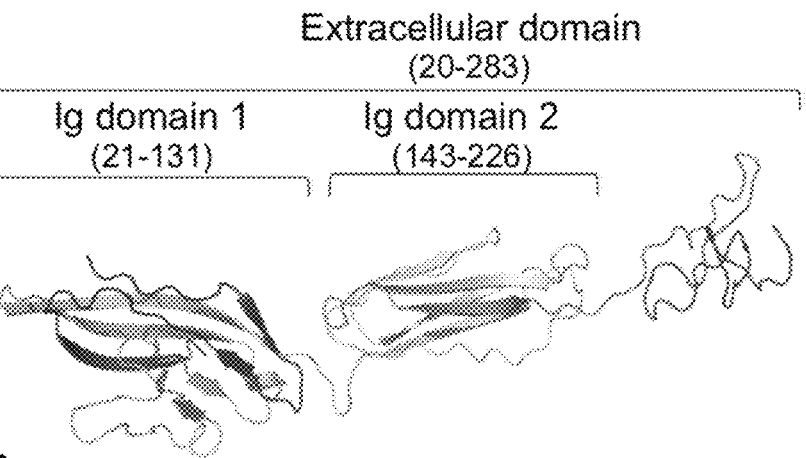
Figure 8A:
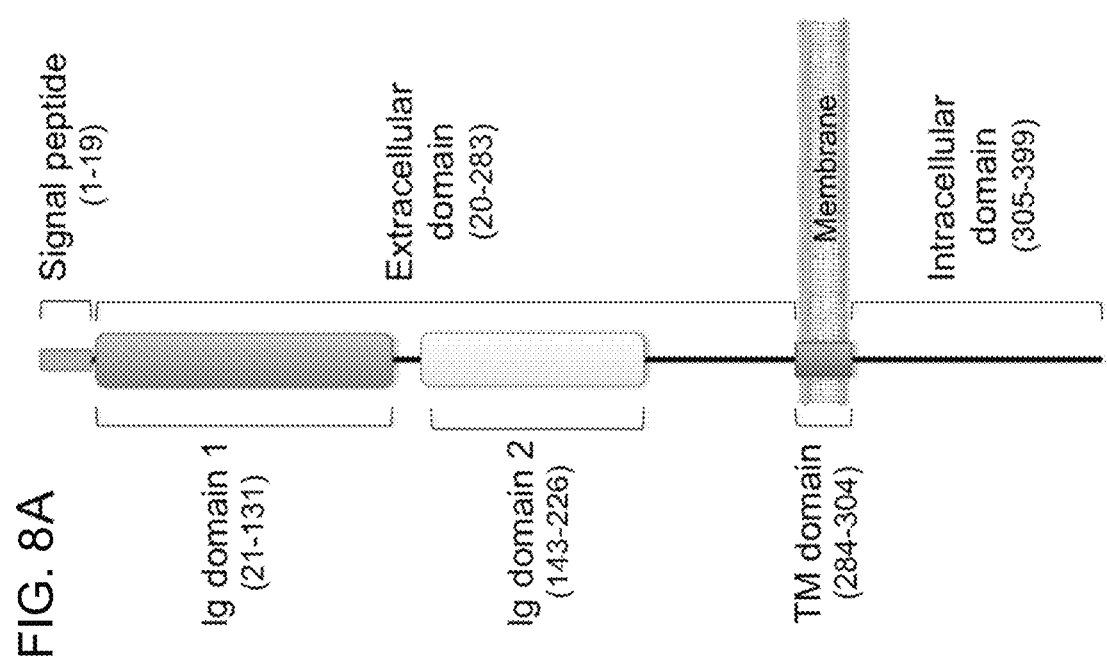

FIG. 8A-FIG. 8C show representations of the architecture and structure of VSIG-4. FIG. 8A. VSIG-4 is a member of the immunoglobulin superfamily; this type I transmembrane receptor contains a 19 amino acid signal peptide followed by the extracellular domain (residues 20-283), a transmembrane domain (residues 284-304), and intracellular domain (residues 305-399), where the residue numbers correspond to Uniprot number: Q9Y279. The extracellular domain of VSIG-4 is comprised of two tandem Ig domains followed by a ~60 residue juxtamembrane sequence. FIG. 8B. The structure of the N-terminal VSIG-4 Ig domain (PDB ID 2icc) shows an exemplary V-type Ig domain, the domain of VSIG-4 responsible for binding to C3b/iC3b. FIG. 8C. A structural prediction of the VSIG-4 ectodomain shows the tandem Ig domain structure followed by an unstructured ~60 residue juxtamembrane region.

FIG. 9A-FIG. 9D shows Siglec7 binds to glycosylated VSIG-4. FIG. 9A. Purified recombinant human VSIG-4 ectodomain (rhVSIG4) expressed in NS0 cells was subjected to deglycosylation with an enzyme cocktail and separated by SDS-PAGE and visualized by silver stain. FIG. 9B-FIG. 9D. Recombinant human Siglec7-Fc (rhSiglec7-Fc) was captured on a Biacore CM5 chip modified with Protein A/G/L at ~700 RU capture density and tested for binding with fully glycosylated rhVSIG4 (FIG. 9B), deglycosylated VSIG-4 (FIG. 9C), and CD56/NCAM (FIG. 9D) at concentrations ranging between 0.5 nM and 500 nM.

FIG. 10A-FIG. 10D show Rt x hVSIG4 489517.111 specifically binds the VSIG-4 polypeptide regardless of glycosylation state as demonstrated by Biacore. Blocking antibody (Rt x hVSIG4 489517.111) was captured on a Protein A/G/L chip at ~350 RU and tested for binding to mammalian NS0 cell-derived rhVSIG4 (FIG. 10A), mammalian derived and fully deglycosylated rhVSIG4 (FIG. 10B), E. coli derived and free of glycosylation VSIG-4 (FIG. 10C), and CD56/NCAM, a heavily glycosylated protein (FIG. 10D). All analyte proteins, rhVSIG4 and CD56/NCAM were tested at concentrations ranging between 25 pM and 250 nM. That Rt x hVSIG4 489517.111 binds VSIG-4 regardless of VSIG-4's glycosylation state and not to CD56/NCAM, a heavily glycosylated molecule with a similar glycoprofile as VSIG4, demonstrates the specificity of the Rt x hVSIG4 489517.111 to the VSIG-4 polypeptide and shows that Rt x hVSIG4 489517.111 is not anti-glycosylation specific.

FIG. 11A-FIG. 11D show Ms x hVSIG4 528906.11 specifically binds the VSIG-4 polypeptide regardless of glycosylation state as demonstrated by Biacore. Ms x hVSIG4 528906.11 was captured on a Protein A/G/L chip at ~350 RU and tested for binding to mammalian NS0 cell-derived rhVSIG4 (FIG. 11A), mammalian derived and fully deglycosylated rhVSIG4 (FIG. 11B), E. coli derived and free of glycosylation VSIG-4 (FIG. 11C), and CD56/NCAM, a heavily glycosylated protein (FIG. 11D). All analyte proteins, rhVSIG4, and CD56/NCAM were tested at concentrations ranging between 25 pM and 250 nM. That Ms x hVSIG4 528906.11 binds VSIG4 regardless of VSIG4's glycosylation state and not to CD56/NCAM, a heavily glycosylated molecule with a similar glycoprofile as VSIG4, demonstrates the specificity of Ms x hVSIG4 528906.11 to the VSIG4 polypeptide and shows that Ms x hVSIG4 528906.11 is not anti-glycosylation specific.

FIG. 12A-FIG. 12D show Ms x hVSIG4 528908.11 specifically binds the VSIG-4 polypeptide regardless of glycosylation state as demonstrated by Biacore. Ms x hVSIG4 528908.11 was captured on a Protein A/G/L chip at ~350 RU and tested for binding to mammalian NS0 cell-derived rhVSIG4 (FIG. 12A), mammalian derived and fully deglycosylated rhVSIG4 (FIG. 12B), E. coli derived and free of glycosylation VSIG-4 (FIG. 12C), and CD56/NCAM, a heavily glycosylated protein (FIG. 12D). All analyte proteins, rhVSIG4 and CD56/NCAM were tested at concentrations ranging between 25 pM and 250 nM. That the antibody binds VSIG4 regardless of its glycosylation state and not to CD56/NCAM, a heavily glycosylated molecule with a similar glycoprofile as VSIG4, demonstrates the specificity of Ms x hVSIG4 528908.11 to the VSIG4 polypeptide and shows that Ms x hVSIG4 528908.11 is not anti-glycosylation specific.

FIG. 13A-FIG. 13D show Ms x hVSIG4 528912.11 specifically binds the VSIG-4 polypeptide regardless of glycosylation state as demonstrated by Biacore. Ms x hVSIG4 528912.11 was captured on a Protein A/G/L chip at ~350 RU and tested for binding to mammalian NS0 cell-derived rhVSIG4 (FIG. 13A), mammalian derived and fully deglycosylated rhVSIG4 (FIG. 13B), E. coli derived and free of glycosylation VSIG-4 (FIG. 13C), and CD56/NCAM, a heavily glycosylated protein (FIG. 13D). All analyte proteins, rhVSIG4 and CD56/NCAM were tested at concentrations ranging between 25 pM and 250 nM. That Ms x hVSIG4 528912.11 binds VSIG4 regardless of VSIG4's glycosylation state and not to CD56/NCAM, a heavily glycosylated molecule with a similar glycoprofile as VSIG4, demonstrates the specificity of Ms x hVSIG4 528912.11 to the VSIG4 polypeptide and shows that Ms x hVSIG4 528912.11 is not anti-glycosylation specific.

Figure 14:
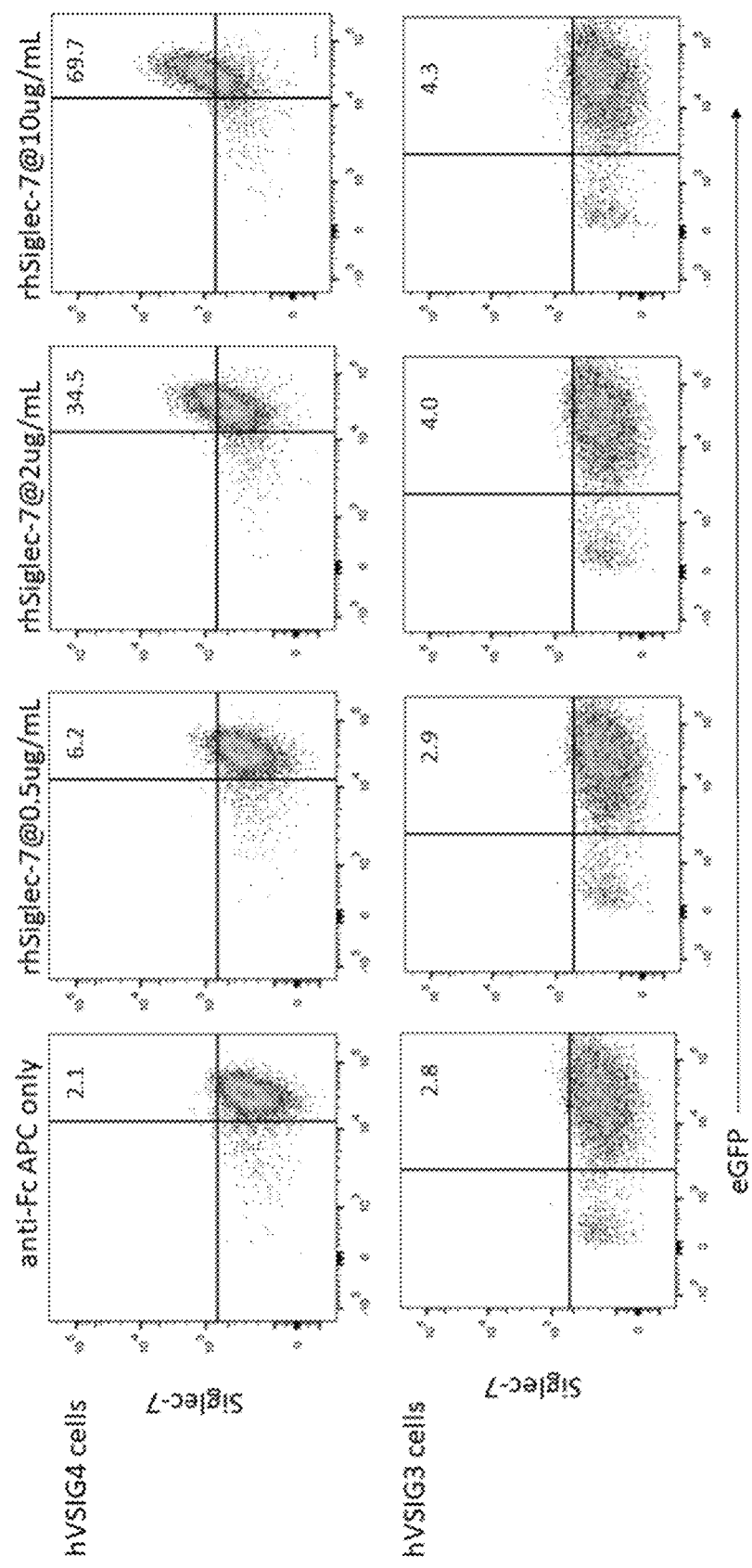
Figure 15B:
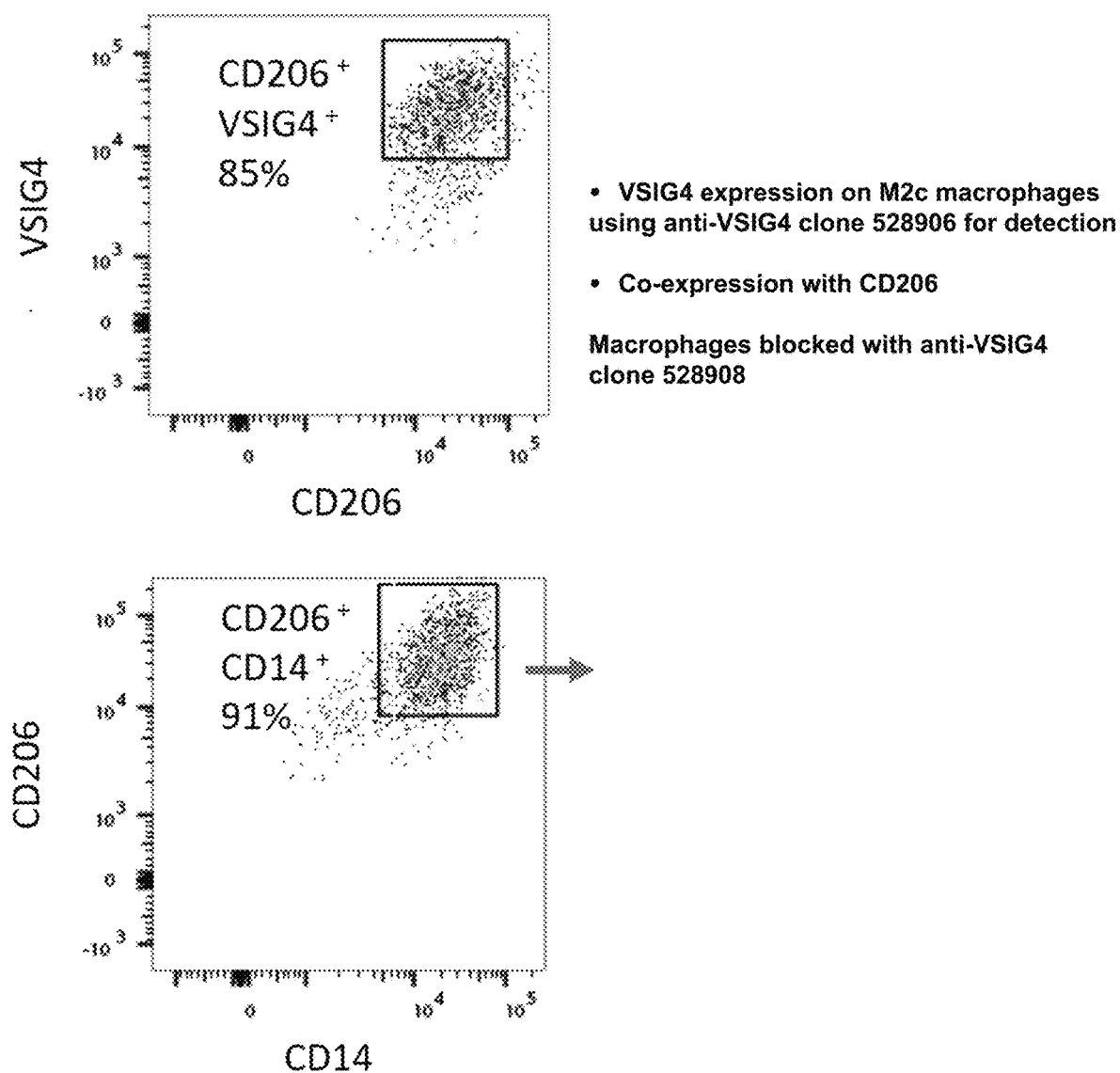
Figure 15C:
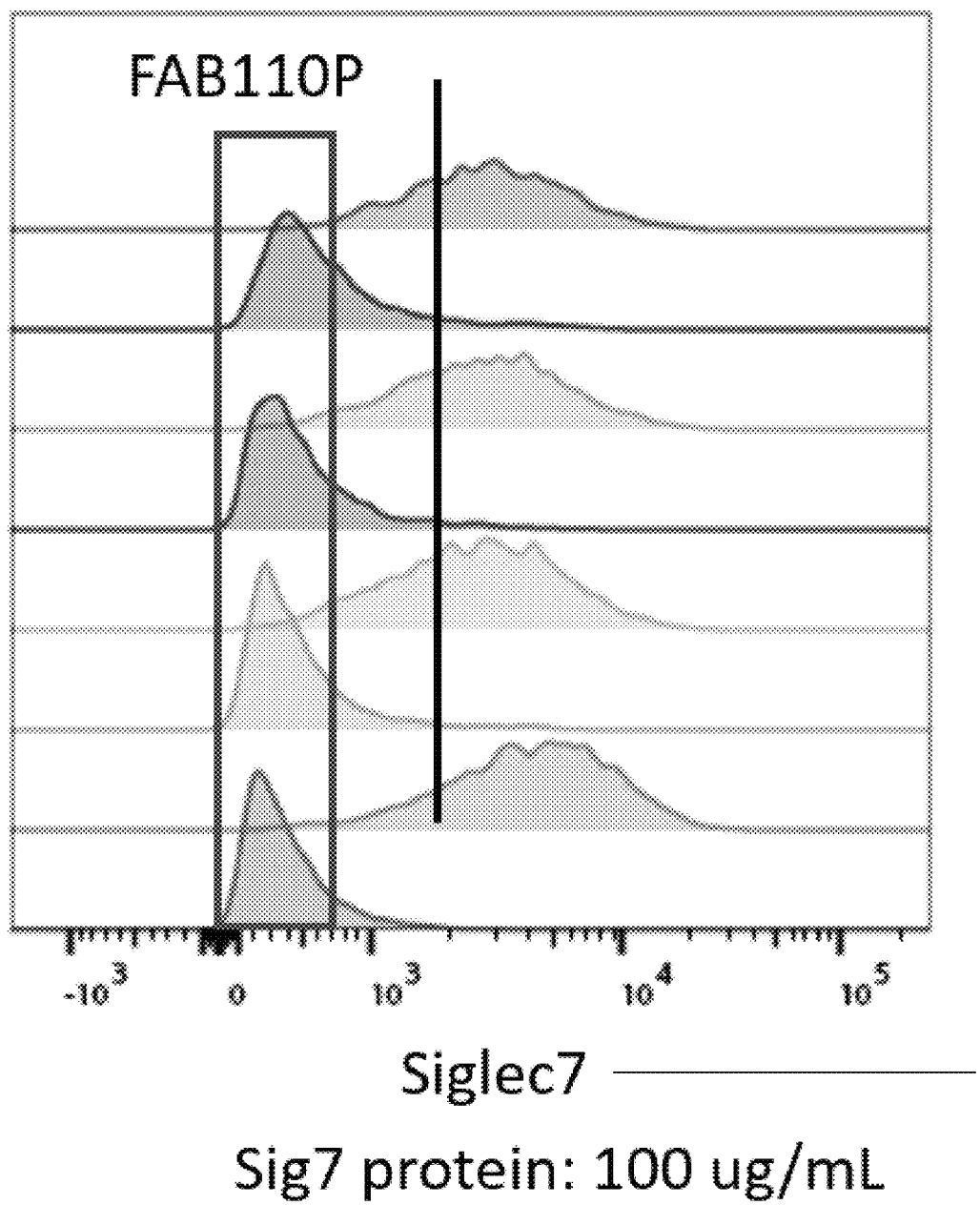
Figure 15D:
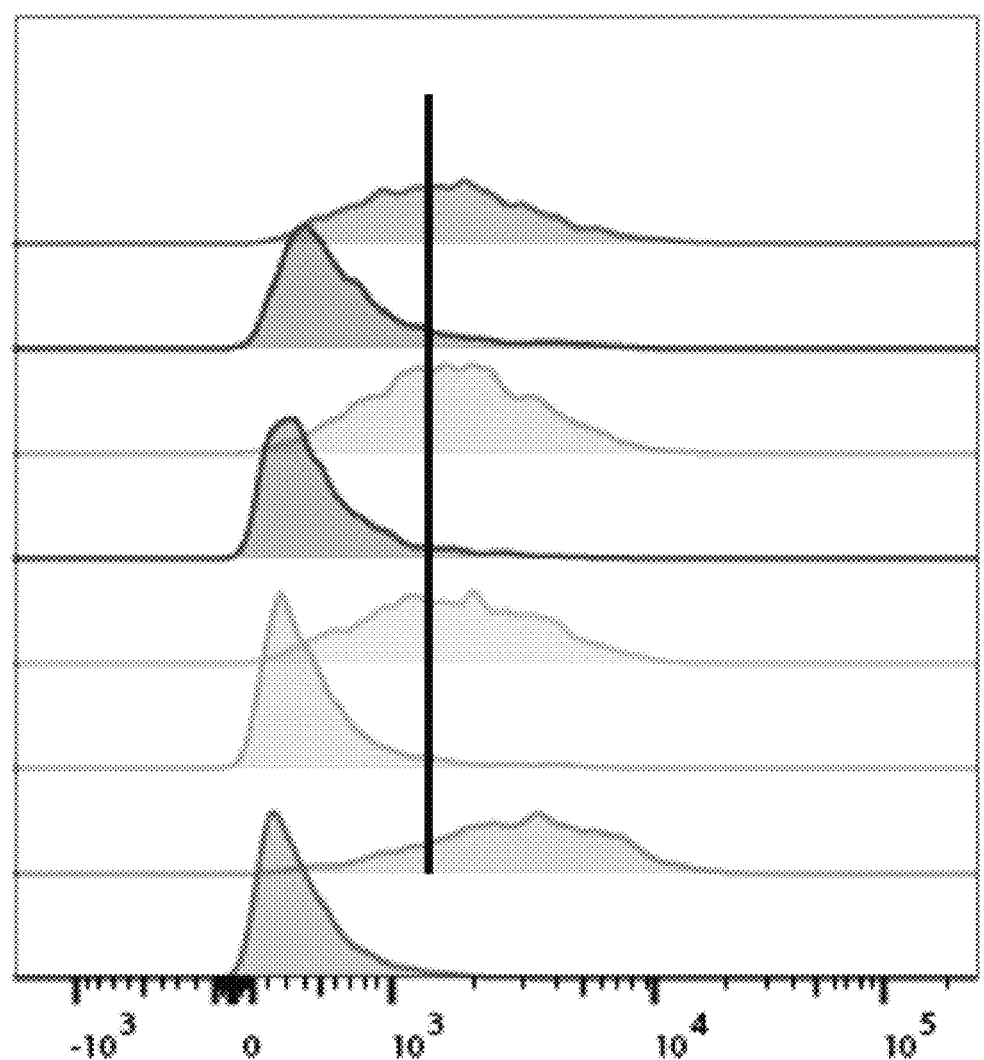
Figure 15E:
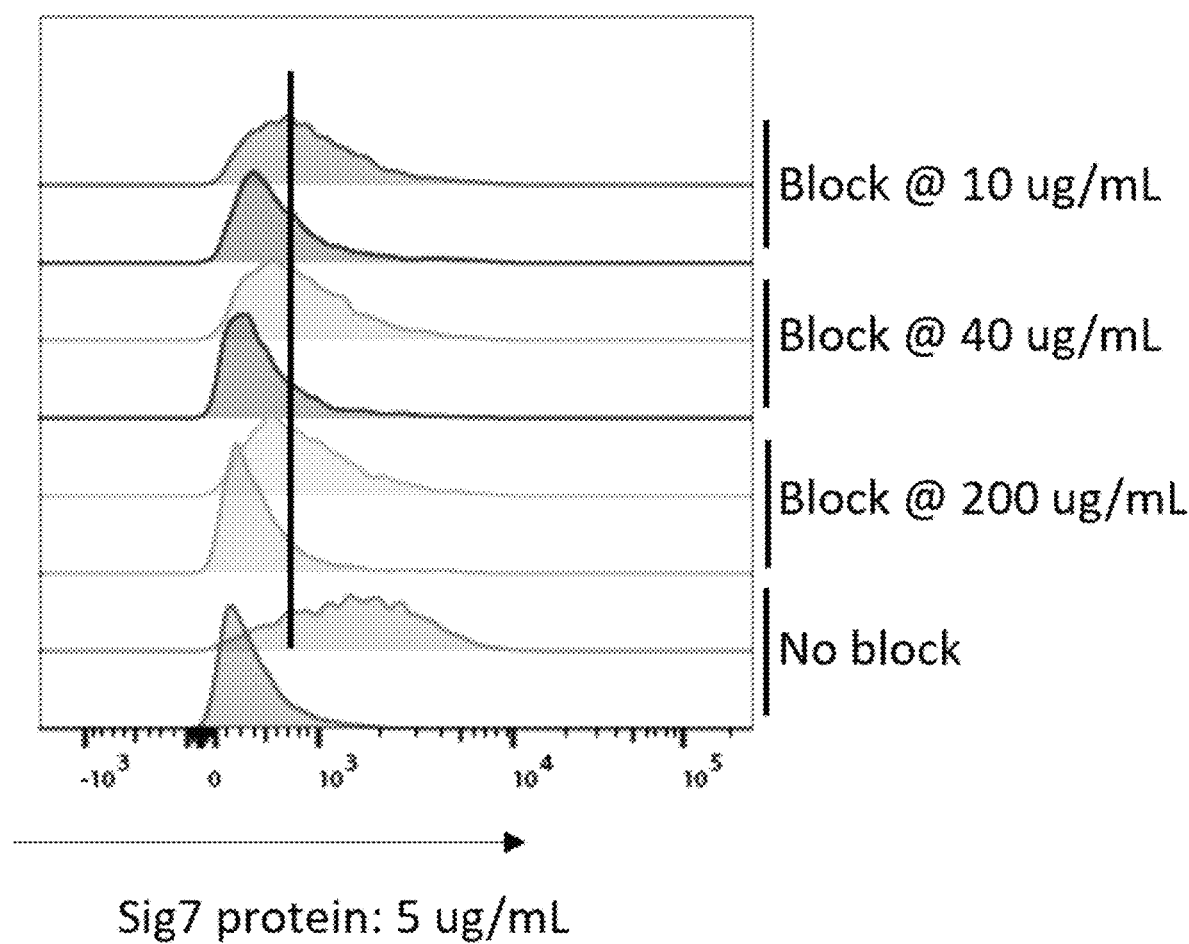
Figures 16A, 16J:
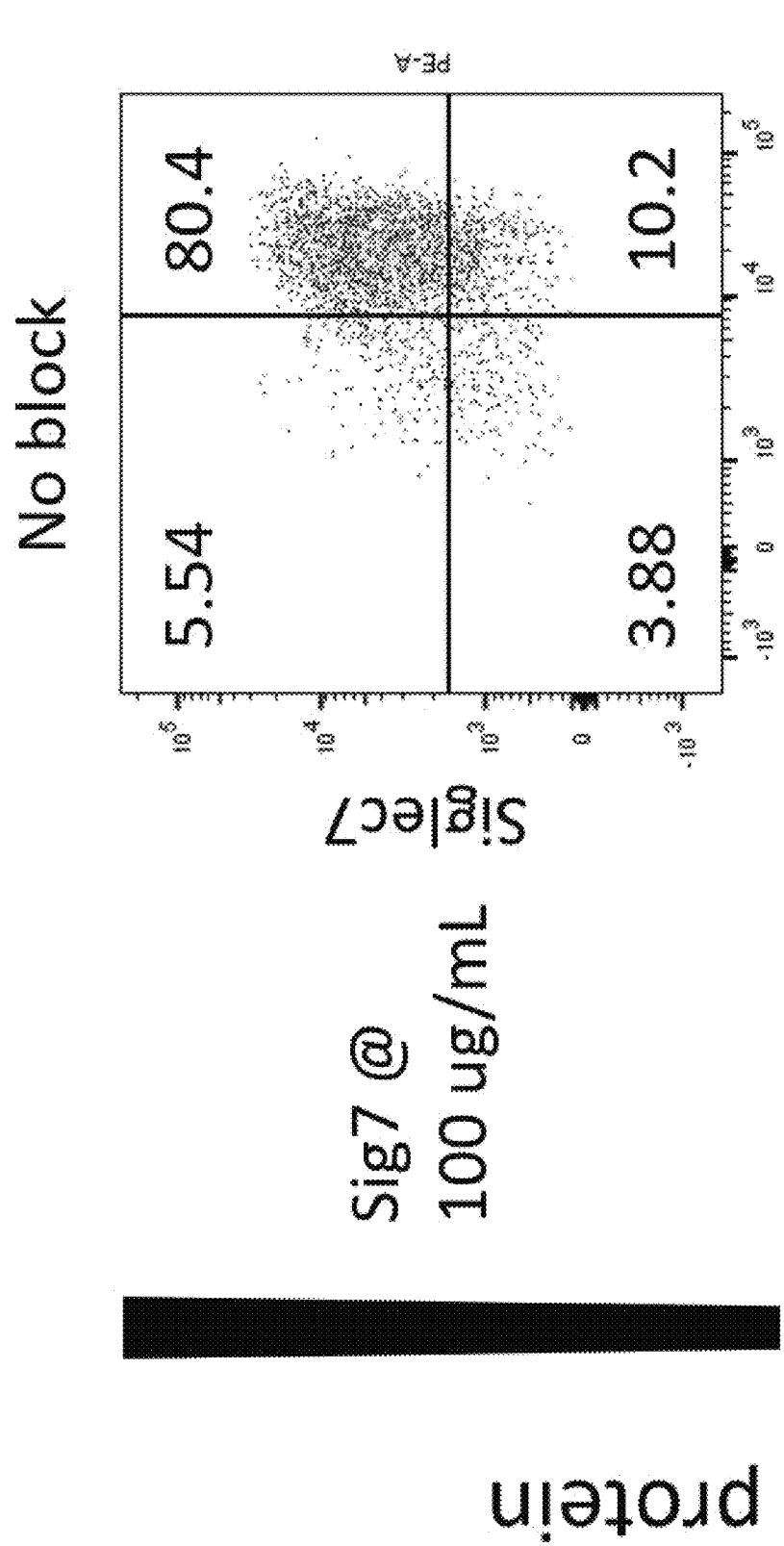
Figure 16C:
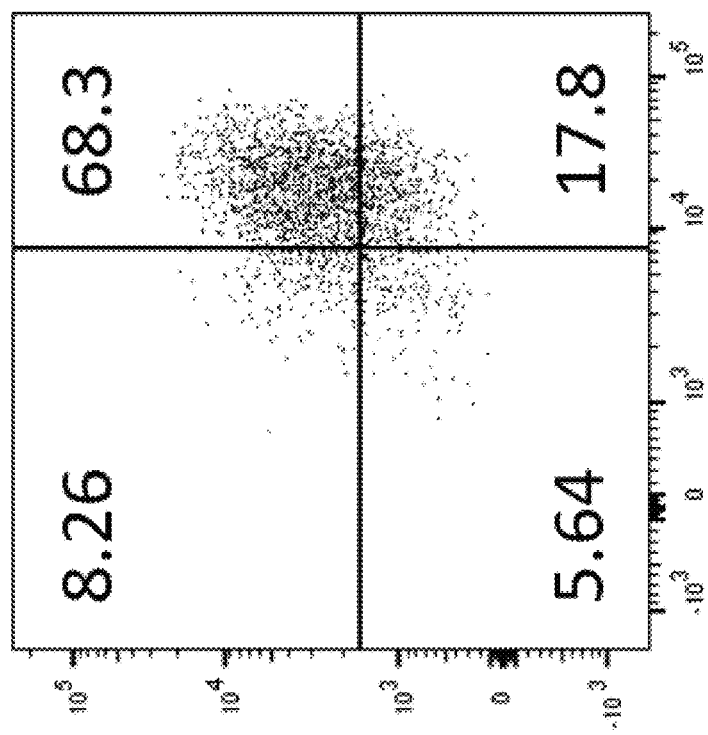
Figure 16D:
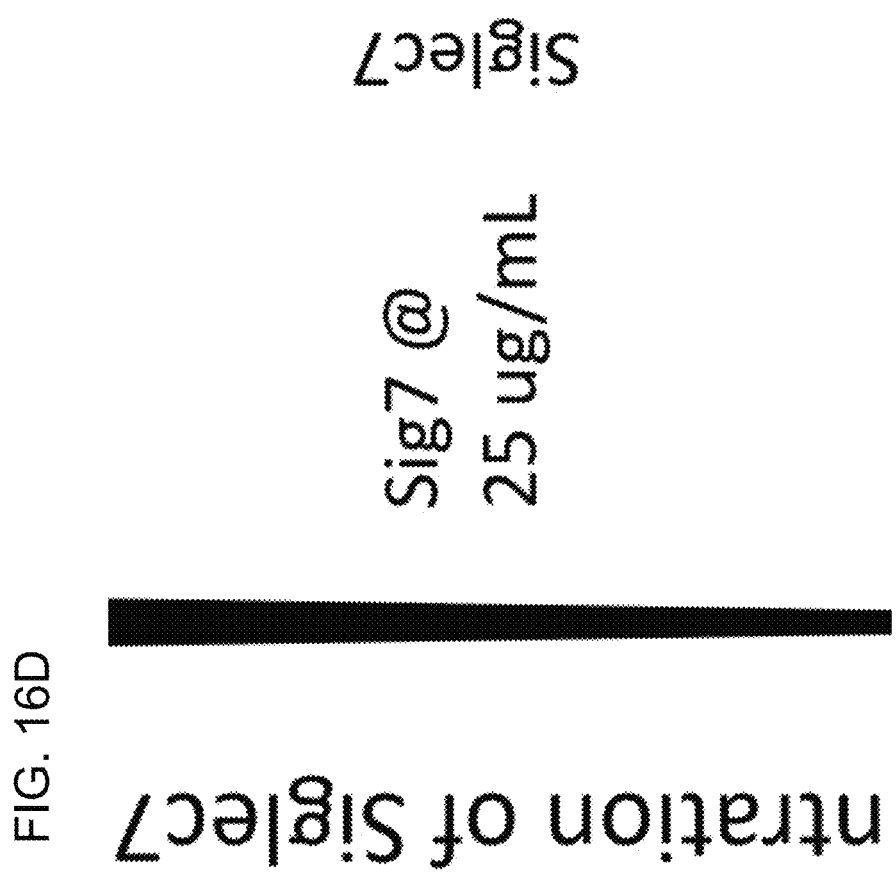
Figure 16E:
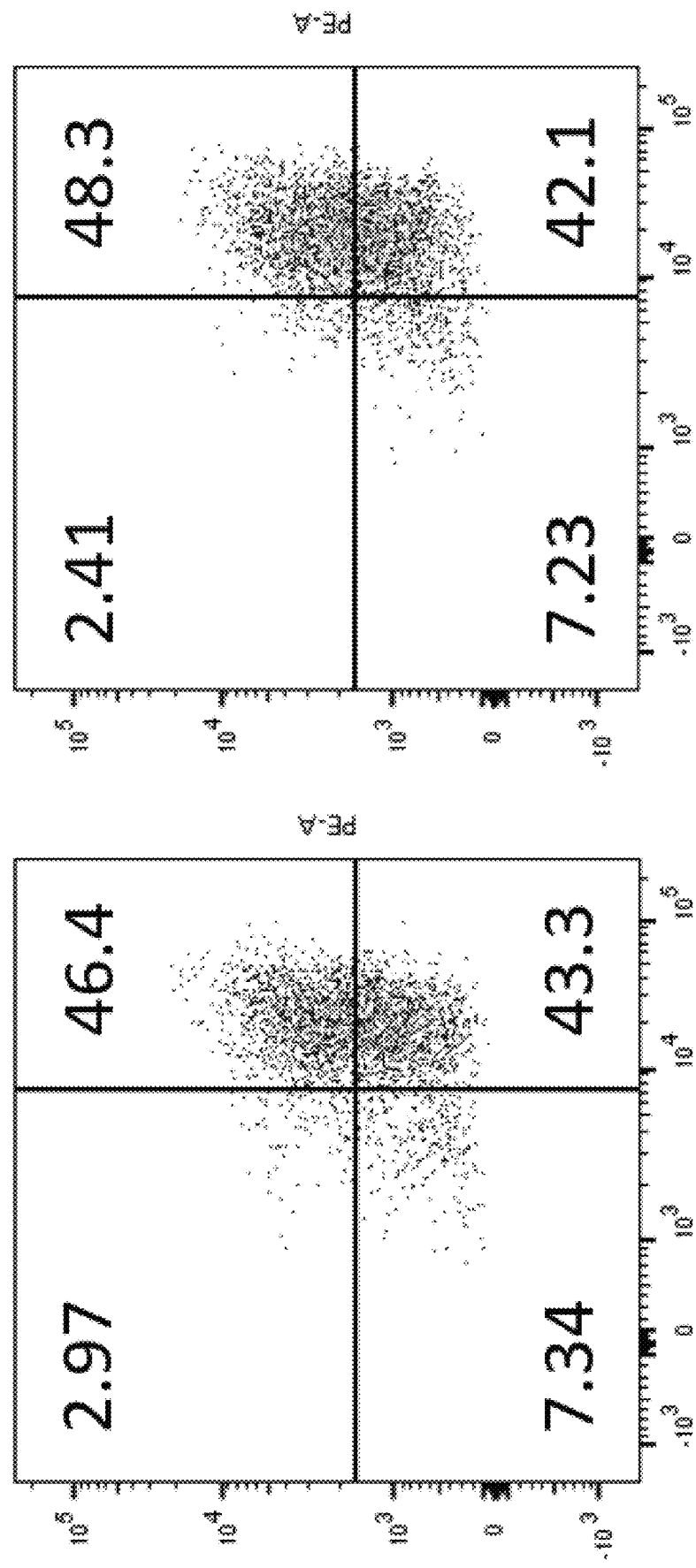
Figure 16F:
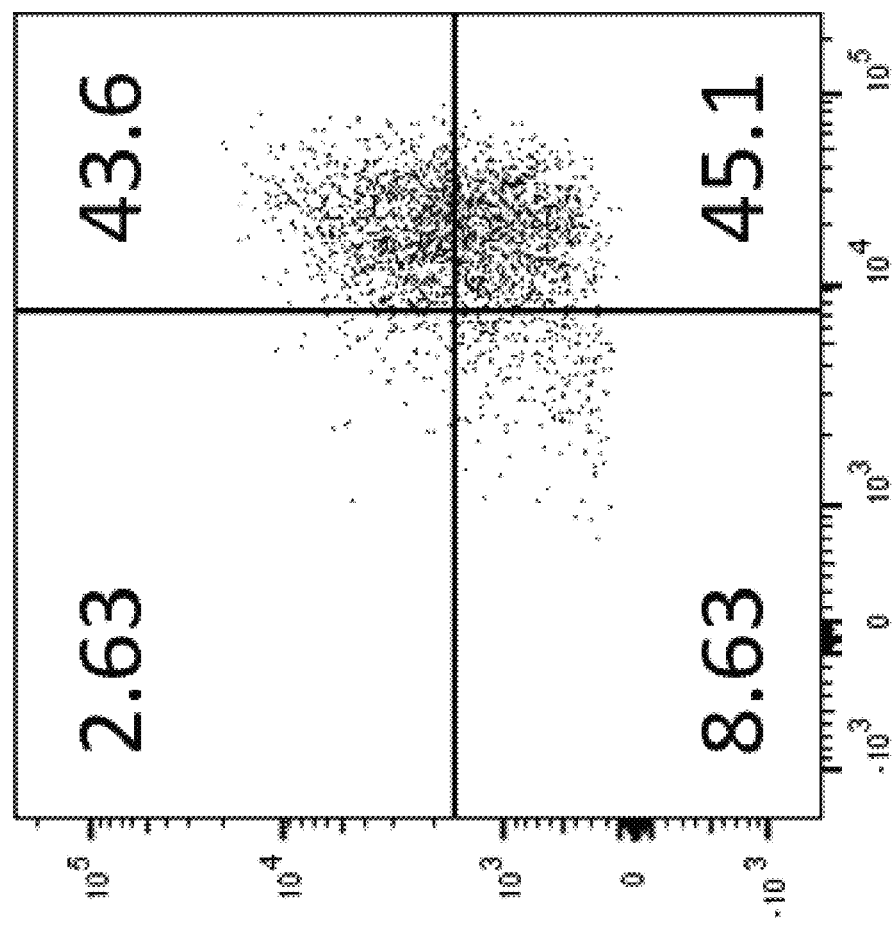
Figure 16G:
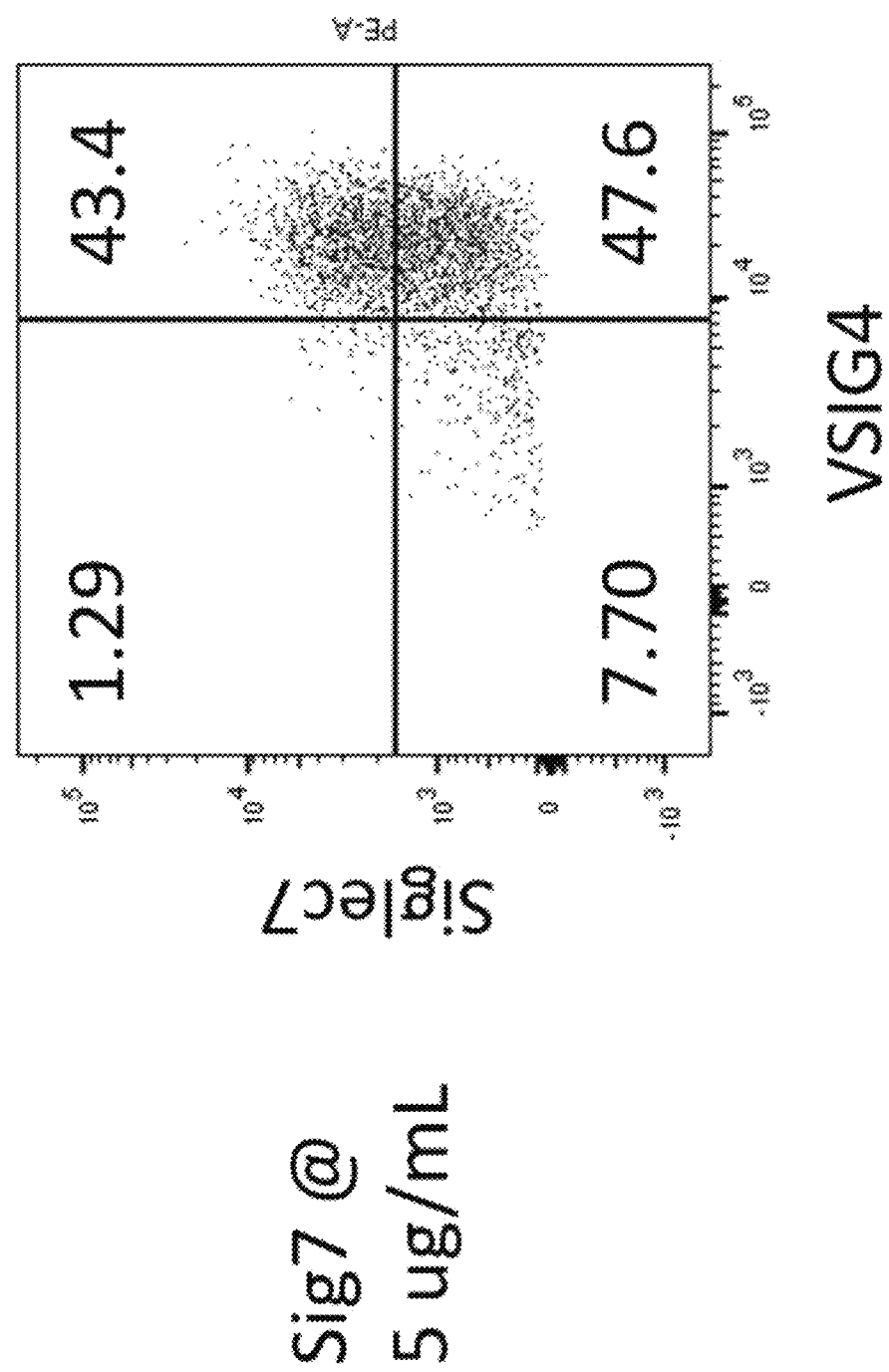
Figure 16H:
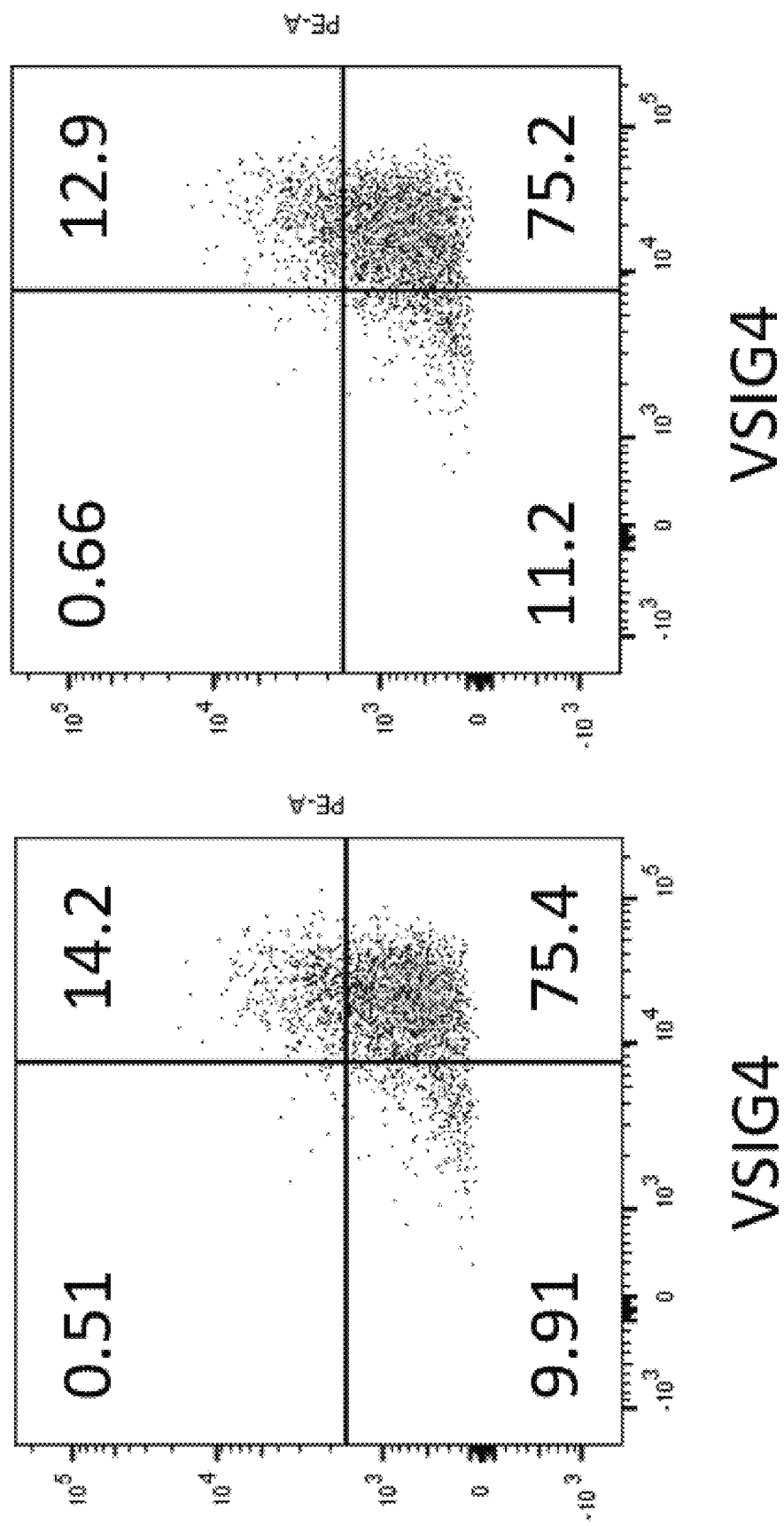
Figure 16I:
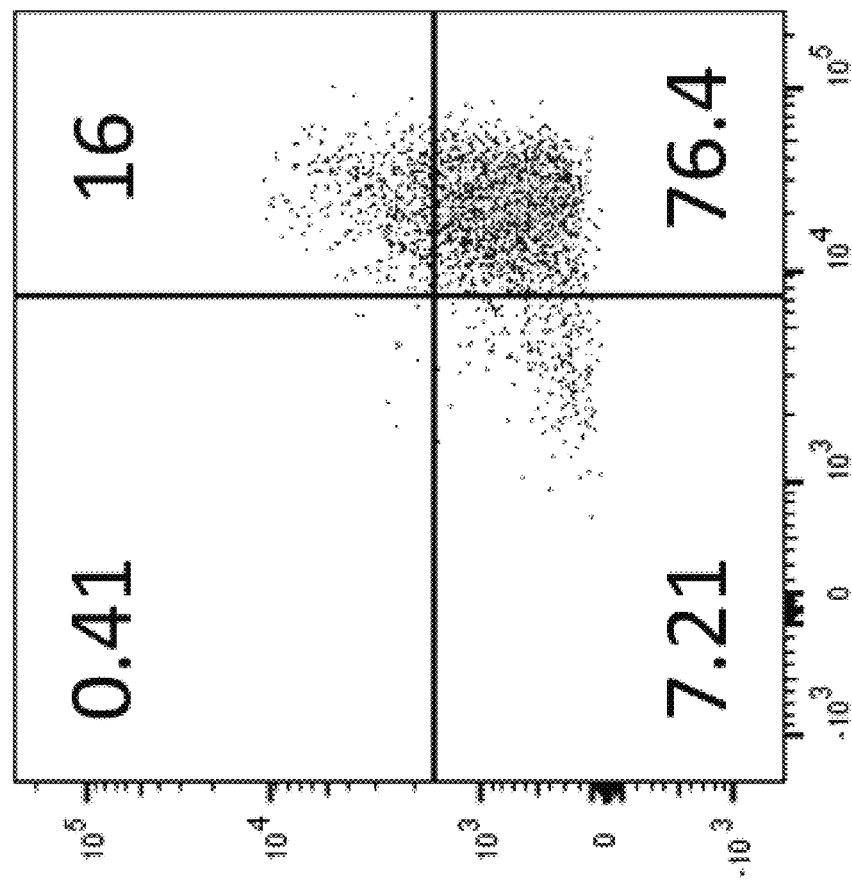
Figure 17C:
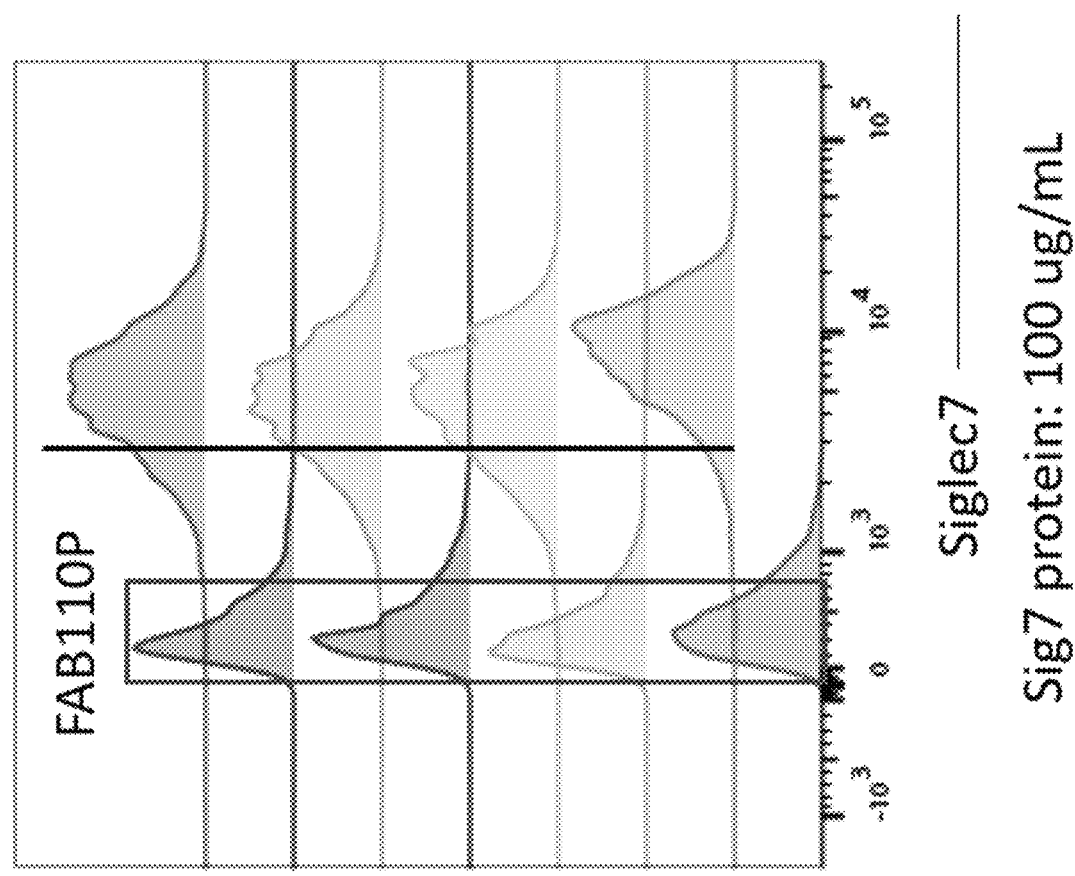
Figure 17D:
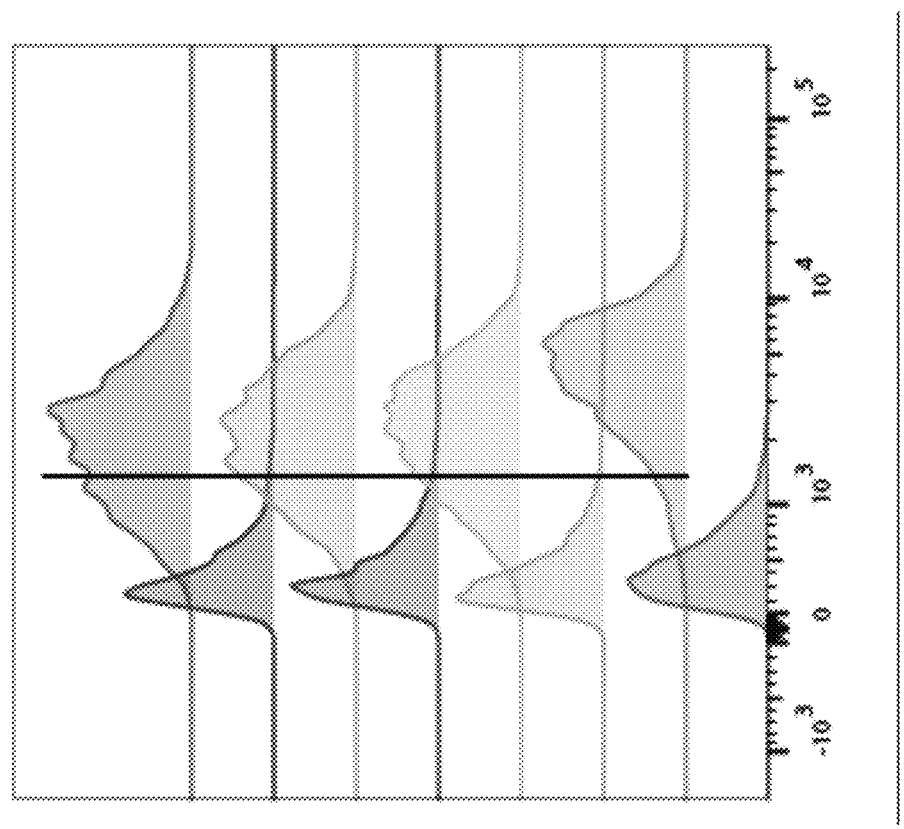
Figures 18A, 18J:
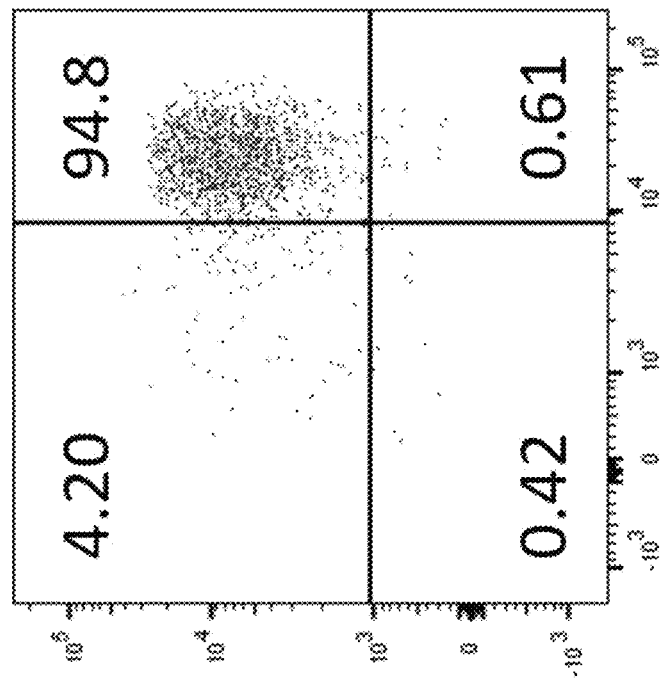
Figure 18B:
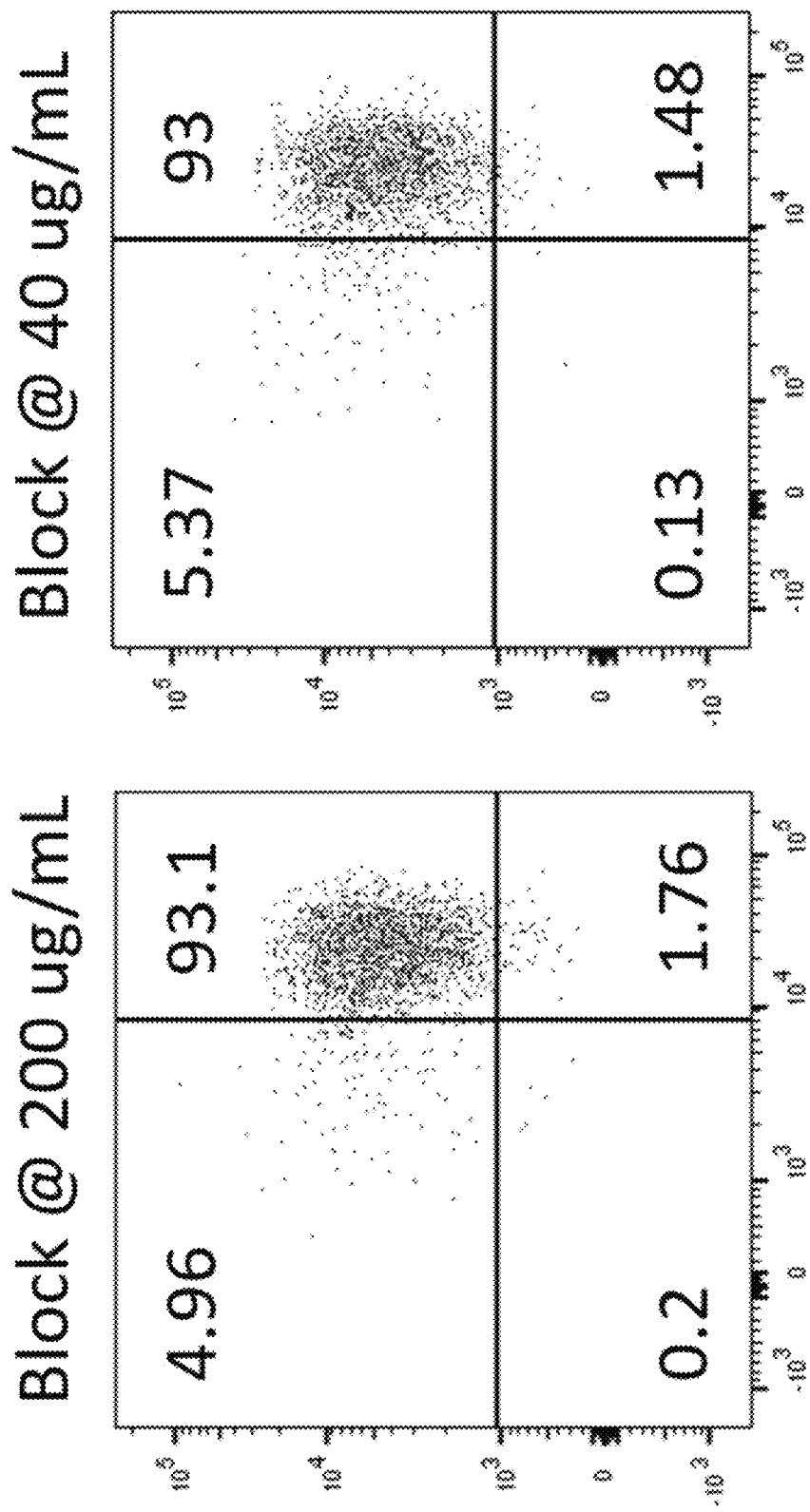
Figure 18C:
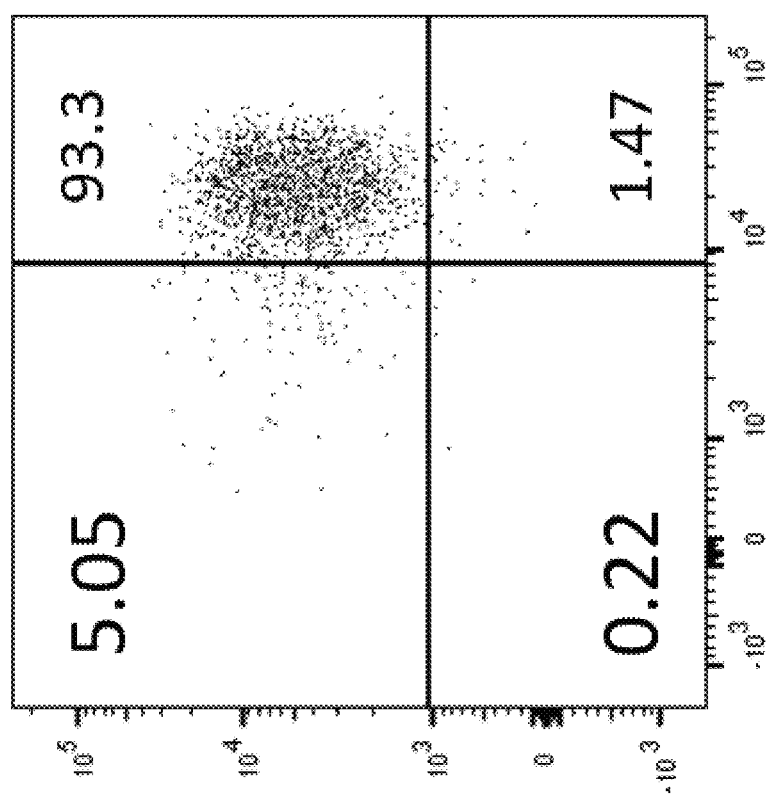
Figure 18F:
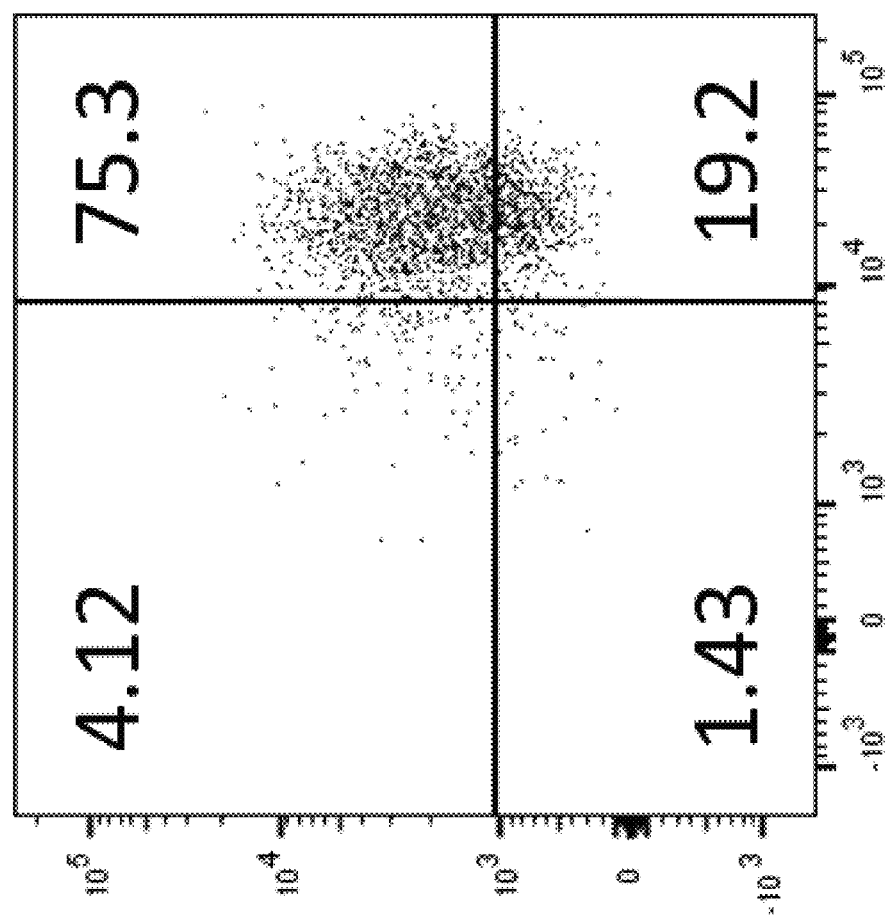
Figure 18G:
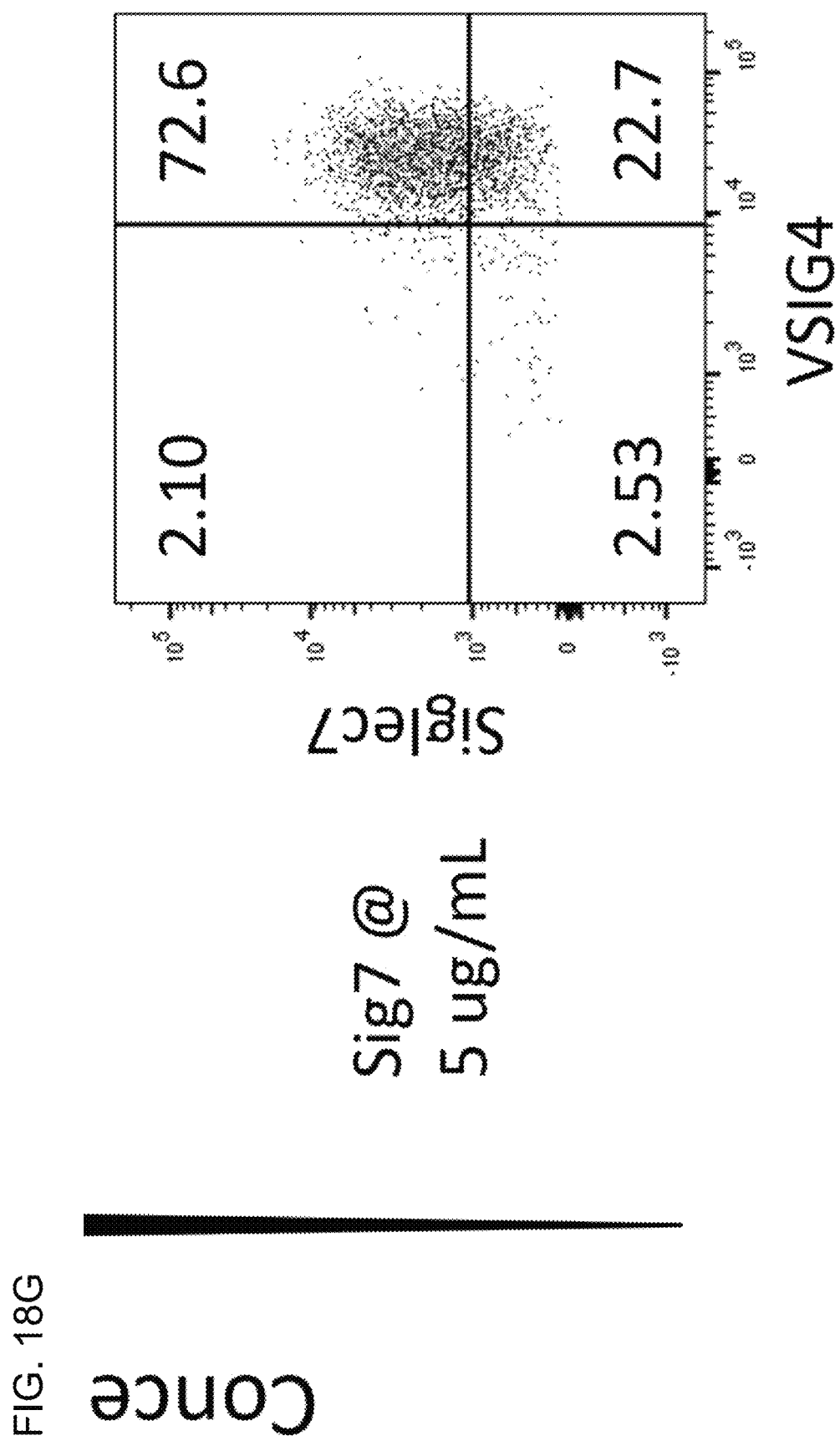
Figure 18H:
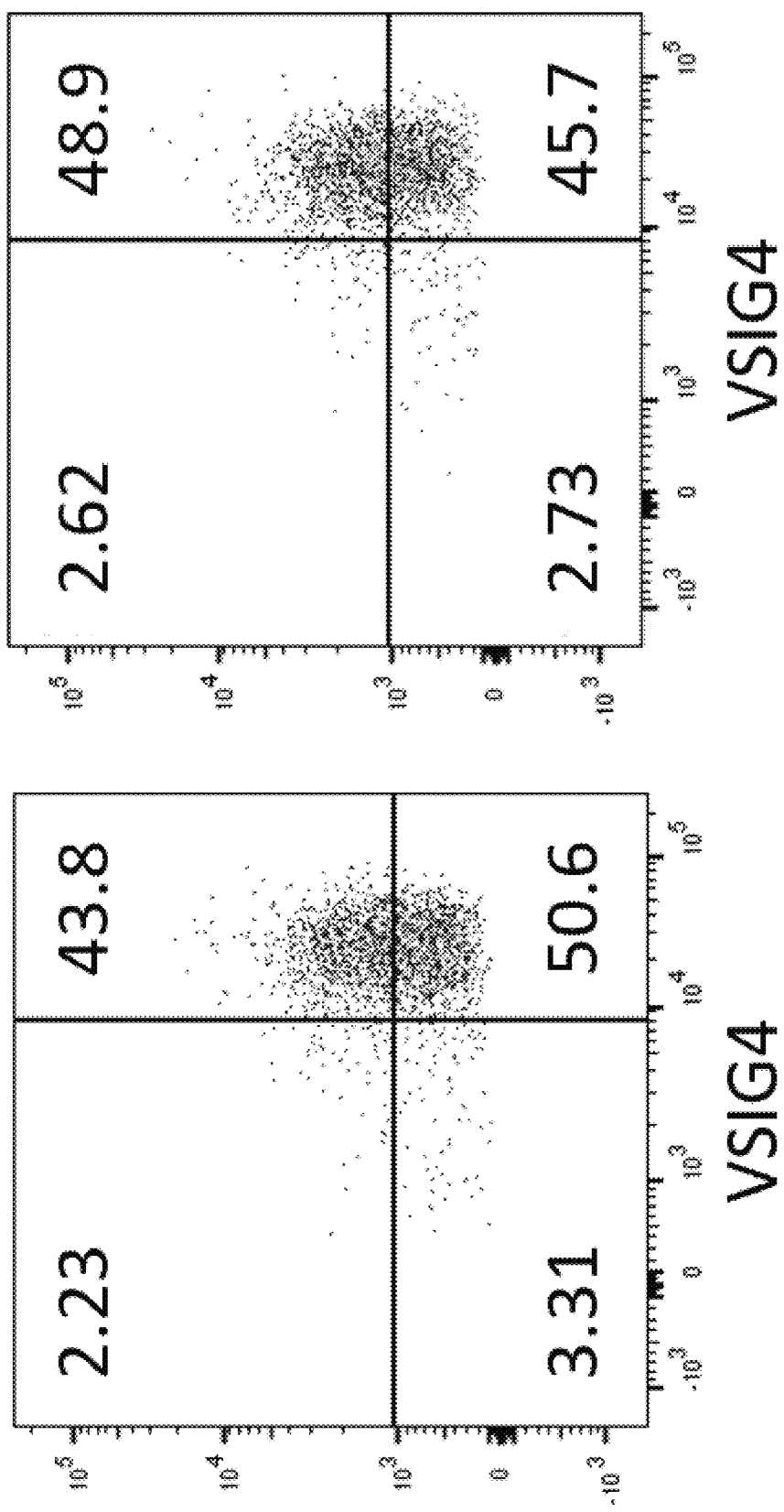
Figure 18I:
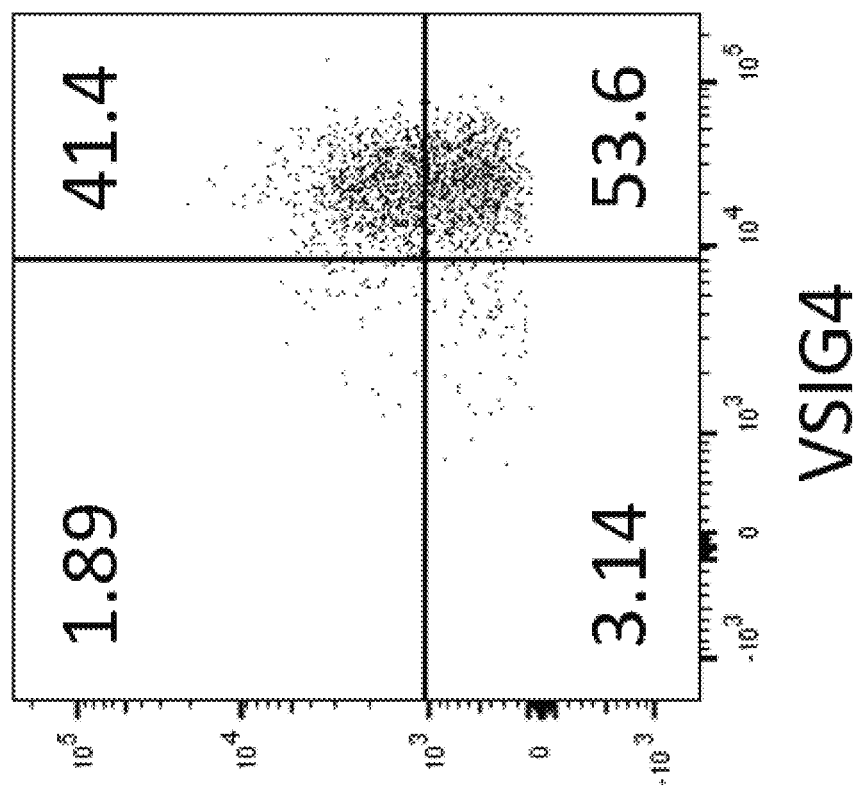

FIG. 14 shows that recombinant human Siglec-7 binds specifically to HEK293 cells transfected with recombinant human VSIG-4 fused to eGFP in a dose-dependent manner but recombinant human Siglec-7 does not bind to the same cell type transfected with recombinant human VSIG3-eGFP.

FIG. 15A-FIG. 15E show a representative anti-human VSIG-4 antibody blocks the interaction of VSIG-4 with recombinant human Siglec-7/Fc on adherent M2c macrophages polarized with Dexamethasone (adherent cells). M2c macrophages were incubated with Ms x hVSIG4 528908.11 at 10 μg/mL, 40 μg/mL or 200 μg/mL to test the antibody's capacity to block the interaction with rhSiglec-7 at 100 μg/mL, 25 μg/mL or 5 μg/mL. Histograms were gated on CD14⁺ CD206⁺ cells. FIG. 15A-FIG. 15E form a complete figure, as shown in the index figure, FIG. 15F.

FIG. 16A-FIG. 16I show representative dot plots of histograms shown in FIG. 15 of Ms x hVSIG4 528908.11 and recombinant human Siglec-7 titration. Data shown are gated on CD14⁺ and CD206⁺ cells. FIG. 16A-FIG. 16I form a complete-figure, as shown in the index figure, FIG. 16J.

FIG. 17A-FIG. 17E show a representative anti-human VSIG-4 antibody blocks the interaction of VSIG-4 with recombinant human Siglec-7/Fc on suspension M2c macrophages polarized with Dexamethasone (suspension cells). M2c macrophages were incubated with Ms x hVSIG4 528908.11 at 10 µg/mL, 40 µg/mL or 200 µg/mL to test the antibody's capacity to block the interaction with rhSiglec-7 at 100 µg/mL, 25 µg/mL or 5 µg/mL. Histograms were gated on CD14⁺ CD206⁺ cells. FIG. 17A-FIG. 17E form a complete figure, as shown in the index figure, FIG. 17F.

FIG. 18A-FIG. 18I show representative dot plots of histograms shown in FIG. 17 of Ms x hVSIG4 528908.11 and recombinant human Siglec-7 titration. Data shown are gated on CD14⁺ and CD206⁺ cells. FIG. 18A-FIG. 18I form a complete figure, as shown in the index figure, FIG. 18J.

Figure 19A:
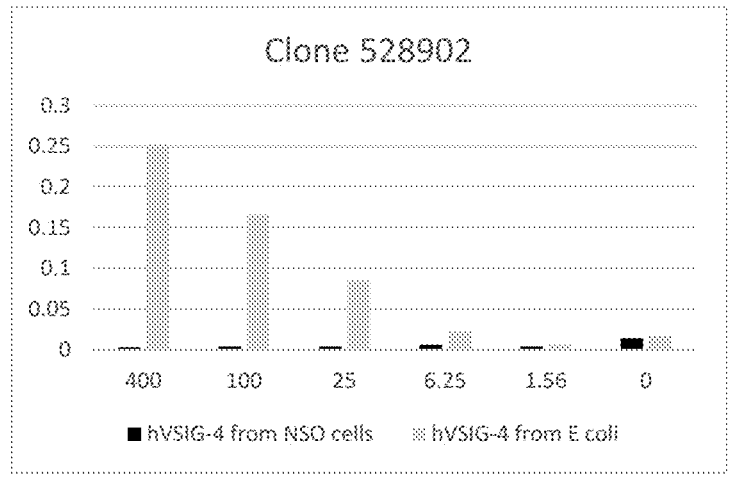
Figure 19B:
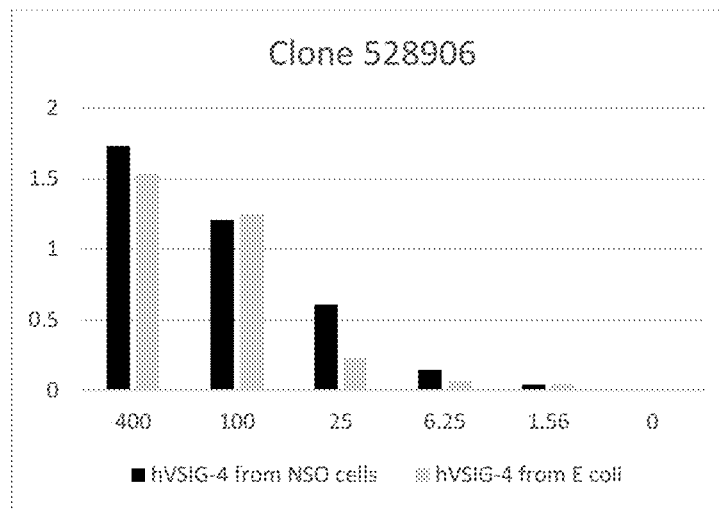
Figure 19C:
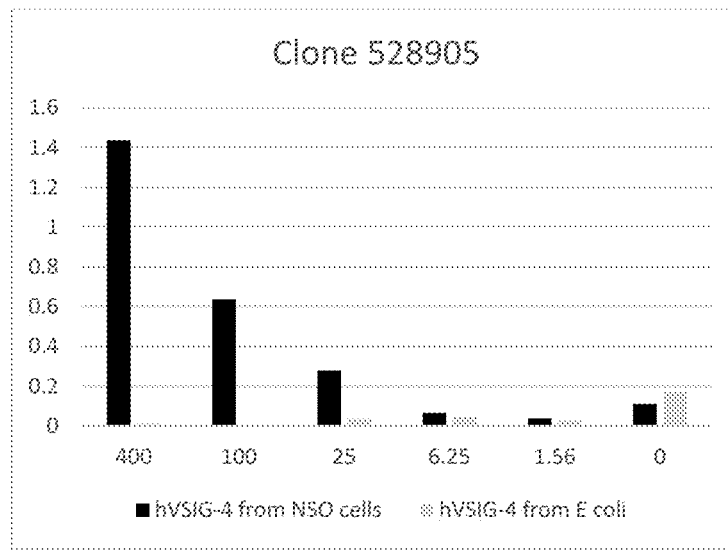

FIG. 19A-FIG. 19C show representative data for ELISA results obtained from direct ELISA testing. FIG. 19A shows Ms x hVSIG4 528902.11 recognizes monomeric *E. coli*-expressed VSIG-4, but not NSO-expressed, dimerized VSIG-4. FIG. 19B shows Ms x hVSIG4 528906.11 recognizes glycosylated and non-glycosylated VSIG-4 protein equally. FIG. 19C shows Ms x hVSIG4 528905.11 recognizes glycosylated VSIG-4 protein but not the *E. coli*-expressed VSIG-4.

DETAILED DESCRIPTION OF ILLUSTRATIVE EMBODIMENTS

This disclosure describes antibodies capable of specifically binding V-set and Ig domain-containing 4 (VSIG-4 or VSIG4 also known as Complement Receptor Ig (CRIg) and Z391G); antibodies capable of blocking interactions between VSIG-4 and its ligands including, for example, a newly observed interaction between VSIG-4 and SIGLEC-7; compositions including the antibodies describes herein; and methods of making and using those antibodies and compositions.

VSIG-4 acts as a negative regulator of T cell activation, likely playing a role in maintaining T cell tolerance. Thus, over-expression of VSIG-4 in inflammatory tumor microenvironments may promote tumor tolerance. Therefore, antibodies that identify VSIG-4 have potential diagnostic value to, for example, allow the identification of aggressive grade tumors, provide an indication of potential long-term prognosis in an animal having a tumor, or for use as an aid to guide treatment. In addition, a neutralizing antibody that abrogates VSIG-4-induced inhibition of T cell activation could allow for an increased immune response against tumor cells.

Using a screen for protein-protein interactions, sialic acid-binding Ig-like lectin-7 (Siglec7) was identified as a potential ligand for VSIG-4.

Siglec7 is an immunoglobulin family monomer expressed on the surface of natural killer (NK) cells and CD8⁺ T cells (Nicoll et al. (1999) *J Biol. Chem.* 274:34). Siglec7 is expressed on a highly functional subset of NK cells, and ligation of Siglec7 suppressed NK cell-mediated functions, suggesting Siglec7 may act as an inhibitory receptor (Shao et al. (2016) *Scand. J. Immunol.* 84:182). Furthermore, expression of Siglec7 ligands in the tumor microenvironment affects NK cell tumor immunosurveillance (Jandus (2014) *J Clin. Invest.* 124:1810).

Sialic acid-binding, Ig-type lectins (SIGLECS or Siglecs) are typically activated by engagement with sialic-acid modified proteins (or lipids), and the specificity of the interaction is determined both by the Siglec target molecule (including, for example, the precise glycan modification of a particular target protein, which is often not limited to a single site) as well as the Siglec molecule itself (for example, different Siglecs may bind to different sets of glycan modifications), and hence the specificity or promiscuity of a Siglec-target interaction can be difficult to determine.

As further described herein, therapeutic blockade of the VSIG-4/Siglec7 interaction with a neutralizing antibody may serve to release VSIG4-induced inhibition and to increase an immune response against the tumor cells.

Antibodies

In some embodiments, this disclosure describes an antibody that binds to VSIG-4 (that is, an anti-VSIG-4 antibody). In some embodiments, the antibody binds to human VSIG-4 (hVSIG-4).

In some embodiments, an antibody that binds to VSIG-4 is a monoclonal antibody. In some embodiments, the antibodies that bind to VSIG-4 include monoclonal antibodies produced by the hybridoma cell lines (also referred to herein as clones) listed in Table 1 and/or by recombinant methods.

In some embodiments, the antibody is an isolated antibody. In some embodiments, the antibodies may be isolated or purified by conventional immunoglobulin purification procedures, such as protein A- or G-Sepharose, hydroxylapatite chromatography, gel electrophoresis, dialysis, or affinity chromatography.

In some embodiments, an antibody that binds to VSIG-4 recognizes a VSIG-4 polypeptide. In some embodiments, the VSIG-4 polypeptide is human VSIG-4 (Uniprot number: Q9Y279; Gene ID 11326) or a fragment thereof. In some embodiments, the VSIG-4 polypeptide is mouse VSIG-4 (Uniprot number: F6TUL9) or a fragment thereof. In some embodiments, an antibody that binds to VSIG-4 recognizes a non-reduced VSIG-4 polypeptide.

In some embodiments, an antibody that binds to VSIG-4 binds to glycosylated and unglycosylated VSIG-4. In some embodiments, an antibody that binds to VSIG-4 recognizes a VSIG-4 polypeptide and not a glycan-modification of VSIG-4. In some embodiments, an antibody that binds to VSIG-4 recognizes a glycan-modification of VSIG-4. In some embodiments, an antibody that binds to VSIG-4 does not bind to an α(2,8)-linked polysialic acid. In some embodiments, an antibody that binds to VSIG-4 binds to an α(2,8)-linked polysialic acid.

In some embodiments, an antibody that binds to VSIG-4 preferably binds to an extracellular domain of VSIG-4. In some embodiments, the extracellular domain of VSIG-4 includes amino acids 20-283 of Uniprot number Q9Y279. An extracellular domain of VSIG-4 may include an Ig domain, as shown in some embodiments, in FIG. 8. In some embodiments, an antibody that binds to VSIG-4 may bind to Ig domain 1 of VSIG-4 (amino acids 21-131 of Q9Y279). In some embodiments, an antibody that binds to VSIG-4 may bind to Ig domain 2 of VSIG-4 (amino acids 143-226 of Q9Y279).

In some embodiments, an antibody that binds to VSIG-4 may include a derivative of an antibody that is modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, toxins, or linkage to a cellular ligand or other protein. Any of numerous chemical modifications may be carried out by known techniques, including, but not limited to, specific chemical cleavage, acetylation, formylation, and metabolic synthesis of tunicamycin. Additionally, the derivatives may contain one or more non-classical amino acids.

An antibody that binds to VSIG-4 may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, coenzymes, colored particles, biotin, or digoxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Ln, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

In some embodiments, an antibody that binds to VSIG-4 includes a monoclonal antibody produced by at least one of the following hybridoma cell lines (also referred to herein as clones): Ms x hVSIG4 528902.11 (ATCC Accession No. PTA-124187); Ms x hVSIG4 528903.111 (ATCC Accession No. PTA-124188); Ms x hVSIG4 528905.11 (ATCC Accession No. PTA-124189); Ms x hVSIG4 528906.11 (ATCC Accession No. PTA-124178); Ms x hVSIG4 528908.11 (ATCC Accession No. PTA-124179); Ms x hVSIG4 528910.111 (ATCC Accession No. PTA-124180); Ms x hVSIG4 528912.11 (ATCC Accession No. PTA-124181); Ms x hVSIG4 528922.111 (ATCC Accession No. PTA-124182); Ms x hVSIG4 528927.111 (ATCC Accession No. PTA-124183); Rt x hVSIG4 489509.11 (ATCC Accession No. PTA-124184); Rt x hVSIG4 489517.111 (ATCC Accession No. PTA-124185); or Rt x hVSIG4 489518.11 (ATCC Accession No. PTA-124186).

In some embodiments, an antibody that binds to VSIG-4 includes a monoclonal antibody produced by Ms x hVSIG4 528902.11 (ATCC Accession No. PTA-124187).

In some embodiments, an antibody that binds to VSIG-4 includes a monoclonal antibody produced by Ms x hVSIG4 528903.111 (ATCC Accession No. PTA-124188).

In some embodiments, an antibody that binds to VSIG-4 includes a monoclonal antibody produced by Ms x hVSIG4 528905.11 (ATCC Accession No. PTA-124189).

In some embodiments, an antibody that binds to VSIG-4 includes a monoclonal antibody produced by Ms x hVSIG4 528906.11 (ATCC Accession No. PTA-124178).

In some embodiments, an antibody that binds to VSIG-4 includes a monoclonal antibody produced by Ms x hVSIG4 528908.11 (ATCC Accession No. PTA-124179).

In some embodiments, an antibody that binds to VSIG-4 includes a monoclonal antibody produced by Ms x hVSIG4 528910.111 (ATCC Accession No. PTA-124180).

In some embodiments, an antibody that binds to VSIG-4 includes a monoclonal antibody produced by Ms x hVSIG4 528912.11 (ATCC Accession No. PTA-124181).

In some embodiments, an antibody that binds to VSIG-4 includes a monoclonal antibody produced by Ms x hVSIG4 528922.111 (ATCC Accession No. PTA-124182).

In some embodiments, an antibody that binds to VSIG-4 includes a monoclonal antibody produced by Ms x hVSIG4 528927.111 (ATCC Accession No. PTA-124183).

In some embodiments, an antibody that binds to VSIG-4 includes a monoclonal antibody produced by Rt x hVSIG4 489509.11 (ATCC Accession No. PTA-124184).

In some embodiments, an antibody that binds to VSIG-4 includes a monoclonal antibody produced by Rt x hVSIG4 489517.111 (ATCC Accession No. PTA-124185).

In some embodiments, an antibody that binds to VSIG-4 includes a monoclonal antibody produced by or Rt x hVSIG4 489518.11 (ATCC Accession No. PTA-124186).

Also included in the present disclosure are monoclonal antibodies produced by progeny or derivatives of these hybridoma cell lines, monoclonal antibodies produced by equivalent or similar hybridoma cell lines, and/or recombinant derivatives made thereof. In some embodiments, an antibody that binds to VSIG-4 includes a recombinantly derived monoclonal antibody including, for example, a rabbit B cell derived monoclonal antibody.

An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and Chothia et al., J. Mol. Biol. 1987; 196: 901-917). Each $V_H$ and $V_L$ is composed of three CDRs and four FRs, arranged from amino-terminus to carboxy-terminus in the following order: FR1, CDR1, FR2, CDR2, FR3, CDR3, FR4.

In some embodiments, a monoclonal antibody includes a monoclonal antibody having the same heavy chain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having the same light chain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having the same heavy chain and the same light chain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody can contain one, two, three, four, five, six, or more amino acid substitutions in the heavy and/or the light chains identified above wherein the amino acid substitutions do not substantially affect binding of the antibody to VSIG-4.

In some embodiments, a monoclonal antibody includes a monoclonal antibody having the same $V_H$ domain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having the same $V_L$ domain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having the same $V_H$ domain and the same $V_L$ domain as a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody can contain one, two, three, four, five, six, or more amino acid substitutions in the $V_H$ domains and/or the $V_L$ domains identified above which do not substantially affect binding of the antibody to VSIG-4.

In some embodiments, a monoclonal antibody includes a monoclonal antibody having at least one CDR of the $V_H$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having at least two CDRs of the $V_H$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having at least three CDRs of the Vu domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

Additionally or alternatively, in some embodiments, a monoclonal antibody includes a monoclonal antibody having at least one CDR of the $V_L$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having at least two CDRs of the $V_L$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody includes a monoclonal antibody having at least three CDRs of the $V_L$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody can contain one, two, three, four, five, six, or more amino acid substitutions in one or more CDRs identified above which do not substantially affect binding of the antibody to VSIG-4.

In some embodiments, a monoclonal antibody can contain one, two, three, four, five, six, or more amino acid substitutions in one or more framework regions (FRs). In some embodiments, the substitutions or substitutions in the framework regions (FRs) do not substantially affect binding of the antibody to VSIG-4.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least one CDR of a $V_H$ domain of a monoclonal antibody produced by at least one of the following hybridoma cell lines: Ms x hVSIG4

528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least two CDRs of a $V_H$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody includes a monoclonal antibody having an amino acid sequence at least 70%, at least 80%, at least 85%, at least 90%, at least 95%, at least 96%, at least 97%, at least 98%, or at least 99% identical to an amino acid sequence of at least three CDRs of a $V_H$ domain of a monoclonal antibody produced by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody includes an antibody having an amino acid sequence at least 70%, at least 80%, at least 85%, at least 90%, at least 95%, at least 96%, at least 97%, at least 98%, or at least 99% identical to at least one CDR of a $V_L$ domain of the antibody expressed by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody includes an antibody having an amino acid sequence at least 70%, at least 80%, at least 85%, at least 90%, at least 95%, at least 96%, at least 97%, at least 98%, or at least 99% identical to at least two CDRs of a $V_L$ domain of the antibody expressed by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

In some embodiments, a monoclonal antibody includes an antibody having an amino acid sequence at least 70%, at least 80%, at least 85%, at least 90%, at least 95%, at least 96%, at least 97%, at least 98%, or at least 99% identical to at least three CDRs of a $V_L$ domain of the antibody expressed by at least one of the following hybridoma cell lines: Ms x hVSIG4 528902.11; Ms x hVSIG4 528903.111; Ms x hVSIG4 528905.11; Ms x hVSIG4 528906.11; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11.

The antibody may be an antibody from any suitable species. In some embodiments, the antibody may be a mouse antibody. In some embodiments, the antibody may be a rat antibody. In some embodiments, the antibody may be a rabbit antibody.

In some embodiments, the antibody is an IgG antibody. In some embodiments, the antibody may be an antibody or an IgG subclass including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain.

In some embodiments, the monoclonal antibody includes an antigen-binding fragment including an Fab fragment, an Fab' fragment, an F(ab)$_2$ fragment, and/or an Fv fragment.

A monoclonal antibody may be obtained by any suitable technique. In some embodiments, an antibody that binds to VSIG-4 may be made by recombinant DNA methods, produced by phage display, and/or produced by combinatorial methods. DNA encoding an antibody that binds to VSIG-4 may be readily isolated and sequenced using conventional procedures. In some embodiments, a hybridoma cell described herein may serve as a source of such DNA. Once isolated, the DNA may be transfected into a host cell (including, for example, simian COS cells, Chinese hamster ovary (CHO) cells, human embryonic kidney cells (HEK), or myeloma cells that do not otherwise produce immunoglobulin protein) or introduced into a host cell by genome editing (for example, using a CRISPR-Cas system) to obtain the synthesis of monoclonal antibodies in a recombinant host cells. The DNA encoding an antibody that binds to VSIG-4 may be modified to, for example, humanize the antibody.

In some embodiments, the antibody may be a humanized antibody. An antibody that binds to VSIG-4 may be humanized by any suitable method. Techniques for producing humanized monoclonal antibodies may be found, for example, in Jones et al. (1986) *Nature* 321:522 and Singer et al. (1993) *J. Immunol.* 150:2844. For example, humanization of the antibody may include changes to the antibody to reduce the immunogenicity of the antibody when used in humans. In some embodiments, a humanized antibody that binds to VSIG-4 may include at least a portion of an immunoglobulin constant region (Fc) of a human immunoglobulin. A humanized antibody that binds to VSIG-4 may include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody, that binds to VSIG-4. In some embodiments, Fv framework residues of a human immunoglobulin may be replaced by corresponding non-human residues from an antibody that binds to VSIG-4.

In some embodiments, a monoclonal antibody includes a chimeric antibody, that is, an antibody in which different portions are derived from different animal species. A chimeric antibody may be obtained by, for example, splicing the genes from a mouse antibody molecule with appropriate antigen specificity together with genes from a human antibody molecule of appropriate biological specificity. See, for example, Takeda et al. (1985) *Nature* 314:544.

In some embodiments, an antibody includes a bispecific or a bifunctional antibody. A bispecific or bifunctional antibody is an artificial hybrid antibody having two different heavy/light chain pairs and two different binding sites. A bispecific antibody may be produced by a variety of methods including fusion of hybridomas or linking of F(ab') fragments. See, for example, Songsivilai and Lachmann (1990) *Clin. Exp. Immunol.* 79:315; Kostelny et al. (1992) *J. Immunol.* 148:1547. In addition, bispecific antibodies may be formed as "diabodies" (Holliger et al. (1993) *PNAS* USA 90:6444) or "Janusins" (Traunecker et al. (1991) *EMBO J.* 10:3655; Traunecker et al. (1992) *Int. J. Cancer Suppl.* 7:51).

In some embodiments, an antibody is produced by an animal (including, but not limited to, human, mouse, rat, rabbit, hamster, goat, horse, chicken, or turkey), produced by a cell from an animal, chemically synthesized, or recombinantly expressed. The antibody may be purified by any method known in the art for purification of an immunoglobulin molecule, for example, by chromatography (for example, ion exchange, affinity, and sizing column chromatography), centrifugation, differential solubility, or by any other standard technique for the purification of proteins. In addition, an antibody may be fused to a heterologous polypeptide sequence, as described herein or otherwise known in the art, including, for example, to facilitate purification.

A monoclonal antibody may be assayed for immunospecific binding by the methods described herein and by any suitable method known in the art. The immunoassay that may be used includes but is not limited to a competitive and/or a non-competitive assay system using a technique such as BIACORE analysis, fluorescence activated cell sorter (FACS) analysis, immunofluorescence, immunocytochemistry, Western blot, radio-immunoassay, enzyme linked immunosorbent assay (ELISA), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see for example, Ausubel et al., eds, Current Protocols in Molecular Biology, Vol. 1, John Wiley & Sons, Inc., N.Y. (1994)).

In some embodiments, an antibody that binds to VSIG-4 includes an antibody that abrogates binding of VSIG-4 to a VSIG-4 ligand. In some embodiments, the antibody includes an antibody that abrogates binding of VSIG-4 to Siglec-7. In some embodiments the Siglec-7 is human Siglec-7 (Uniprot number: Q9Y286). In some embodiments, the antibody may decrease the binding of VSIG-4 to a VSIG-4 ligand (including, for example, Siglec-7) by at least 10 percent (%), at least 15%, at least 20%, at least 25%, at least 30%, at least 40%, at least 50%, at least 60%, at least 70%, at least 80%, at least 90%, at least 95%, or at least 98%.

In some embodiments, a VSIG-4 ligand may be anchored a cell via a transmembrane domain. In some embodiments, a VSIG-4 ligand may be in solution.

In some embodiments, an antibody that abrogates binding of VSIG-4 to Siglec-7 includes a monoclonal antibody produced by at least one of the following hybridoma cell lines: Ms x hVSIG4 528903.111; Ms x hVSIG4 528908.11; Ms x hVSIG4 528912.11; Rt x hVSIG4 489509.11; Rt x hVSIG4 489517.111; or Rt x hVSIG4 489518.11.

In some embodiments, at least one of the VSIG-4 and the VSIG-4 ligand may be on a cell surface. For example, VSIG-4 may be expressed on the surface of a macrophage including, for example, an M2 macrophage. An M2 macrophage may include one or more M2 subtypes including M2a, M2b, M2c and M2d subtypes. In some embodiments, a macrophage may preferably include an M2c macrophage. When at least one of the VSIG-4 and the VSIG-4 ligand are on the surface of a cell, an antibody that binds to VSIG-4 may abrogate binding of VSIG-4 to a cell expressing a VSIG-4 ligand, binding of a cell expressing VSIG-4 to a VSIG-4 ligand, and/or binding of a cell expressing VSIG-4 to a cell expressing a VSIG-4 ligand. For example, when VSIG-4 and the VSIG-4 ligand Siglec-7 are expressed on the surface of a cell, an antibody that binds to VSIG-4 may abrogate cell-cell binding.

In some embodiments, an antibody that binds to VSIG4 may be made by immunizing an animal with the extracellular domain of VSIG4. In some embodiments, an antibody that binds to VSIG4 may be made by immunizing an animal with amino acids 1-283 of human VSIG-4 (Uniprot number: Q9Y279; gene ID 11326). In some embodiments, an antibody that binds to VSIG4 may be made by immunizing an animal with a portion of human VSIG-4. In some embodiments, the animal may be a mammal. For example, the animal may be a rabbit, a mouse, a goat, a sheet, a llama or a rat. In some embodiments, the animal may be a chicken.

In another aspect, this disclosure describes an isolated polynucleotide molecule. In some embodiments, the isolated polynucleotide molecule includes a nucleotide sequence encoding an antibody. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to nucleotide sequence encoding an antibody described herein. In some embodiments, the isolated polynucleotide molecule includes polynucleotides that hybridize under high stringency to a nucleotide sequence encoding an antibody or a complement thereof. As used herein "stringent conditions" refer to the ability of a first polynucleotide molecule to hybridize, and remain bound to, a second, filter-bound polynucleotide molecule in 0.5 M NaHPO$_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). In some embodiments, the isolated polynucleotide molecule includes polynucleotides that encode one or more of the CDRs or the heavy and/or light chains of a monoclonal antibody of the present invention. General techniques for cloning and sequencing immunoglobulin variable domains and constant regions are well known. See, for example, Orlandi et al. (1989) *Proc. Nat'l Acad. Sci. USA* 86:3833.

In another aspect, this disclosure describes recombinant vectors including an isolated polynucleotide of the present invention. The vector may be, for example, in the form of a plasmid, a viral particle, or a phage. The appropriate DNA sequence may be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector may be used.

In a further aspect, this disclosure also includes a host cell containing at least one of the above-described vectors. The host cell may be a higher eukaryotic cell, such as a mammalian or insect cell, or a lower eukaryotic cell, such as a yeast cell. Or, the host cell may be a prokaryotic cell, such as a bacterial cell, or a plant cell. Introduction of a vector construct into the host cell may be effected by any suitable techniques, such as, for example, calcium phosphate transfection, DEAE-Dextran mediated transfection, or electroporation. (Davis et al., Basic Methods in Molecular Biology (1986)).

Antibodies of the present invention may be expressed in mammalian cells, yeast, bacteria, or other cells under the control of appropriate promoters. Cell-free translation systems may also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y. (1989).

Also included in the present invention are phage display libraries expressing one or more hypervariable regions from an antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries may be prepared, for example, using the PH.D.-7 Phage Display Peptide Library Kit (Catalog #E8100S) or the PH.D.-12 Phage Display Peptide Library Kit (Catalog #E8110S) available from New England Biolabs Inc., Ipswich, MA See, for example, Smith and Petrenko (1997) Chem Rev. 97:391-410.

Hybridoma Cell Lines

This disclosure further describes hybridoma cell lines (also referred to herein as "clones") expressing monoclonal antibodies including, for example, the following hybridoma cell lines: Ms x hVSIG4 528902.11; Ms x hVSIG4 528903.111; Ms x hVSIG4 528905.11; Ms x hVSIG4 528906.111; Ms x hVSIG4 528908.11; Ms x hVSIG4 528910.111; Ms x hVSIG4 528912.11; Ms x hVSIG4 528922.111; Ms x hVSIG4 528927.111; Rt x hVSIG4 489509.11; Rt x hVSIG4 489517.111; or Rt x hVSIG4 489518.11. In some embodiments, a monoclonal antibody produced by a hybridoma cell line binds to VSIG-4. In some embodiments, a monoclonal antibody produced by a hybridoma cell line abrogates binding of VSIG-4 to Siglec-7.

Hybridoma cell lines may be obtained by various techniques familiar to those skilled in the art. For example, cells from an animal immunized with a desired antigen are immortalized, commonly by fusion with a myeloma cell (see, for example, Kohler and Milstein (1976) Eur. J. Immunol. 6:511; J. Goding in "Monoclonal Antibodies: Principles and Practice," Academic Press, pp 59-103 (1986); and Harlow et al., Antibodies: A Laboratory Manual, page 726 (Cold Spring Harbor Pub. 1988). In some embodiments, the immunized animal is preferably a mammal. In some embodiments, the immunized animal is a rat including, for example, a Wistar rat, or a mouse including, for example, a BALB/C mouse. In some embodiments, the cells from the animal are spleen cells. In some embodiments, the cells from the animal are preferably lymphocytes. In some embodiments, the myeloma cell includes a P3X63Ag8.653 cell.

Other known methods of producing transformed B cell lines that produce monoclonal antibodies may also be used.

Recombinant Antibodies

This disclosure further describes recombinantly-derived monoclonal antibodies. Recombinantly derived monoclonal antibodies may include, for example, rabbit B cell derived monoclonal antibodies. Monoclonal antibodies of the present disclosure may be produced by any suitable recombinant technique including, for example, by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods may be used to generate human monoclonal antibodies.

Uses for the Anti-VSIG-4 Antibodies

An antibody that binds to VSIG-4, as described herein, may be used for any suitable application. For example, a monoclonal antibody may be used in both in vitro and in vivo diagnostic and therapeutic methods.

In some embodiments, an antibody may be used to determine a level of expression of VSIG-4 protein in vitro or in vivo. In some embodiments, determining a level of VSIG-4 protein expression may be used to detect cancer. In some embodiments, an antibody may be used to label a cell in vivo or in vitro. In some embodiments, an antibody may be used to determine a level of expression of VSIG-4 protein in a patient sample. In some embodiments, a patient sample may include a mammalian cancer cell. In some embodiments, the mammalian cancer cell may include a lung cancer cell or a glioma cell. In some embodiments, a patient sample including, for example, a patient samples including a mammalian cancer cell may include a macrophage.

In some embodiments, the antibody may be labeled. For example, an antibody may be used to label a cell, and the labeled cell may be directly or indirectly imaged via secondary methods. In some embodiments, the cell is a mammalian cell.

In some embodiments, an antibody may be used to identify the presence or absence of VSIG-4 protein in a sample from a subject. In some embodiments, identifying the presence of VSIG-4 may include identifying an amount of VSIG-4 in a sample from a subject. In some embodiments, identifying the presence of VSIG-4 may be used to detect cancer.

VSIG-4 has previously been reported to be expressed on tissue resident macrophages. Massive infiltrates of VSIG-4$^+$ macrophages into the tumor microenvironment have been observed in patients diagnosed with non-small cell lung cancer (Liao et al. (2014) Lab. Invest. 94:706), and high VSIG-4 expression has also been correlated with high-grade glioma and poor patient prognosis (Xu et al. (2015) Am. J. Transl. Res. 7:1172). As shown in Example 3, VSIG-4 expression was detected on CD14-positive human PBMC monocytes differentiated in vitro to the M2c macrophage lineage, polarized with either Dexamethasone or recombinant human IL-10 (rhIL-10) (FIG. 6).

In some embodiments, an anti-VSIG-4 antibody may be used to determine the level of VSIG-4 expression on a cancer cell, a tumor cell, or a patient sample including a cancer cell or a tumor cell. In some embodiments, a patient sample including a cancer cell or a tumor cell may further include a macrophage. In some embodiments, an anti- VSIG-4 antibody may be used to determine the level of VSIG-4 expression in or on cells of a patient sample including, for example, a macrophage. In some embodiments, the level of VSIG-4 expression will be amplified. In some embodiments, an anti-VSIG-4 antibody may be used to determine the level of VSIG-4 expression in and/or on a macrophage. In some embodiments, identifying the expression or level of expression of VSIG-4 may be used to identify a cancer or a tumor; to assist in the grading or a cancer or a tumor; and/or to provide an indication of long-term prognosis. In some embodiments, the cancer may include a lung cancer or a glioma.

In some embodiments, an anti-VSIG-4 antibody may be used to treat a mammalian cancer. In some embodiments, treating a mammalian cancer may include exposing a mammal comprising a mammalian cancer cell an anti-VSIG-4 antibody. In some embodiments, VSIG-4 expression may be amplified in a patient sample that includes the mammalian cancer cell. For example, VSIG-4 expression may be amplified in a macrophage of the patient sample that includes the mammalian cancer cell. In some embodiments, the mammalian cancer may include a lung cancer or a glioma.

In some embodiments, an anti-VSIG-4 antibody may be used to treat an autoimmune disease. An autoimmune disease may include, for example, autoimmune type 1 diabetes mellitus, rheumatoid arthritis, psoriasis, or lupus. Without wishing to be bound by theory, because macrophages are known to play a role in the pathogenesis of certain autoimmune diseases, see, e.g., Campos Navegantes et al. (2017) *J. Transl. Med.* 15:36, and, as shown herein (see Example 5), an anti-VSIG-4 antibody may block the interaction of naturally expressed VSIG-4 on M2c macrophages with Siglec-7, an anti-VSIG-4 antibody may be used, for example, to treat an autoimmune disease that includes interactions with VSIG-4 expressed on M2c macrophages.

Figure 1:
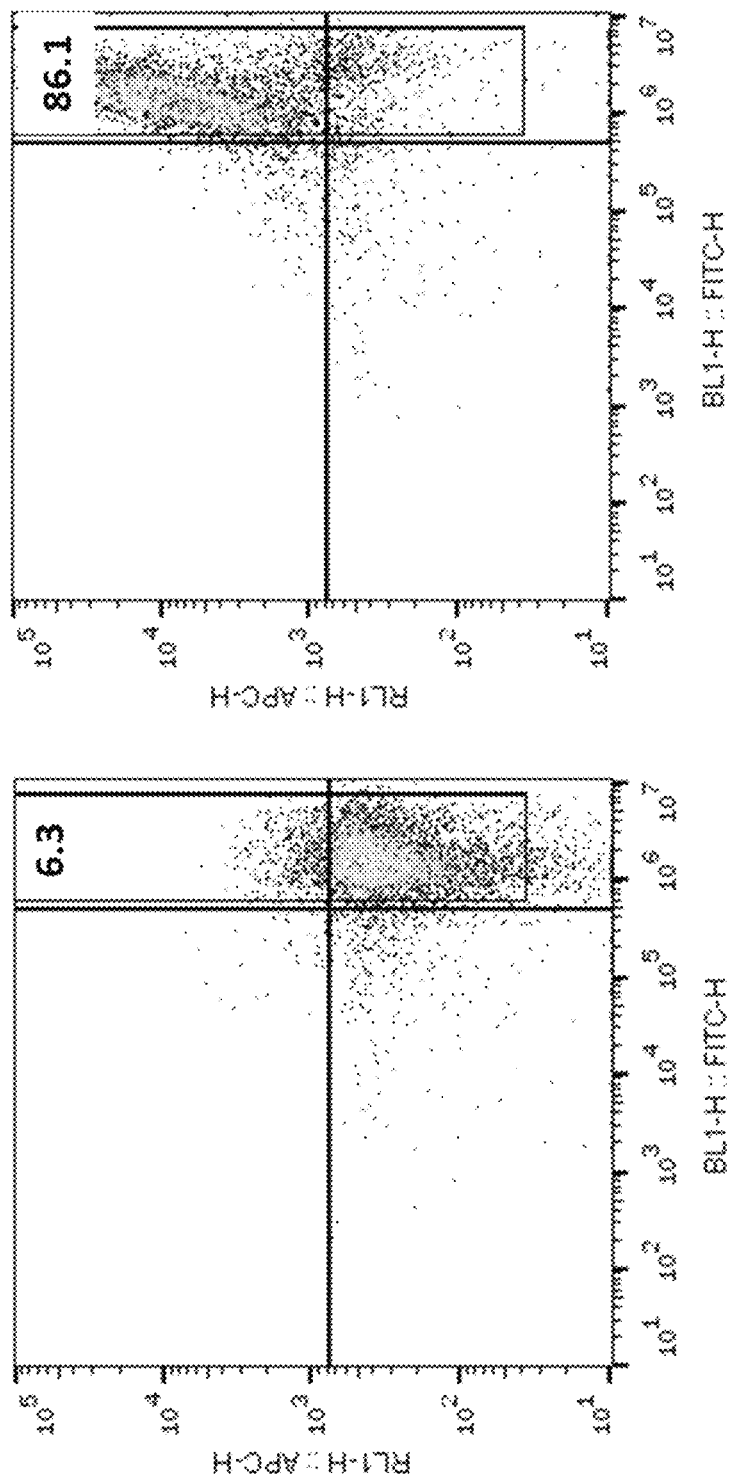
FIG. 1 shows cell-based detection of a Siglec-7/VSIG-4 interaction. Human VSIG-4 (hVSIG4)/eGFP HEK transfectants were incubated with recombinant human Siglec-7 (rhSiglec-7)/Fc protein (2 μg/mL) plus anti-Fc APC, or a negative control (anti-Fc-APC only). The percentage shown in the upper right quadrant indicates the level of interaction.
Figure 2A:
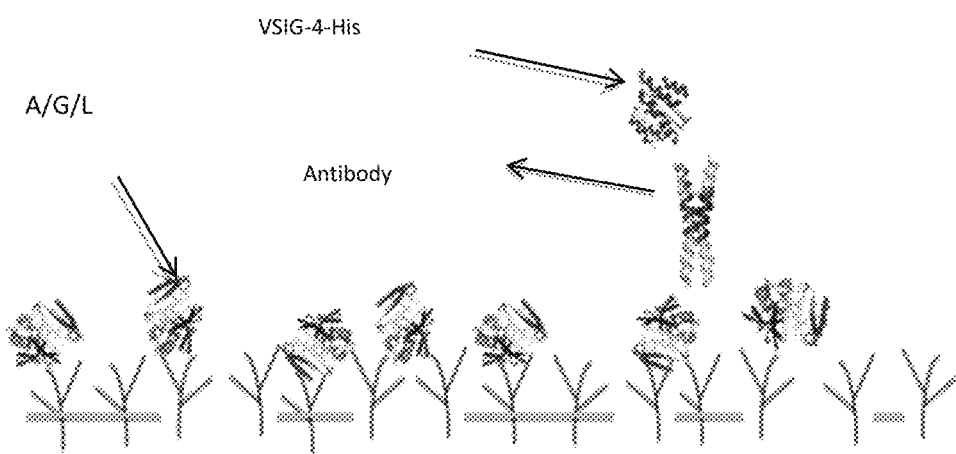
FIG. 2A-FIG. 2B shows surface plasmon resonance measured using BIACORE (GE Healthcare Worldwide, Chicago, IL) for confirmation of a VSIG-4-Siglec-7 protein-protein interaction.
Figure 2B:
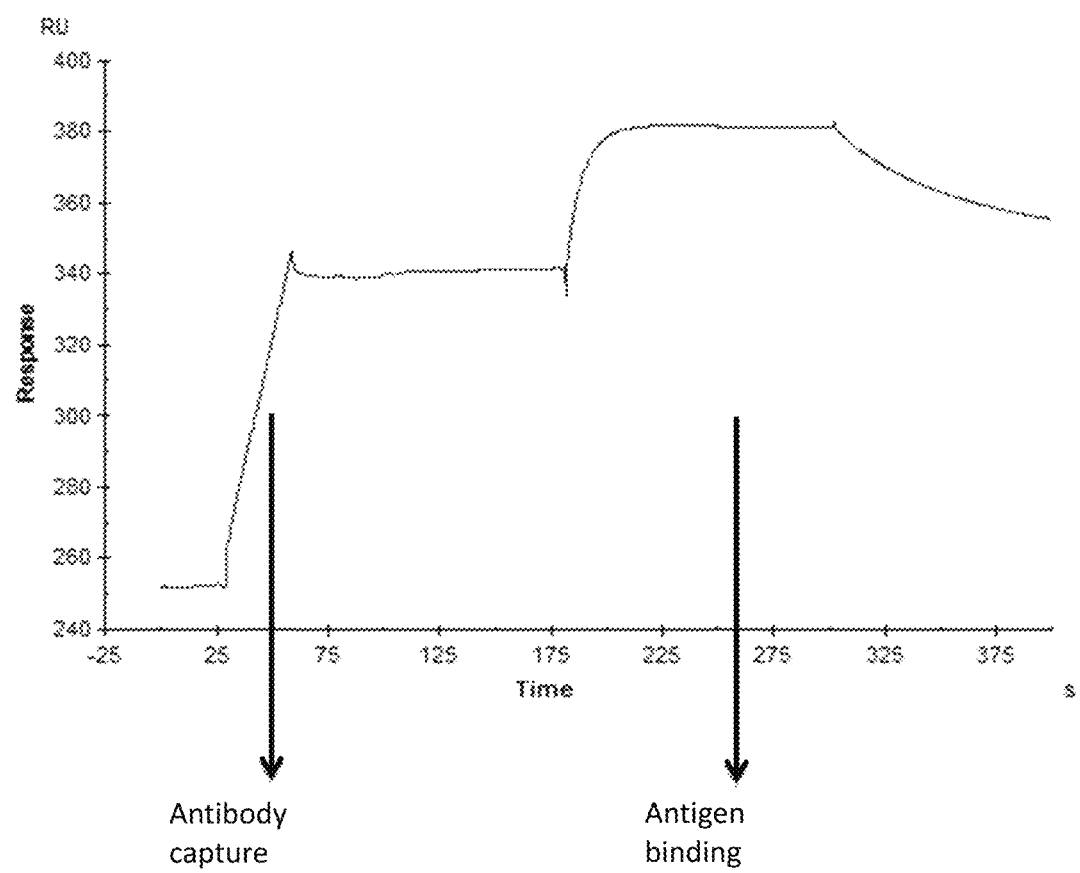
Figure 3:
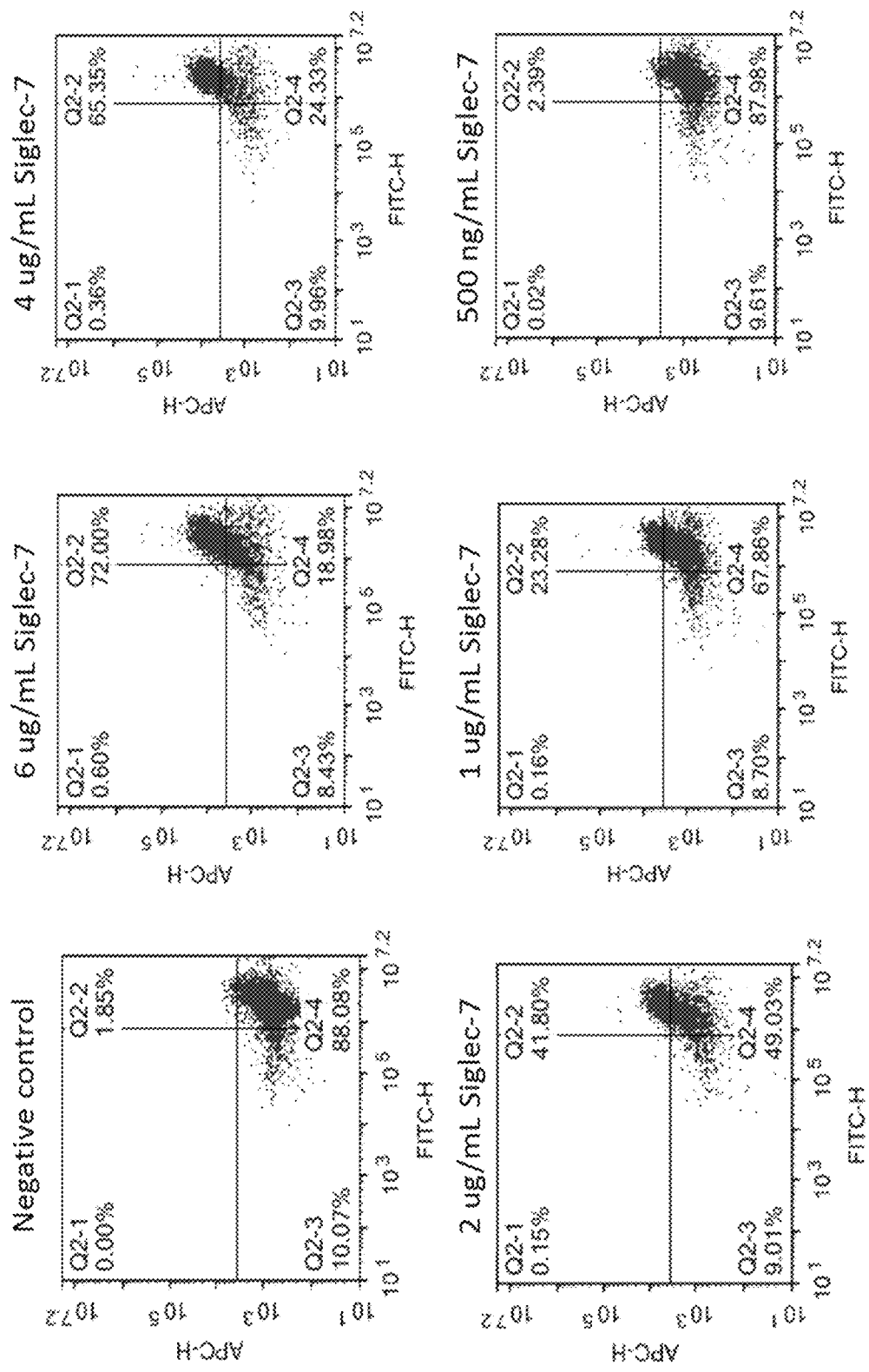
FIG. 3 shows recombinant human Siglec-7 (rhSiglec-7)/Fc protein titrates on hVSIG-4 transfectant cells. hVSIG4/eGFP HEK transfectant cells were incubated with varying amounts of rhSiglec-7/Fc protein (between 500 ng/mL and 6 μg/mL) or a negative control (FAB110A). The percentage shown in the upper right quadrant indicates the level of interaction.

As described in Example 1, soluble, recombinant human VSIG-4 was plated as a capture reagent in a standard ELISA assay. Recombinant, biotinylated human SIGLEC-7 was found to bind to VSIG-4 (FIG. 1 & Table 1). The putative protein-protein interaction was then examined in a cell-based assay. HEK cells transfected to over-express human VSIG-4 and eGFP were cultured with rhSIGLEC-7/Fc. Binding of rhSIGLEC-7/Fc to the cells was detected with APC-conjugated anti-Fc antibody by flow cytometry (FIG. 2). The binding of SIGLEC-7 to VSIG-4 was further analyzed via Surface Plasmon Resonance (SPR)/BIACORE (FIG. 3).

Figure 4:
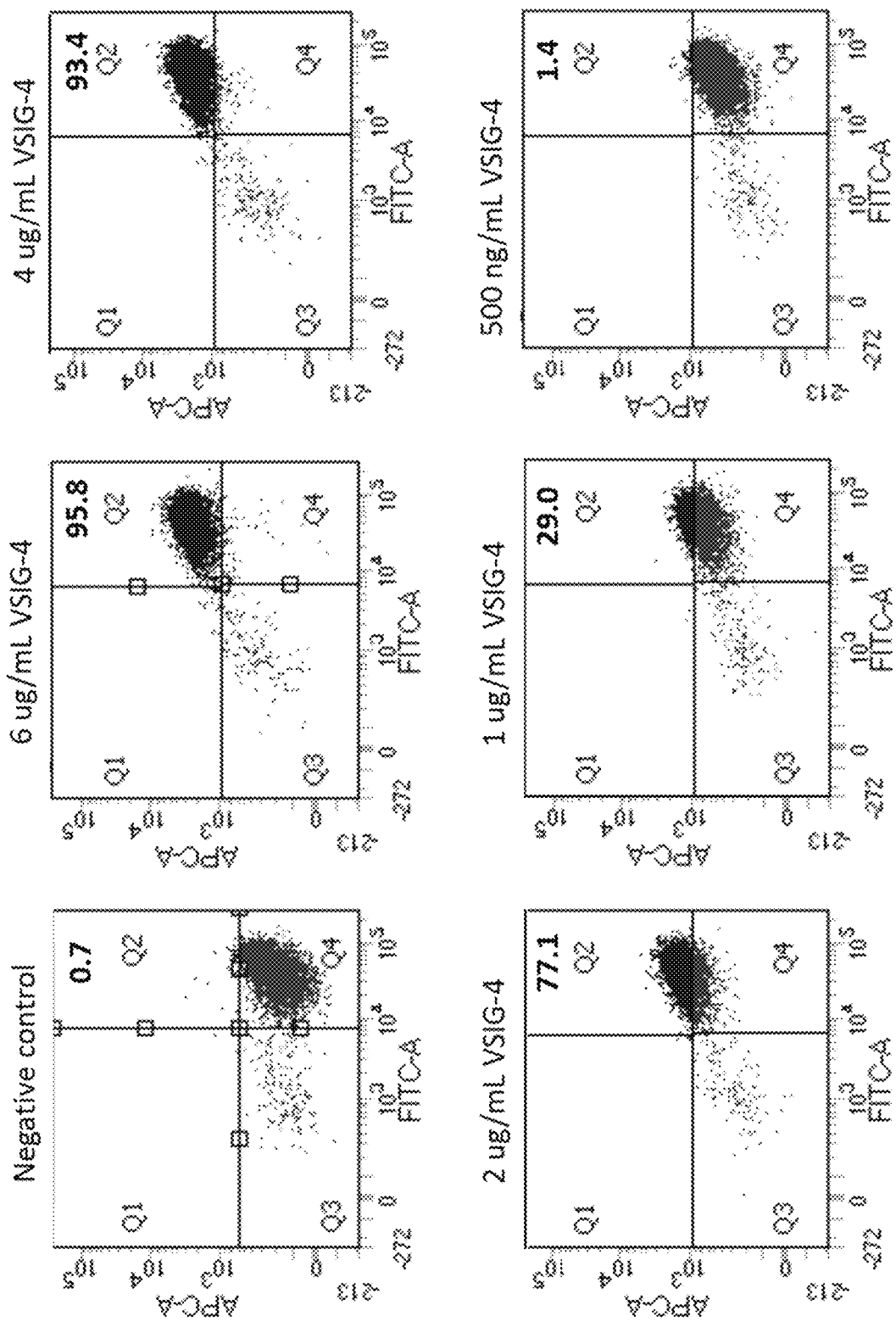
FIG. 4 shows recombinant human VSIG-4 (rhVSIG-4)/Fc protein titrates on hSiglec-7 transfectant cells. hSiglec-7/eGFP HEK transfecant cells were incubated with varying amounts of rhVSIG-4/Fc protein (between 500 ng/mL and 6 μg/mL) or a negative control (FAB110A). The percentage shown in the upper right quadrant indicates the level of interaction.

A cell-based assay was used to titrate the amount of rhSIGLEC-7 on VSIG-4 transfected cells, and the interaction was shown to be dose dependent (FIG. 4). To further confirm this interaction, the assay was flipped, and rhVSIG-4 was also shown bind SIGLEC-7 expressing cells in a dose dependent manner (FIG. 5).

Figure 5:
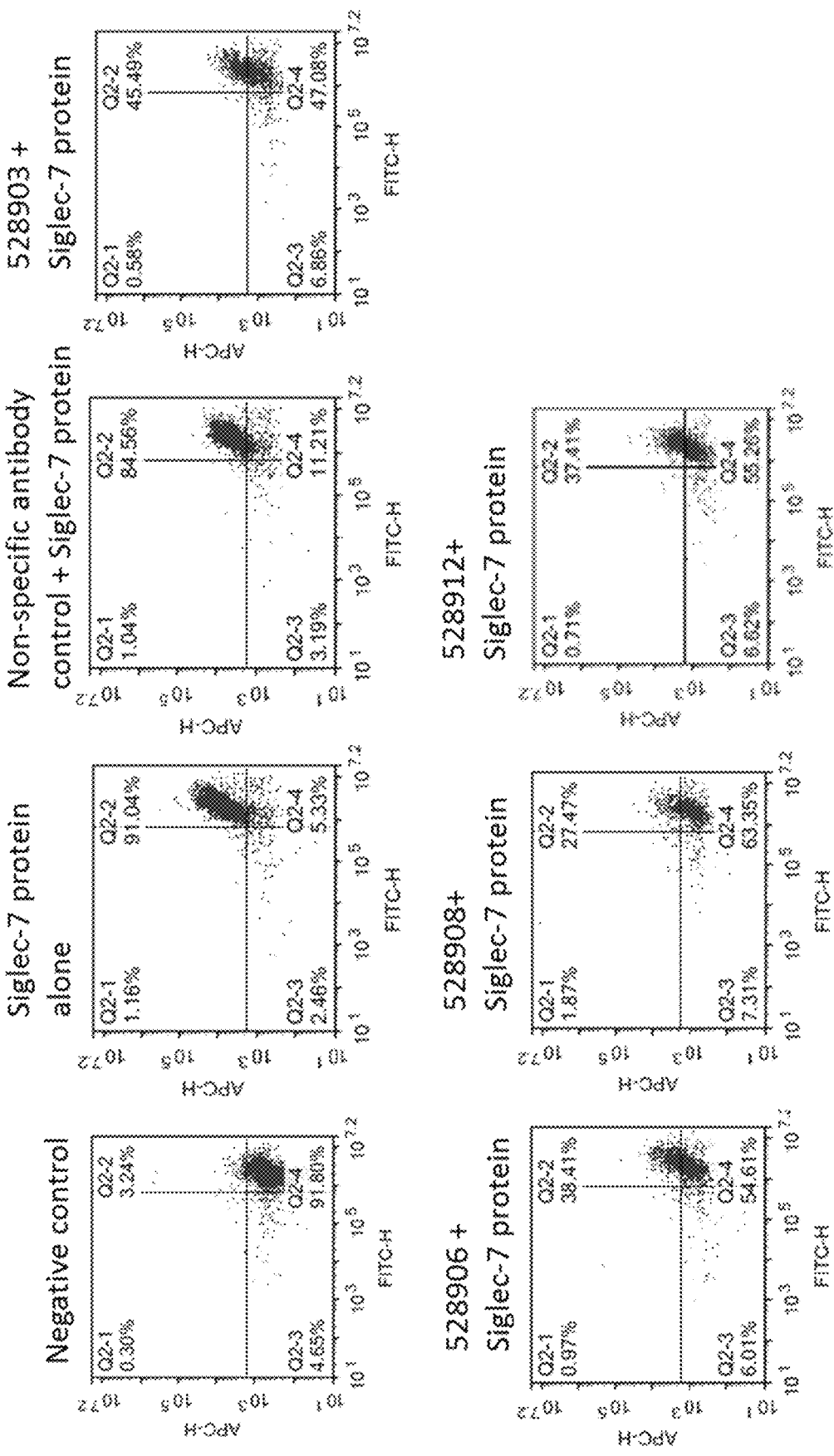
FIG. 5 shows four anti-human VSIG-4 antibodies block the interaction of VSIG-4 with rhSiglec-7/Fc. hVSIG4/eGFP HEK transfectants were incubated with four different anti-hVSIG-4 antibodies (produced by clones Ms x hVSIG4 528903.111 ("528903"), Ms x hVSIG4 528906.11 ("528906"), Ms x hVSIG4 528908.11 ("528908"), and Ms x hVSIG4 528912.11 ("528912")) at 2.5 μg/mL to test the antibody's capacity to block the interaction with Siglec-7. 4

As shown in Examples 2 and 3, the specific binding of rhSIGLEC-7 to VSIG-4 was confirmed using anti-VSIG-4 antibodies to block the interaction (FIG. 5). Four clones were shown to specifically block the SIGLEC-7/VSIG-4 interaction. The binding affinity of these and other monoclonal anti-VSIG-4 antibodies were determined via Surface Plasmon Resonance (SPR)/BIACORE (Table 2).

As shown in Example 4, VSIG-4 may be glycosylated (FIG. 9). As shown in Example 4 and Example 6, in some embodiments, in some embodiments, an anti-VSIG-4 antibody may bind to the VSIG-4 polypeptide and not to a glycan-modification of VSIG-4 (FIG. 10-FIG. 13, FIG. 19, Table 3), resulting in an anti-VSIG-4 antibody that may bind to both glycosylated and unglycosylated VSIG-4. In some embodiments an anti-VSIG4 antibody may bind to the glycosylated VSIG-4, but not the unglycosylated poylpeptide.

In some embodiments, an anti-VSIG-4 antibody or a composition comprising an anti-VSIG-4 antibody may be used to abrogate binding of VSIG-4 to Siglec-7. For example, as shown in Example 5, an anti-VSIG-4 antibody or a composition comprising an anti-VSIG-4 antibody may be used to abrogate a cell-cell interaction (FIG. 15-18). Without wishing to be bound by theory, it is believed that an antibody that abrogates binding of VSIG-4 to Siglec-7 could abrogate or inhibit T cell/NK cell immunosurveillance by ligation of Siglec-7 on CD8$^+$ T cells and NK cells. Thus, therapeutic blockade of the VSIG-4-Siglec7 interaction with neutralizing antibody could serve to release VSIG-4-induced inhibition and to enhance immune function against tumor cells or suppress immune responses in an auto-immune disease. Additionally or alternatively, an antibody that abrogates binding of VSIG-4 to Siglec-7 could abrogate or inhibit macrophage signaling by inhibiting the binding of Siglec-7 to VSIG-4 on a macrophage.

This disclosure further described a kit including an antibody. For example, a kit may include a composition that includes an anti-VSIG-4 monoclonal antibody. The antibodies in the kit may be labeled with one or more detectable markers, as described herein.

A kit may include one or more containers filled with one or more of the monoclonal antibodies of the invention. Additionally, the kit may include other reagents such as buffers and solutions needed to practice the invention are also included. Optionally associated with such container(s) may be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

Compositions Including Antibodies

In some embodiments, this disclosure describes a composition including at least one of the antibodies describes herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or nonspecific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (for example, vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (for example, neutral buffered saline or phosphate buffered saline), carbohydrates (for example, glucose, sucrose or dextrans), mannitol, proteins, polypeptides or amino acids such as glycine, antioxidants (for example, ascorbic acid, sodium metabisulfite, butylated hydroxytoluene, butylated hydroxyanisole, etc.), bacteriostats, chelating agents such as EDTA or glutathione, adjuvants (for example, aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

Administration and Treatment

The compositions of the present disclosure may be formulated in pharmaceutical preparations in a variety of forms adapted to the chosen route of administration. One of skill will understand that the composition will vary depending on mode of administration and dosage unit. For example, for parenteral administration, isotonic saline may be used. For topical administration a cream, including a carrier such as dimethylsulfoxide (DMSO), or other agents typically found in topical creams that do not block or inhibit activity of the peptide, may be used. Other suitable carriers include, but are not limited to alcohol, phosphate buffered saline, and other balanced salt solutions. The compounds of this invention may be administered in a variety of ways, including, but not limited to, intravenous, topical, oral, subcutaneous, intraperitoneal, and intramuscular delivery. In some aspects, the compounds of the present invention may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions may be determined without undue experimentation using standard dose-response protocols. Administration includes, but is not limited to, any of the dosages and dosing schedules, dosing intervals, and/or dosing patterns described in the examples included herewith.

The composition including an antibody according to the present disclosure may be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that may be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparations may be pyrogen-free.

Many suitable formulations are known, including polymeric or protein microparticles encapsulating drug to be released, ointments, gels, or solutions which may be used topically or locally to administer drug, and even patches, which provide controlled release over a prolonged period of time. These may also take the form of implants. Such an implant may be implanted within the tumor.

The compounds of the present invention may also be provided in a lyophilized form. Such compositions may include a buffer, for example, bicarbonate, for reconstitution prior to administration, or the buffer may be included in the lyophilized composition for reconstitution with, for example, water. The lyophilized composition may further comprise a suitable vasoconstrictor, for example, epinephrine. The lyophilized composition may be provided in a syringe, optionally packaged in combination with the buffer for reconstitution, such that the reconstituted composition may be immediately administered to a patient.

As used herein "treating" or "treatment" may include therapeutic and/or prophylactic treatments. "Treating a disorder," as used herein, is not intended to be an absolute term. Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90%, 80%, 70%, 60%, 50%, 40%, 30%, 20%, 10%, 5%, or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. Compositions that exhibit high therapeutic indices may be preferred. The data obtained from cell culture assays and animal studies may be used in formulating a range of dosage for use in humans. The dosage of such compositions may preferably lie within a range of circulating concentrations that include the $ED_{50}$ with little or no toxicity. The dosage may vary within this range depending upon the dosage form employed and the route of administration utilized. The exact formulation, route of administration and dosage may be chosen by the individual physician in view of the patient's condition.

A composition as described herein may be administered at once, or may be divided into a number of smaller doses to be administered at intervals of time. For example, compositions may be administered repeatedly, for example, at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects of the methods of the present disclosure, a method further includes the administration of one or more additional therapeutic agents. One or more additional therapeutic agents may be administered before, after, and/or coincident to the administration of a monoclonal antibody as described herein. An additional therapeutic agent may include, for example, chemotherapy, radiation therapy, etc. Additional therapeutic agents may be administered separately or as part of a mixture or cocktail. In some aspects of the present disclosure, the administration of an antibody may allow for the effectiveness of a lower dosage of other therapeutic modalities when compared to the administration of the other therapeutic modalities alone, providing relief from the toxicity observed with the administration of higher doses of the other modalities.

In some aspects of the methods of the present disclosure, the administration of a composition as described herein and the at least one additional therapeutic agent demonstrate therapeutic synergy. In some aspects of the methods of the present disclosure, a measurement of response to treatment observed after administering both an antibody as described herein and the additional therapeutic agent is improved over the same measurement of response to treatment observed after administering either the antibody or the additional therapeutic agent alone.

EXEMPLARY EMBODIMENTS

Embodiment 1. A monoclonal antibody that binds to VSIG-4.

Embodiment 2. A monoclonal antibody produced by at least one of the following clones:
- Ms x hVSIG4 528902.11 (ATCC Accession No. PTA-124187);
- Ms x hVSIG4 528903.111 (ATCC Accession No. PTA-124188);
- Ms x hVSIG4 528905.11 (ATCC Accession No. PTA-124189);
- Ms x hVSIG4 528906.11 (ATCC Accession No. PTA-124178);
- Ms x hVSIG4 528908.11 (ATCC Accession No. PTA-124179);
- Ms x hVSIG4 528910.111 (ATCC Accession No. PTA-124180);
- Ms x hVSIG4 528912.11 (ATCC Accession No. PTA-124181);
- Ms x hVSIG4 528922.111 (ATCC Accession No. PTA-124182);
- Ms x hVSIG4 528927.111 (ATCC Accession No. PTA-124183);
- Rt x hVSIG4 489509.11 (ATCC Accession No. PTA-124184);
- Rt x hVSIG4 489517.111 (ATCC Accession No. PTA-124185); and
- Rt x hVSIG4 489518.11 (ATCC Accession No. PTA-124186).

Embodiment 3. A monoclonal antibody, wherein the monoclonal antibody comprises
at least one of
  a heavy chain variable region of a monoclonal antibody produced by at least one of the following clones:
  - Ms x hVSIG4 528902.11 (ATCC Accession No. PTA-124187);
  - Ms x hVSIG4 528903.111 (ATCC Accession No. PTA-124188);
  - Ms x hVSIG4 528905.11 (ATCC Accession No. PTA-124189);
  - Ms x hVSIG4 528906.11 (ATCC Accession No. PTA-124178);
  - Ms x hVSIG4 528908.11 (ATCC Accession No. PTA-124179);
  - Ms x hVSIG4 528910.111 (ATCC Accession No. PTA-124180);
  - Ms x hVSIG4 528912.11 (ATCC Accession No. PTA-124181);
  - Ms x hVSIG4 528922.111 (ATCC Accession No. PTA-124182);
  - Ms x hVSIG4 528927.111 (ATCC Accession No. PTA-124183);
  - Rt x hVSIG4 489509.11 (ATCC Accession No. PTA-124184);
  - Rt x hVSIG4 489517.111 (ATCC Accession No. PTA-124185); and
  - Rt x hVSIG4 489518.11 (ATCC Accession No. PTA-124186); and
  a light chain variable region of a monoclonal antibody produced by at least one of the following clones:
  - Ms x hVSIG4 528902.11 (ATCC Accession No. PTA-124187);
  - Ms x hVSIG4 528903.111 (ATCC Accession No. PTA-124188);
  - Ms x hVSIG4 528905.11 (ATCC Accession No. PTA-124189);
  - Ms x hVSIG4 528906.11 (ATCC Accession No. PTA-124178);
  - Ms x hVSIG4 528908.11 (ATCC Accession No. PTA-124179);
  - Ms x hVSIG4 528910.111 (ATCC Accession No. PTA-124180);
  - Ms x hVSIG4 528912.11 (ATCC Accession No. PTA-124181);
  - Ms x hVSIG4 528922.111 (ATCC Accession No. PTA-124182);
  - Ms x hVSIG4 528927.111 (ATCC Accession No. PTA-124183);
  - Rt x hVSIG4 489509.11 (ATCC Accession No. PTA-124184);
  - Rt x hVSIG4 489517.111 (ATCC Accession No. PTA-124185); and
  - Rt x hVSIG4 489518.11 (ATCC Accession No. PTA-124186).

Embodiment 4. A monoclonal antibody, wherein the monoclonal antibody comprises:
at least one of
  a heavy chain variable region comprising a complementarity determining region (CDR) of the heavy chain of a monoclonal antibody produced by at least one of the following clones:
  - Ms x hVSIG4 528902.11 (ATCC Accession No. PTA-124187);
  - Ms x hVSIG4 528903.111 (ATCC Accession No. PTA-124188);
  - Ms x hVSIG4 528905.11 (ATCC Accession No. PTA-124189);
  - Ms x hVSIG4 528906.11 (ATCC Accession No. PTA-124178);
  - Ms x hVSIG4 528908.11 (ATCC Accession No. PTA-124179);
  - Ms x hVSIG4 528910.111 (ATCC Accession No. PTA-124180);
  - Ms x hVSIG4 528912.11 (ATCC Accession No. PTA-124181);
  - Ms x hVSIG4 528922.111 (ATCC Accession No. PTA-124182);
  - Ms x hVSIG4 528927.111 (ATCC Accession No. PTA-124183);
  - Rt x hVSIG4 489509.11 (ATCC Accession No. PTA-124184);
  - Rt x hVSIG4 489517.111 (ATCC Accession No. PTA-124185); and
  - Rt x hVSIG4 489518.11 (ATCC Accession No. PTA-124186); and
  a light chain variable region comprising a complementarity determining region (CDR) of the light chain of a monoclonal antibody produced by at least one of the following clones:
  - Ms x hVSIG4 528902.11 (ATCC Accession No. PTA-124187);
  - Ms x hVSIG4 528903.111 (ATCC Accession No. PTA-124188);
  - Ms x hVSIG4 528905.11 (ATCC Accession No. PTA-124189);
  - Ms x hVSIG4 528906.11 (ATCC Accession No. PTA-124178);
  - Ms x hVSIG4 528908.11 (ATCC Accession No. PTA-124179);
  - Ms x hVSIG4 528910.111 (ATCC Accession No. PTA-124180);
  - Ms x hVSIG4 528912.11 (ATCC Accession No. PTA-124181);

Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186).

Embodiment 5. The monoclonal antibody of Embodiment 4, wherein the monoclonal antibody comprises each of the CDRs of the heavy chain of a monoclonal antibody produced by one of the following clones:
Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186).

Embodiment 6. The monoclonal antibody of either of Embodiments 4 or 6, wherein the monoclonal antibody comprises each of the CDRs of the light chain of a monoclonal antibody produced by one of the following clones:
Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186).

Embodiment 7. A monoclonal antibody, wherein the monoclonal antibody comprises an amino acid sequence that is
at least 80% identical to the amino acid sequence of at least one complementarity determining region (CDR) of the heavy chain variable region of a monoclonal antibody produced by at least one of the following clones:
Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186);
or
at least 80% identical to the amino acid sequence of at least one complementarity determining region (CDR) of the light chain variable region of a monoclonal antibody produced by at least one of the following clones:
Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186);
or both.

Embodiment 8. The monoclonal antibody of Embodiment 7, wherein the monoclonal antibody comprises an amino acid sequence that is
at least 80% identical to the amino acid sequence of each of the complementarity determining regions (CDRs) of the heavy chain variable region of a monoclonal antibody produced by at least one of the following clones:

Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186);
and
at least 80% identical to the amino acid sequence of each of the complementarity determining regions (CDRs) of the light chain variable region of a monoclonal antibody produced by at least one of the following clones:
Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186).

Embodiment 9. The monoclonal antibody of any one of Embodiments 2 to 8, wherein the antibody binds to VSIG-4.

Embodiment 10. The monoclonal antibody of any one of Embodiments 1 to 9, wherein the monoclonal antibody is coupled directly or indirectly to a detectable marker.

Embodiment 11. The monoclonal antibody of any one of Embodiments 1 to 10, wherein the monoclonal antibody comprises an IgG antibody.

Embodiment 12. The monoclonal antibody of any one of Embodiments 1 to 11, wherein the monoclonal antibody abrogates the binding of VSIG-4 to a VSIG-4 ligand.

Embodiment 13. The monoclonal antibody of any one of Embodiments 1 to 12, wherein the VSIG-4 ligand comprises SIGLEC-7.

Embodiment 14. The monoclonal antibody of Embodiment 12 or 13, wherein at least one of VSIG-4 and the VSIG-4 ligand are on a cell surface.

Embodiment 15. The monoclonal antibody of any one of Embodiments 12 to 14, wherein VSIG-4 is on the surface of an M2c macrophage.

Embodiment 16. The monoclonal antibody of any one of Embodiments 12 to 15, wherein the monoclonal antibody abrogates a cell-cell interaction.

Embodiment 17. The monoclonal antibody of any one of Embodiments 1 to 16, wherein the monoclonal antibody binds to an extracellular domain of VSIG-4.

Embodiment 18. The monoclonal antibody of any one of Embodiments 1 to 17, wherein the monoclonal antibody binds to a VSIG-4 polypeptide.

Embodiment 19. The monoclonal antibody of any one of Embodiments 1 to 18, wherein the monoclonal antibody binds to glycosylated and unglycosylated VSIG-4.

Embodiment 20. The monoclonal antibody of any one of Embodiments 1 to 19, wherein the monoclonal antibody comprises an antigen-binding fragment comprising at least one of a Fab fragment, a Fab' fragment, a $F(ab)_2$ fragment, and a Fv fragment.

Embodiment 21. A composition comprising the monoclonal antibody of any one of Embodiments 1 to 20.

Embodiment 22. A kit comprising the monoclonal antibody of any one of Embodiments 1 to 20.

Embodiment 23. The monoclonal antibody of any one of Embodiments 1 to 20 for use in a method of treating a mammalian cancer.

Embodiment 24. The monoclonal antibody of any one of Embodiments 1 to 20 for use in a method of treating an autoimmune disease.

Embodiment 25. A method of treating a mammalian cancer comprising exposing a mammal comprising a mammalian cancer cell to the monoclonal antibody of any one of Embodiments 1 to 20.

Embodiment 26. The method of Embodiment 25 wherein VSIG-4 expression is amplified in a patient sample comprising the mammalian cancer cell.

Embodiment 27. The method of Embodiment 25 wherein VSIG-4 expression is amplified in a macrophage of the patient sample comprising the mammalian cancer cell.

Embodiment 28. The method any one of Embodiments 25 to 27 wherein the mammalian cancer cell comprises a lung cancer cell or a glioma.

Embodiment 29. The method of any one of Embodiments 25 to 28 wherein the mammalian cancer cell is also exposed to chemotherapy or radiation therapy.

Embodiment 30. A method of detecting cancer in a mammal comprising exposing a mammalian cancer cell to the monoclonal antibody of any one of Embodiments 1 to 20.

Embodiment 31. A method of treating an autoimmune disease in a mammal comprising exposing a cell of the mammal to the monoclonal antibody of any one of Embodiments 1 to 20.

Embodiment 32. The method of Embodiment 31 wherein VSIG-4 expression is amplified in a patient sample comprising the mammalian cell.

Embodiment 33. The method of Embodiment 32 wherein VSIG-4 expression is amplified in a macrophage of the patient sample comprising the mammalian cell.

Embodiment 34. The method of any one of Embodiments 31 to 33, wherein the autoimmune disease comprises autoimmune type 1 diabetes mellitus, rheumatoid arthritis, psoriasis, or lupus.

Embodiment 35. The monoclonal antibody of any one of Embodiments 1 to 20 for use in a method of treating an autoimmune disease.

Exemplary Hybridoma Cell Line Embodiments

Embodiment 1. A hybridoma cell line Ms x hVSIG4 528902.11 deposited with the American Type Culture Collection (ATCC) as ATCC accession number PTA-124187.

Embodiment 2. A hybridoma cell line Ms x hVSIG4 528903.111 deposited with the American Type Culture Collection (ATCC) as ATCC accession number PTA-124188.

Embodiment 3. A hybridoma cell line Ms x hVSIG4 528905.11 deposited with the American Type Culture Collection (ATCC) as ATCC accession number PTA-124189.

Embodiment 4. A hybridoma cell line Ms x hVSIG4 528906.11 deposited with the American Type Culture Collection (ATCC) as ATCC accession number PTA-124178.

Embodiment 5. A hybridoma cell line Ms x hVSIG4 528908.11 deposited with the American Type Culture Collection (ATCC) as ATCC accession number PTA-124179.

Embodiment 6. A hybridoma cell line Ms x hVSIG4 528910.111 deposited with the American Type Culture Collection (ATCC) as ATCC accession number PTA-124180.

Embodiment 7. A hybridoma cell line Ms x hVSIG4 528912.11 deposited with the American Type Culture Collection (ATCC) as ATCC accession number PTA-124181.

Embodiment 8. A hybridoma cell line Ms x hVSIG4 528922.111 deposited with the American Type Culture Collection (ATCC) as ATCC accession number PTA-124182.

Embodiment 9. A hybridoma cell line Ms x hVSIG4 528927.111 deposited with the American Type Culture Collection (ATCC) as ATCC accession number PTA-124183.

Embodiment 10. A hybridoma cell line Rt x hVSIG4 489509.11 deposited with the American Type Culture Collection (ATCC) as ATCC accession number PTA-124184.

Embodiment 11. A hybridoma cell line Rt x hVSIG4 489517.111 deposited with the American Type Culture Collection (ATCC) as ATCC accession number PTA-124185.

Embodiment 12. A hybridoma cell line Rt x hVSIG4 489518.11 deposited with the American Type Culture Collection (ATCC) as ATCC accession number PTA-124186.

Exemplary Monoclonal Antibody Produced by Hybridoma Cell Line Embodiments

Embodiment 1. A monoclonal antibody produced by the hybridoma cell line Ms x hVSIG4 528902.11 deposited as ATCC accession number PTA-124187.

Embodiment 2. A monoclonal antibody produced by the hybridoma cell line Ms x hVSIG4 528903.111 deposited as ATCC accession number PTA-124188.

Embodiment 3. A monoclonal antibody produced by the hybridoma cell line Ms x hVSIG4 528905.11 deposited as ATCC accession number PTA-124189.

Embodiment 4. A monoclonal antibody produced by the hybridoma cell line Ms x hVSIG4 528906.11 deposited as ATCC accession number PTA-124178.

Embodiment 5. A monoclonal antibody produced by the hybridoma cell line Ms x hVSIG4 528908.11 deposited as ATCC accession number PTA-124179.

Embodiment 6. A monoclonal antibody produced by the hybridoma cell line Ms x hVSIG4 528910.111 deposited as ATCC accession number PTA-124180.

Embodiment 7. A monoclonal antibody produced by the hybridoma cell line Ms x hVSIG4 528912.11 deposited as ATCC accession number PTA-124181.

Embodiment 8. A monoclonal antibody produced by the hybridoma cell line Ms x hVSIG4 528922.111 deposited as ATCC accession number PTA-124182.

Embodiment 9. A monoclonal antibody produced by the hybridoma cell line Ms x hVSIG4 528927.111 deposited as ATCC accession number PTA-124183.

Embodiment 10. A monoclonal antibody produced by the hybridoma cell line Rt x hVSIG4 489509.11 deposited as ATCC accession number PTA-124184.

Embodiment 11. A monoclonal antibody produced by the hybridoma cell line Rt x hVSIG4 489517.111 deposited as ATCC accession number PTA-124185.

Embodiment 12. A monoclonal antibody produced by the hybridoma cell line Rt x hVSIG4 489518.11 deposited as ATCC accession number PTA-124186.

Embodiment 13. A monoclonal antibody comprising the complementarity-determining regions (CDRs) of the monoclonal antibody produced by the hybridoma cell line Ms x hVSIG4 528902.11 deposited as ATCC accession number PTA-124187.

Embodiment 14. A monoclonal antibody comprising the complementarity-determining regions (CDRs) of the monoclonal antibody produced by the hybridoma cell line Ms x hVSIG4 528903.111 deposited as ATCC accession number PTA-124188.

Embodiment 15. A monoclonal antibody comprising the complementarity-determining regions (CDRs) of the monoclonal antibody produced by the hybridoma cell line Ms x hVSIG4 528905.11 deposited as ATCC accession number PTA-124189.

Embodiment 16. A monoclonal antibody comprising the complementarity-determining regions (CDRs) of the monoclonal antibody produced by the hybridoma cell line Ms x hVSIG4 528906.11 deposited as ATCC accession number PTA-124178.

Embodiment 17. A monoclonal antibody comprising the complementarity-determining regions (CDRs) of the monoclonal antibody produced by the hybridoma cell line Ms x hVSIG4 528908.11 deposited as ATCC accession number PTA-124179.

Embodiment 18. A monoclonal antibody comprising the complementarity-determining regions (CDRs) of the monoclonal antibody produced by the hybridoma cell line Ms x hVSIG4 528910.111 deposited as ATCC accession number PTA-124180.

Embodiment 19. A monoclonal antibody comprising the complementarity-determining regions (CDRs) of the monoclonal antibody produced by the hybridoma cell line Ms x hVSIG4 528912.11 deposited as ATCC accession number PTA-124181.

Embodiment 20. A monoclonal antibody comprising the complementarity-determining regions (CDRs) of the monoclonal antibody produced by the hybridoma cell line Ms x hVSIG4 528922.111 deposited as ATCC accession number PTA-124182.

Embodiment 21. A monoclonal antibody comprising the complementarity-determining regions (CDRs) of the monoclonal antibody produced by the hybridoma cell line Ms x hVSIG4 528927.111 deposited as ATCC accession number PTA-124183.

Embodiment 22. A monoclonal antibody comprising the complementarity-determining regions (CDRs) of the monoclonal antibody produced by the hybridoma cell line Rt x hVSIG4 489509.11 deposited as ATCC accession number PTA-124184.

Embodiment 23. A monoclonal antibody comprising the complementarity-determining regions (CDRs) of the monoclonal antibody produced by the hybridoma cell line Rt x hVSIG4 489517.111 deposited as ATCC accession number PTA-124185.

Embodiment 24. A monoclonal antibody comprising the complementarity-determining regions (CDRs) of the monoclonal antibody produced by the hybridoma cell line Rt x hVSIG4 489518.11 deposited as ATCC accession number PTA-124186.

The present invention is illustrated by the following examples. It is to be understood that the particular examples, materials, amounts, and procedures are to be interpreted broadly in accordance with the scope and spirit of the invention as set forth herein.

EXAMPLES

Unless otherwise indicated, all incubations in the following examples were at room temperature and all reagents, starting materials, and solvents used were purchased from commercial suppliers (such as Sigma-Aldrich, St. Louis, MO) and were used without further purification unless otherwise indicated.

Example 1—Characterization of VSIG4-Siglec7 Interaction

Human Siglec7 (hSiglec7) (Uniprot number: Q9Y286) and human VSIG4 (hVSIG4) (Uniprot number: Q9Y279; Gene ID 11326) were expressed recombinantly in HEK293, NS0, or CHO cells to provide recombinant human Siglec7 (rhSiglec7) and recombinant human VSIG4 (rhVSIG4). Proteins were tagged with a variety of N- or C-terminal tags, as indicated, such as His, Fc or GFP, to enable purification and analysis in the various assays.

Interaction of rhVSIG4 and biotinylated rhSiglec7. Soluble rhVSIG4 was coated on a standard ELISA plate and, after removing excess protein and blocking additional binding sites on the plate with BSA, incubated with soluble rhSIGLEC 7. Biotinylated rhSIGLEC-7 was detected using Streptavidin-horseradish peroxidase (HRP). After background correction, an absorbance of 2.3 was detected at 452 nm in a standard plate reader.

HEK/eGFP Transfectant and Fc protein flow screen. eGFP-transfected HEK293 cells expressing either human VSIG-4 or human Siglec-7 were harvested, washed with RDFII staining buffer (0.5% (w/v) BSA, 10 mM HEPES, 100 mM Sodium Chloride, 0.01% Sodium Azide, pH 7.2), counted, aliquoted at 100,000 cells/sample, and incubated with varying amounts of recombinant human Siglec-7 or VSIG-4 proteins containing a human IgG Fc region (rhSiglec-7/Fc or rhVSIG-4/Fc). Protein concentrations tested were between 500 ng/mL and 6 µg/mL. The transfectants and Fc proteins were incubated for 30 minutes at room temperature, then anti-human IgG Fc-APC detection antibody (FAB110A, R&D Systems, Minneapolis, MN) was added for another 20 minutes. The cells were then washed with RDFII staining buffer and analyzed on either a Novocyte flow cytometer (ACEA Biosciences, Inc., San Diego, CA) or a LSRII FORTESSA flow cytometer (BD Biosciences, San Jose, CA).

Example 2—Identification of Anti-VSIG4 Antibodies and VSIG4-Siglec7 Blocking Antibodies Using panels of monoclonal antibodies made against the human or mouse VSIG4 protein (Uniprot number: Q9Y279 or F6TUL9, respectively), antibodies that bind to VSIG-4 were identified by direct ELISA and Flow Cytometry. Clones producing the VSIG-4-binding antibodies are listed in Table 1.

The ability of these anti-VSIG-4 antibodies to abrogate binding of VSIG-4 to the Siglec-7 protein was also determined, as further described below.

VSIG4-Siglec7 blocking assay. Human VSIG-4 HEK/eGFP transfectants were harvested, washed with RDFII staining buffer, counted, aliquoted at a concentration of 100,000 cells/sample, and incubated with 2.5 µg/mL anti-VSIG-4 antibody for 30 minutes at room temperature. The cells were washed with RDFII staining buffer, and 4 µg/mL hSiglec-7/Fc protein was added to each tube for 30 minutes. After this incubation, anti-Fc APC detection antibody (FAB110A) was added for another 20 minutes. The cells were then washed with RDFII staining buffer, and analyzed on either an Aceabio Novocyte flow cytometer or a LSRII Fortessa flow cytometer (BD Biosciences, San Jose, CA). Exemplary results are shown in FIG. 5; additional results are shown in Table 1.

TABLE 1

Anti-VSIG-4 Monoclonal Antibodies and their characteristics

| Clone | Host species | Antibody Type | Applications | Kd | Blocking |
|---|---|---|---|---|---|
| Clone Ms x hVSIG4 528902.11 | mouse | IgG3 | WB (neg), FC | ND | N |
| Clone Ms x hVSIG4 528903.111 | mouse | IgG2A | WB, FC | 7.7 nM | Y |
| Clone Ms x hVSIG4 528905.11 | mouse | IgG2B | WB, FC | ND | N |
| Clone Ms x hVSIG4 528906.11 | mouse | IgG2A | FC | 4.6 nM | N |
| Clone Ms x hVSIG4 528908.11 | mouse | IgG2A | WB, FC | 6.3 nM | Y |
| Clone Ms x hVSIG4 528910.111 | mouse | IgG3 | WB, FC | ND | N |
| Clone Ms x hVSIG4 528912.11 | mouse | IgG2A | FC | 60.6 nM | Y |
| Clone Ms x hVSIG4 528922.111 | mouse | IgG2A | WB (neg), FC | ND | N |
| Clone Ms x hVSIG4 528927.111 | mouse | IgG2B | WB, FC | ND | N |
| Clone Rt x hVSIG4 489509.11 | Rat | IgG2A | FC | 1 nM | Y |
| Clone Rt x hVSIG4 489517.111 | Rat | IgG2A | FC | 2.1 nM | Y |
| Clone Rt x hVSIG4 489518.11 | Rat | IgG2A | FC | 0.3 nM | Y |

ND (not determined, no binding observed in SPR assay);
FC (Flow Cytometry),
WB (Western Blot)

Example 3—Characterization of VSIG4-Siglec7 Blocking Antibodies

Generation of Polarized M2c cells. PBMCs were isolated using a SEPMATE/Ficoll gradient isolation protocol according to standard protocols. CD14+ cells were then purified using a positive selection kit for CD14 (Catalog

MAGH105, R&D Systems, Minneapolis, MN). One million CD14 positive cells/mL (total volume of 4 mL) were placed in complete media (RPMI culture media supplemented with 10% Fetal Bovine Serum (ThermoFisher Scientific, Waltham, MA), 1.0 mM Sodium Pyruvate (Invitrogen, Carlsbad, CA), 50 mM 2-mercaptoethanol (Invitrogen), 1x Glutamax (Life Technologies, Grand Island, NY), 1x Penicillin/Streptomycin (Life Technologies, Grand Island, NY), and 1× Non-Essential Amino Acids (Life Technologies, Grand Island, NY)) supplemented with 50 ng/mL hM-CSF (Catalog #216-MC R&D Systems, Minneapolis, MN) for 4 days. On day 5, cells were transferred into fresh media to allow cells to polarize to M2c Macrophages for an additional 3 days, the media additionally containing either 30 ng/mL Dexamethasone (Catalog #1126, Tocris Biosciences, Minneapolis, MN) or 20 ng/mL rhIL-10 (Catalog #217-IL, R&D Systems, Minneapolis, MN).

Flow cytometric detection of VSIG-4 expression in polarized M2c cells. Dexamethasone polarized M2c cells were harvested on day 7, washed two times with 1×PBS, and incubated with Zombie Violet (BioLegend, San Diego, CA) at 1 µL per 100 µL cells for 30 minutes at room temperature to allow for dead cell exclusion. Cells were then washed 2 times with RDFII staining buffer, blocked with human IgG and goat anti-human IgG (Catalog #1597, R&D Systems, Minneapolis, MN) for 10 minutes at 4° C. Cells were then surface stained for 30 minutes at 4° C. with mouse anti-human VSIG4 Alexa Fluor 647, anti-CD14 FITC, and anti-Mer PE (Catalog numbers, FAB982F, FAB8912P, R&D Systems, Minneapolis, MN). The cells were washed with RDFII staining buffer one last time and analyzed on a LSRII Fortessa flow cytometer (BD Biosciences, San Jose, CA). Results are shown in FIG. 6.

Detection of Siglec-7/VSIG-4 interaction in primary M2c cells polarized with 20 ng/mL IL-10. Polarized M2c cells were incubated with varying amounts of hSiglec-7 Fc protein (1 µg/mL to 10 µg/mL) for 30 minutes at room temperature. After this incubation, an anti-Fc PE detection antibody (FAB110P, R&D Systems, Minneapolis, MN) was added for an additional 20 minutes. Following the incubation, the cells were washed with RDFII staining buffer, and co-stained with anti-VSIG4 Alexa Fluor 647 and anti-CD14 FITC antibodies for 30 minutes. Following the incubation with these co-stains, the cells were washed again with RDFII staining buffer and analyzed on a LSRII Fortessa flow cytometer (BD Biosciences, San Jose, CA). Results are shown in FIG. 7.

Antibody pairing and co-inhibition studies for antigen recognition. Antibody pairs were identified by ELISA using a biotinylated antibody detection method and Streptavin-HRP as the detection modality. Results are shown in Table 2. Based on the ability to identify pairs of capture/detection antibodies for VSIG4, the clones are recognizing various epitopes within the protein.

TABLE 2

| Antibody pairs for VSIG-4 | |
|---|---|
| Capture Antibody Clone | Detection Antibody Clone |
| Rt × hVSIG4 489509.11 | Ms × hVSIG4 528903.111 |
|  | Ms × hVSIG4 528906.11 |
|  | Ms × hVSIG4 528908.11 |
|  | Ms × hVSIG4 528912.11 |
|  | Rt × hVSIG4 489517.111 |
|  | Rt × hVSIG4 489518.11 |
| Rt × hVSIG4 489517.111 | Rt × hVSIG4 489509.11 |
| Rt × hVSIG4 489518.11 | Rt × hVSIG4 489509.11 |
| Ms × hVSIG4 528903.111 | Rt × hVSIG4 489509.11 |
| Ms × hVSIG4 528906.11 | Rt × hVSIG4 489509.11 |
| Ms × hVSIG4 528908.11 | Rt × hVSIG4 489509.11 |

Example 4—Glycosylation of VSIG4 and Characterization of Anti-VSIG4 Antibody Binding to Glycosylated VSIG4

To determine whether Siglec7 binds to glycosylated VSIG4 via a post-translationally modified glycan moiety, rhVSIG4 was expressed in E. coli, which lack the glycosyltransferase machinery and produce recombinant proteins devoid of any glycan modifications. VSIG4 produced in E. coli lost the ability to bind Siglec7 despite retaining its known function of binding to complement component iC3b, suggesting that Siglec7 binds to the glycosylated form of VSIG4.

Enzymatic deglycosylation of VSIG4 using a standard deglycosylation enzyme kit, which contains typical sialidase enzymes that cleave α(2,3)- and α(2,6)-linked N-acetylneuraminic acid (NANA, or sialic acids), however, showed binding between VSIG4 and Siglec7 was retained. By incorporating a specific sialidase enzyme that additionally cleaves the relatively rare α(2,8)-linked NANA in addition to α(2,3)- and α(2,6)-linked NANA, a ~10 kD shift in the molecular weight of rhVSIG4, from ~42 kD to the predicted ~32 kD molecular weight, was observed. Moreover, treatment with the expanded deglycosylation enzyme kit abrogated the binding interaction between VSIG4 and Siglec7.

These results indicate that VSIG4 is likely heavily modified by polysialic acid chains via α(2,8)-linked N-acetylneuraminic acid, a relatively rare glycan linkage. The most notable protein containing α(2,8)-linked polysialic acid is CD56/NCAM. (Schnaar et al. Physiological Reviews 2014, 94(2):461-518.) An interaction between Siglec7 and CD56/NCAM was confirmed using Biacore, and the interaction affinity between Siglec7-VSIG4 is roughly equivalent to the interaction affinity between Siglec7-CD56 NCAM.

To confirm that an antibody derived against VSIG4 using the mammalian-derived and fully glycosylated rhVSIG4 binds to the VSIG4 polypeptide and not to the glycan-modification on VSIG4, antibody binding was tested against the fully glycosylated rhVSIG4, the deglycosylated VSIG4, E. coli-derived VSIG4, and CD56/NCAM. Strong binding of the blocking antibody to all VSIG4 species regardless of glycosylation state but not to CD56/NCAM was observed.

Collectively, these results suggest that VSIG4 is heavily modified by a rare glycan linkage, a α(2,8)-linked polysialic acid, and that this modification mediates the interaction between VSIG4 and Siglec7. Furthermore, these results indicate that the blocking antibodies bind specifically to the VSIG4 polypeptide and not to the glycan coat of VSIG4.

Purified recombinant human VSIG4 ectodomain (rhVSIG4) expressed in NS0 cells was subjected to deglycosylation with an enzyme cocktail containing recombinant C.p Neuraminidase (R&D Systems catalog #5080-NM), recombinant F.m. PNGase F (R&D Systems catalog #9109-GH), recombinant E.f. 0-glycosidase (R&D Systems catalog #8886-GH), and recombinant S.p B4Galactosidase (R&D Systems catalog #5549-GH), and supplemented with recombinant M.v. Neuraminidase (R&D Systems catalog #5084-NM). Purified rhVSIG4, both fully glysocylated and deglycosylated, were separated by SDS-PAGE and visualized by silver stain. Results are shown in FIG. 9A. The predicted molecular weight of rhVSIG4 ectodomain in the absence of post-translational modifications is 32 kD, and the observed molecular weight of the fully glycosylated rhVSIG4 ECD is ~41 kD. rhVSIG4 derived from the NS0 mammalian cell line is, therefore, believed to be heavily glycosylated, and the deglycosylation enzyme mix removes nearly all sugar molecules (with M.v. neuraminidase cleaving the 2-8 linked sialic acids).

Recombinant human Siglec7-Fc (rhSiglec7-Fc) was captured on a Biacore CM5 chip modified with Protein A/G/L at ~700 RU capture density and tested for binding with fully glycosylated rhVSIG4, deglycosylated VSIG4, and CD56/NCAM at concentrations ranging between 0.5 nM and 500 nM. As shown in FIG. 9B-FIG. 9D, Siglec7 interacted with rhVSIG4 but not with the deglycosylated VSIG4. Additionally, Siglec7 did not interact with VSIG4 expressed in *E. coli*. CD56/NCAM is heavily glycosylated with a sugar profile similar to VSIG4, and the interaction between Siglec7 and CD56/NCAM further suggests the interaction between Siglec7 and VSIG4 is mediated by a unique glycosylation profile.

Anti-VSIG-4 antibody binding to a VSIG4 polypeptide regardless of glycosylation state was tested using Biacore. Blocking antibody (Rt x hVSIG4 489517.111, Ms x hVSIG4 528906.11,) was captured on a Protein A/G/L chip at ~350 RU and tested for binding to rhVSIG4, mammalian NS0 cell derived rhVSIG4, mammalian derived and fully deglycosylated, VSIG4, *E. coli* derived and free of glycosylation, and CD56/NCAM, a heavily glycosylated protein. All analyte proteins, rhVSIG4 and CD56/NCAM were tested at concentrations ranging between 25 pM and 250 nM. Binding to VSIG4 regardless of VSIG4's glycosylation state and not to CD56/NCAM, a heavily glycosylated molecule with a similar glycoprofile as VSIG4, demonstrates the specificity of an antibody to the VSIG4 amino acid sequence and indicates the antibody is not anti-glycosylation specific. Results are shown in FIG. 10-FIG. 13.

Example 5—Further Characterization of the VSIG4-Siglec7 Interaction and VSIG4-Siglec7 Blocking Antibodies HEK293 cells were transfected with recombinant human VSIG4-eGFP or recombinant human VSIG3-eGFP. The cells were then incubated with a no protein (negative control) or recombinant human Siglec-7-Fc in the indicated doses. Cells were then incubated with an anti-Fc Allophycocyanin (APC). As shown in FIG. 14, recombinant human Siglec-7 binds specifically to HEK293 cells transfected with recombinant human VSIG4 fused to eGFP in a dose-dependent manner, but recombinant human Siglec-7 does not bind to HEK293 cells type transfected with recombinant human VSIG3-eGFP.

Adherent M2c macrophages were polarized with Dexamethasone as described in Example 3. M2c macrophages were incubated with 10 pg/mL, 40 pg/mL or 200 pg/mL anti-human VSIG-4 antibodies to test the antibody's capacity to block the interaction with rhSiglec-7. rhSiglec-7 was tested at concentrations of at 100 pg/mL, 25 pg/mL, or 5 pg/mL. Ms x hVSIG4 528906.11 blocks the interaction of naturally expressed VSIG-4 on M2c macrophages with recombinant human Siglec-7/Fc in a dose dependent manner as shown in FIG. 15-FIG. 18.

Example 6—Direct ELISA Testing of Anti-VSIG-4 Antibodies

Plates were coated with a titration series of recombinant human VSIG4 protein ranging from 400 ng/ml to 1.56 ng/ml in a 4-fold dilution series. Anti-VSIG-4 antibodies were added at 1 mg/ml and incubated for 1 hour followed by goat anti-mouse or a goat anti-rat HRP-conjugated secondary antibodies (to match the primary clones) at a 1:10,000 dilution. The HRP activity was detected by addition of TMB and stop solution addition after 10 minutes. Results were evaluated by absorbance at 540 nm. Representative data are shown in FIG. 19 and are summarized in Table 3.

TABLE 3

Representative ELISA results

| Clone number | VSIG4 from NSO | VSIG from *E. coli* |
| --- | --- | --- |
| Ms × hVSIG4 528902.11 | neg | weak |
| Ms × hVSIG4 528903.111 | pos | pos |
| Ms × hVSIG4 528905.11 | pos | neg |
| Ms × hVSIG4 528906.11 | pos | pos |
| Ms × hVSIG4 528908.11 | pos | pos |
| Ms × hVSIG4 528910.111 | pos | neg |
| Ms × hVSIG4 528912.11 | pos | pos |
| Ms × hVSIG4 528922.111 | neg | pos |
| Ms × hVSIG4 528927.111 | pos | pos |
| Rt × hVSIG4 489509.11 | pos | pos |
| Rt × hVSIG4 489517.111 | pos | pos |
| Rt × hVSIG4 489518.11 | pos | pos |

As shown in Table 3, most antibodies tested detected both glycosylated human VSIG4 expressed in NSO as well as non-glycosylated recombinant human VSIG4 protein expressed in *E. coli*, indicating that the antibodies detect the amino acid component of the protein and not secondary modifications.

The complete disclosure of all patents, patent applications, and publications, and electronically available material (including, for instance, nucleotide sequence submissions in, for example, GenBank and RefSeq, and amino acid sequence submissions in, for example, SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating a mammalian cancer comprising exposing a mammal comprising a mammalian cancer cell to a monoclonal antibody that binds to VSIG-4, wherein the monoclonal antibody comprises:
   a heavy chain variable region comprising the three complementarity determining regions (CDRs) of the heavy chain of a monoclonal antibody produced by Ms x hVSIG4 528902.11 (ATCC Accession No. PTA-124187), and a light chain variable region comprising the three CDRs of the light chain of a monoclonal antibody produced by Ms x hVSIG4 528902.11 (ATCC Accession No. PTA-124187);

a heavy chain variable region comprising the three CDRs of the heavy chain of a monoclonal antibody produced by Ms x hVSIG4 528903.111 (ATCC Accession No. PTA-124188), and a light chain variable region comprising the three CDRs of the light chain of a monoclonal antibody produced by Ms x hVSIG4 528903.111 (ATCC Accession No. PTA-124188);

a heavy chain variable region comprising the three CDRs of the heavy chain of a monoclonal antibody produced by Ms x hVSIG4 528905.11 (ATCC Accession No. PTA-124189), and a light chain variable region comprising the three CDRs of the light chain of a monoclonal antibody produced by Ms x hVSIG4 528905.11 (ATCC Accession No. PTA-124189);

a heavy chain variable region comprising the three CDRs of the heavy chain of a monoclonal antibody produced by Ms x hVSIG4 528906.11 (ATCC Accession No. PTA-124178), and a light chain variable region comprising the three CDRs of the light chain of a monoclonal antibody produced by Ms x hVSIG4 528906.11 (ATCC Accession No. PTA-124178);

a heavy chain variable region comprising the three CDRs of the heavy chain of a monoclonal antibody produced by Ms x hVSIG4 528908.11 (ATCC Accession No. PTA-124179), and a light chain variable region comprising the three CDRs of the light chain of a monoclonal antibody produced by Ms x hVSIG4 528908.11 (ATCC Accession No. PTA-124179);

a heavy chain variable region comprising the three CDRs of the heavy chain of a monoclonal antibody produced by Ms x hVSIG4 528910.111 (ATCC Accession No. PTA-124180), and a light chain variable region comprising the three CDRs of the light chain of a monoclonal antibody produced by Ms x hVSIG4 528910.111 (ATCC Accession No. PTA-124180);

a heavy chain variable region comprising the three CDRs of the heavy chain of a monoclonal antibody produced by Ms x hVSIG4 528912.11 (ATCC Accession No. PTA-124181), and a light chain variable region comprising the three CDRs of the light chain of a monoclonal antibody produced by Ms x hVSIG4 528912.11 (ATCC Accession No. PTA-124181);

a heavy chain variable region comprising the three CDRs of the heavy chain of a monoclonal antibody produced by Ms x hVSIG4 528922.111 (ATCC Accession No. PTA-124182), and a light chain variable region comprising the three CDRs of the light chain of a monoclonal antibody produced by Ms x hVSIG4 528922.111 (ATCC Accession No. PTA-124182);

a heavy chain variable region comprising the three CDRs of the heavy chain of a monoclonal antibody produced by Ms x hVSIG4 528927.111 (ATCC Accession No. PTA-124183), and a light chain variable region comprising the three CDRs of the light chain of a monoclonal antibody produced by Ms x hVSIG4 528927.111 (ATCC Accession No. PTA-124183);

a heavy chain variable region comprising the three CDRs of the heavy chain of a monoclonal antibody produced by Rt x hVSIG4 489509.11 (ATCC Accession No. PTA-124184), and a light chain variable region comprising the three CDRs of the light chain of a monoclonal antibody produced by Rt x hVSIG4 489509.11 (ATCC Accession No. PTA-124184);

a heavy chain variable region comprising the three CDRs of the heavy chain of a monoclonal antibody produced by Rt x hVSIG4 489517.111 (ATCC Accession No. PTA-124185), and a light chain variable region comprising the three CDRs of the light chain of a monoclonal antibody produced by Rt x hVSIG4 489517.111 (ATCC Accession No. PTA-124185); or a heavy chain variable region comprising the three CDRs of the heavy chain of a monoclonal antibody produced by Rt x hVSIG4 489518.11 (ATCC Accession No. PTA-124186), and a light chain variable region comprising the three CDRs of the light chain of a monoclonal antibody produced by Rt x hVSIG4 489518.11 (ATCC Accession No. PTA-124186).

2. A method of detecting cancer in a mammal comprising exposing a mammalian cancer cell to a monoclonal antibody that binds to VSIG-4, wherein the monoclonal antibody comprises:

a heavy chain variable region comprising the three complementarity determining regions (CDRs) of the heavy chain of a monoclonal antibody produced by Ms x hVSIG4 528902.11 (ATCC Accession No. PTA-124187), and a light chain variable region comprising the three CDRs of the light chain of a monoclonal antibody produced by Ms x hVSIG4 528902.11 (ATCC Accession No. PTA-124187);

a heavy chain variable region comprising the three CDRs of the heavy chain of a monoclonal antibody produced by Ms x hVSIG4 528903.111 (ATCC Accession No. PTA-124188), and a light chain variable region comprising the three CDRs of the light chain of a monoclonal antibody produced by Ms x hVSIG4 528903.111 (ATCC Accession No. PTA-124188);

a heavy chain variable region comprising the three CDRs of the heavy chain of a monoclonal antibody produced by Ms x hVSIG4 528905.11 (ATCC Accession No. PTA-124189), and a light chain variable region comprising the three CDRs of the light chain of a monoclonal antibody produced by Ms x hVSIG4 528905.11 (ATCC Accession No. PTA-124189);

a heavy chain variable region comprising the three CDRs of the heavy chain of a monoclonal antibody produced by Ms x hVSIG4 528906.11 (ATCC Accession No. PTA-124178), and a light chain variable region comprising the three CDRs of the light chain of a monoclonal antibody produced by Ms x hVSIG4 528906.11 (ATCC Accession No. PTA-124178);

a heavy chain variable region comprising the three CDRs of the heavy chain of a monoclonal antibody produced by Ms x hVSIG4 528908.11 (ATCC Accession No. PTA-124179), and a light chain variable region comprising the three CDRs of the light chain of a monoclonal antibody produced by Ms x hVSIG4 528908.11 (ATCC Accession No. PTA-124179);

a heavy chain variable region comprising the three CDRs of the heavy chain of a monoclonal antibody produced by Ms x hVSIG4 528910.111 (ATCC Accession No. PTA-124180), and a light chain variable region comprising the three CDRs of the light chain of a monoclonal antibody produced by Ms x hVSIG4 528910.111 (ATCC Accession No. PTA-124180);

a heavy chain variable region comprising the three CDRs of the heavy chain of a monoclonal antibody produced by Ms x hVSIG4 528912.11 (ATCC Accession No. PTA-124181), and a light chain variable region comprising the three CDRs of the light chain of a monoclonal antibody produced by Ms x hVSIG4 528912.11 (ATCC Accession No. PTA-124181);

a heavy chain variable region comprising the three CDRs of the heavy chain of a monoclonal antibody produced by Ms x hVSIG4 528922.111 (ATCC Accession No. PTA-124182), and a light chain variable region comprising the three CDRs of the light chain of a monoclonal antibody produced by Ms x hVSIG4 528922.111 (ATCC Accession No. PTA-124182);

a heavy chain variable region comprising the three CDRs of the heavy chain of a monoclonal antibody produced by Ms x hVSIG4 528927.111 (ATCC Accession No. PTA-124183), and a light chain variable region comprising the three CDRs of the light chain of a monoclonal antibody produced by Ms x hVSIG4 528927.111 (ATCC Accession No. PTA-124183);

a heavy chain variable region comprising the three CDRs of the heavy chain of a monoclonal antibody produced by Rt x hVSIG4 489509.11 (ATCC Accession No. PTA-124184), and a light chain variable region comprising the three CDRs of the light chain of a monoclonal antibody produced by Rt x hVSIG4 489509.11 (ATCC Accession No. PTA-124184);

a heavy chain variable region comprising the three CDRs of the heavy chain of a monoclonal antibody produced by Rt x hVSIG4 489517.111 (ATCC Accession No. PTA-124185), and a light chain variable region comprising the three CDRs of the light chain of a monoclonal antibody produced by Rt x hVSIG4 489517.111 (ATCC Accession No. PTA-124185); or a heavy chain variable region comprising the three CDRs of the heavy chain of a monoclonal antibody produced by Rt x hVSIG4 489518.11 (ATCC Accession No. PTA-124186), and a light chain variable region comprising the three CDRs of the light chain of a monoclonal antibody produced by Rt x hVSIG4 489518.11 (ATCC Accession No. PTA-124186).

3. The method of claim 2, wherein VSIG-4 is on a cell surface.

4. The method of claim 2, wherein the monoclonal antibody binds to an extracellular domain of VSIG-4.

5. The method of claim 2, wherein the monoclonal antibody binds to glycosylated and unglycosylated VSIG-4.

6. The method of claim 2, wherein the monoclonal antibody is coupled directly or indirectly to a detectable marker.

7. The method of claim 2, wherein the monoclonal antibody comprises an IgG antibody.

8. The method of claim 2, wherein the monoclonal antibody comprises an antigen-binding fragment comprising at least one of a Fab fragment, a Fab' fragment, a $F(ab)_2$ fragment, and a FIT fragment.

9. The method of claim 2, wherein the method comprises determining a level of VSIG-4 protein in a patient sample comprising the mammalian cancer cell.

10. The method of claim 2, wherein the method comprises identifying the presence or absence of VSIG-4 protein in a patient sample comprising the mammalian cancer cell.

11. The method of claim 9, wherein the patient sample further comprises a macrophage.

12. The method of claim 11, wherein VSIG-4 is on the surface of an M2c macrophage.

13. The method of claim 2, wherein the monoclonal antibody comprises a monoclonal antibody produced by at least one of the following clones:

Ms x hVSIG4 528902.11 (ATCC Accession No. PTA-124187);

Ms x hVSIG4 528903.111 (ATCC Accession No. PTA-124188);

Ms x hVSIG4 528905.11 (ATCC Accession No. PTA-124189);

Ms x hVSIG4 528906.11 (ATCC Accession No. PTA-124178);

Ms x hVSIG4 528908.11 (ATCC Accession No. PTA-124179);

Ms x hVSIG4 528910.111 (ATCC Accession No. PTA-124180);

Ms x hVSIG4 528912.11 (ATCC Accession No. PTA-124181);

Ms x hVSIG4 528922.111 (ATCC Accession No. PTA-124182);

Ms x hVSIG4 528927.111 (ATCC Accession No. PTA-124183);

Rt x hVSIG4 489509.11 (ATCC Accession No. PTA-124184);

Rt x hVSIG4 489517.111 (ATCC Accession No. PTA-124185); and

Rt x hVSIG4 489518.11 (ATCC Accession No. PTA-124186).

14. A method of detecting VSIG-4 in a patient sample, the method comprising contacting the patient sample with a monoclonal antibody that binds to VSIG-4, wherein the monoclonal antibody comprises:

a heavy chain variable region comprising the three complementarity determining regions (CDRs) of the heavy chain of a monoclonal antibody produced by Ms x hVSIG4 528902.11 (ATCC Accession No. PTA-124187), and a light chain variable region comprising the three CDRs of the light chain of a monoclonal antibody produced by Ms x hVSIG4 528902.11 (ATCC Accession No. PTA-124187);

a heavy chain variable region comprising the three CDRs of the heavy chain of a monoclonal antibody produced by Ms x hVSIG4 528903.111 (ATCC Accession No. PTA-124188), and a light chain variable region comprising the three CDRs of the light chain of a monoclonal antibody produced by Ms x hVSIG4 528903.111 (ATCC Accession No. PTA-124188);

a heavy chain variable region comprising the three CDRs of the heavy chain of a monoclonal antibody produced by Ms x hVSIG4 528905.11 (ATCC Accession No. PTA-124189), and a light chain variable region comprising the three CDRs of the light chain of a monoclonal antibody produced by Ms x hVSIG4 528905.11 (ATCC Accession No. PTA-124189);

a heavy chain variable region comprising the three CDRs of the heavy chain of a monoclonal antibody produced by Ms x hVSIG4 528906.11 (ATCC Accession No. PTA-124178), and a light chain variable region comprising the three CDRs of the light chain of a monoclonal antibody produced by Ms x hVSIG4 528906.11 (ATCC Accession No. PTA-124178);

a heavy chain variable region comprising the three CDRs of the heavy chain of a monoclonal antibody produced by Ms x hVSIG4 528908.11 (ATCC Accession No. PTA-124179), and a light chain variable region comprising the three CDRs of the light chain of a monoclonal antibody produced by Ms x hVSIG4 528908.11 (ATCC Accession No. PTA-124179);

a heavy chain variable region comprising the three CDRs of the heavy chain of a monoclonal antibody produced by Ms x hVSIG4 528910.111 (ATCC Accession No. PTA-124180), and a light chain variable region comprising the three CDRs of the light chain of a monoclonal antibody produced by Ms x hVSIG4 528910.111 (ATCC Accession No. PTA-124180);

a heavy chain variable region comprising the three CDRs of the heavy chain of a monoclonal antibody produced by Ms x hVSIG4 528912.11 (ATCC Accession No. PTA-124181), and a light chain variable region comprising the three CDRs of the light chain of a monoclonal antibody produced by Ms x hVSIG4 528912.11 (ATCC Accession No. PTA-124181);

a heavy chain variable region comprising the three CDRs of the heavy chain of a monoclonal antibody produced by Ms x hVSIG4 528922.111 (ATCC Accession No. PTA-124182), and a light chain variable region comprising the three CDRs of the light chain of a monoclonal antibody produced by Ms x hVSIG4 528922.111 (ATCC Accession No. PTA-124182);

a heavy chain variable region comprising the three CDRs of the heavy chain of a monoclonal antibody produced by Ms x hVSIG4 528927.111 (ATCC Accession No. PTA-124183), and a light chain variable region comprising the three CDRs of the light chain of a monoclonal antibody produced by Ms x hVSIG4 528927.111 (ATCC Accession No. PTA-124183);

a heavy chain variable region comprising the three CDRs of the heavy chain of a monoclonal antibody produced by Rt x hVSIG4 489509.11 (ATCC Accession No. PTA-124184), and a light chain variable region comprising the three CDRs of the light chain of a monoclonal antibody produced by Rt x hVSIG4 489509.11 (ATCC Accession No. PTA-124184);

a heavy chain variable region comprising the three CDRs of the heavy chain of a monoclonal antibody produced by Rt x hVSIG4 489517.111 (ATCC Accession No. PTA-124185), and a light chain variable region comprising the three CDRs of the light chain of a monoclonal antibody produced by Rt x hVSIG4 489517.111 (ATCC Accession No. PTA-124185); or a heavy chain variable region comprising the three CDRs of the heavy chain of a monoclonal antibody produced by Rt x hVSIG4 489518.11 (ATCC Accession No. PTA-124186), and a light chain variable region comprising the three CDRs of the light chain of a monoclonal antibody produced by Rt x hVSIG4 489518.11 (ATCC Accession No. PTA-124186).

15. The method of claim 14, wherein the monoclonal antibody comprises a monoclonal antibody produced by at least one of the following clones:

Ms x hVSIG4 528902.11 (ATCC Accession No. PTA-124187);
Ms x hVSIG4 528903.111 (ATCC Accession No. PTA-124188);
Ms x hVSIG4 528905.11 (ATCC Accession No. PTA-124189);
Ms x hVSIG4 528906.11 (ATCC Accession No. PTA-124178);
Ms x hVSIG4 528908.11 (ATCC Accession No. PTA-124179);
Ms x hVSIG4 528910.111 (ATCC Accession No. PTA-124180);
Ms x hVSIG4 528912.11 (ATCC Accession No. PTA-124181);
Ms x hVSIG4 528922.111 (ATCC Accession No. PTA-124182);
Ms x hVSIG4 528927.111 (ATCC Accession No. PTA-124183);
Rt x hVSIG4 489509.11 (ATCC Accession No. PTA-124184);
Rt x hVSIG4 489517.111 (ATCC Accession No. PTA-124185); and
Rt x hVSIG4 489518.11 (ATCC Accession No. PTA-124186).

16. The method of claim 14, wherein the method comprises determining a level of VSIG-4 protein in the patient sample.

17. The method of claim 14, wherein VSIG-4 is on a cell surface.

18. The method of claim 14, wherein VSIG-4 is on the surface of a cancer cell or a tumor cell.

19. The method of claim 14, wherein VSIG-4 is on the surface of a macrophage.

* * * * *

UNITED STATES PATENT AND TRADEMARK OFFICE
CERTIFICATE OF CORRECTION

PATENT NO. : 11,897,958 B2
APPLICATION NO. : 16/997797
DATED : February 13, 2024
INVENTOR(S) : Birte Aggeler et al.

Page 1 of 1

It is certified that error appears in the above-identified patent and that said Letters Patent is hereby corrected as shown below:

In the Claims

In Column 43, Line 52 (Claim 8): 'and a FIT fragment.' should read --and a Fv fragment.--

Signed and Sealed this
Sixteenth Day of July, 2024

Katherine Kelly Vidal
Director of the United States Patent and Trademark Office